US007745604B2

(12) United States Patent
Low et al.

(10) Patent No.: US 7,745,604 B2
(45) Date of Patent: Jun. 29, 2010

(54) UPSTREAM CONTROL ELEMENTS OF THE PROOPIOMELANOCORTIN GENE AND THEIR USE

(75) Inventors: Malcolm J. Low, Lake Oswego, OR (US); Marcelo Rubinstein, Buenos Aires (AR); Flavio Silva Junqueira de Souza, Buenos Aires (AR)

(73) Assignee: Oregon Health & Science University, Portland, OR (US)

( * ) Notice: Subject to any disclaimer, the term of this patent is extended or adjusted under 35 U.S.C. 154(b) by 768 days.

(21) Appl. No.: 11/503,426

(22) Filed: Aug. 10, 2006

(65) Prior Publication Data

US 2007/0059797 A1 Mar. 15, 2007

Related U.S. Application Data

(60) Division of application No. 10/336,091, filed on Jan. 3, 2003, now Pat. No. 7,125,979, which is a continuation-in-part of application No. 10/255,175, filed on Sep. 24, 2002, now abandoned.

(60) Provisional application No. 60/324,406, filed on Sep. 24, 2001, provisional application No. 60/392,109, filed on Jun. 28, 2002.

(51) Int. Cl.

| | |
|---|---|
| ***C07H 21/04*** | (2006.01) |
| ***C12N 15/00*** | (2006.01) |
| ***C12N 5/00*** | (2006.01) |

(52) U.S. Cl. .................... 536/24.1; 435/320.1; 435/325

(58) Field of Classification Search ....................... None
See application file for complete search history.

(56) References Cited

U.S. PATENT DOCUMENTS

| | | | |
|---|---|---|---|
| 4,175,122 | A | 11/1979 | Lazarus |
| 4,223,017 | A | 9/1980 | Lazarus |
| 4,355,025 | A | 10/1982 | Lazarus |
| 4,701,093 | A | 10/1987 | Meyer |
| 4,701,441 | A | 10/1987 | Kalra |
| 5,284,839 | A | 2/1994 | Siren |
| 5,696,093 | A | 12/1997 | Tseng |
| 2002/0141985 | A1 | 10/2002 | Pittner et al. |

FOREIGN PATENT DOCUMENTS

| | | |
|---|---|---|
| WO | WO 97/46579 | 12/1997 |
| WO | WO 01/68699 | 9/2001 |
| WO | WO 02/47122 | 6/2002 |
| WO | WO 02/47712 | 6/2002 |

OTHER PUBLICATIONS

Sequence search results: result 5, accession No. AA119009.*
Dickmeis et al. (Briefings in functionasl genomics and proteomics, 2005. vol. 3, No. 4, pp. 332-350).*
U.S. Appl. No. 60/256,216, filed Sep. 24, 2001.
Ensembl Gene ID ENSG00000115138 *Homo sapiens* POMC http://www.glovar.org/Homo_sapiens/geneview?gene=ENSG00000115138, May 24, 2005.
Ensembl Gene ID ENSMUSG00000020660 Mus musculus POMC http://www.informatics.jax.org/javawi2/servlet/WIFetch?page=markerDetail&key=12609, May 25, 2005.
Allen, et al., "Effects of peptide YY and neuropeptide Y on gastric emptying in man." *Digestion* 30:255-262, 1984.
Bagnol, et al., "Anatomy of an endogenous antagonist: relationship between Agouti-related protein and proopiomelanocortin in brain," *J. Neurosci*. 15;19(18):RC26, 1999.
Bartolome, et al., "Peptide YY secretion in morbidly obese patients before and after vertical banded gastroplasty," *Obes. Surg.* 12(3):324-327, 2002. (Abstract).
Batterham RL, et al., "Gut hormone PYY(3-36) physiologically inhibits food intake," *Nature* 418(6898):650-654, 2002.
Broberger, et al., "Subtypes Y1 and Y2 of the neuropeptide Y receptor are respectively expressed in pro-opiomelanocortin- and neuropeptide-Y-containing neurons of the rat hypothalamic arcuate nucleus," *Neuroendocrinology* 66(6):393-408, 1997.
Butler, et al., "A unique metabiolic syndrome causes obesity in the melanocortin-3 receptor-deficient mouse," *Endocrinology* 141(9):3518-3521, 2000.
Comuzzie, et al., "A major quantitative trait locus determining serum leptin levels and fat mass is located on human chromosome 2," *Nature Genetics* 15(3):273-276, 1997.
Cowley, et al., "Leptin activates anorexigenic POMC neurons through a neural network in the arcuate nucleus," *Nature* 411:480-484, 2001.
Csiffary, et al., "Neuropeptide Y innervation of ACTH-immunoreactive neurons in the arcuate nucleus of rats: a correlated light and electron microscopic double immunolabeling study," *Brain Res.* 506(2):215-22, 1990.
Ekblad and Sundler, "Distribution of pancreatic polypeptide and peptide YY,"*Peptides* 23:251-261, 2002.
Fan, et al., "Role of melanocortinergic neurons in feeding and the agouti obesity syndrome," *Nature* 358:165-168, 1997.
Glaum, et al., "Leptin, the obese gene product, rapidly modulates synaptic transmission in the hypothalamus," *Mol. Pharmacol.* 50(2):230-5, 1996.
Hagan, "Peptide YY: a key mediator of orexigenic behavior," *Peptides* 23:377-382, 2002.
Hager et al., "A genome-wide scan for human obesity genes reveals a major susceptibility locus on chromosome 10," *Nature Genetics* 20:304-308, 1998.
Hakansson, et al., "Leptin receptor immunoreactivity in chemically defined target neurons of the hypothalamus," *J. Neurosci.* 18(1):559-72, 1998.
Hammer et al., "Pituitary-specific and hormonally regulated gene expression directed by the rat proopiomelanocortin promoter in transgenic mice," *Molecular Endocrinology* 4(11):1689-1697, 1990.

(Continued)

*Primary Examiner*—Celine X Qian
(74) *Attorney, Agent, or Firm*—Klarquist Sparkman, LLP

(57) ABSTRACT

The nucleic acid sequence of the POMC enhancer is disclosed herein. Sequences from the human, rat, rabbit, hamster, mouse, and cow POMC enhancer are disclosed. Hybrid transgenes, comprising a POMC transcriptional control element operably linked to a nucleic acid sequence encoding a marker are also enclosed. In addition, transgenic mice carrying a hybrid transgene including a POMC control element operably linked to a marker are disclosed herein.

28 Claims, 25 Drawing Sheets

OTHER PUBLICATIONS

Harding and McDonald, "Identification and characterization of the emetic effects of peptide YY," *Peptides* 10:21-24, 1989.
Heisler, et al., "Activation of central melanocortin pathways by fenfluramine," *Science* 0:1-3, 2002.
Hixson et al., "Normal variation in leptin levels is associated with polymorphisms in the proopiomelanocortin gene, POMC," *The Journal of Clinical Endocrinology & Metabolism* 84(9):3187-3191, 1999.
Horvath et al. "GABAergic and catecholaminergic innervation of mediobasal hypothalamic beta-endorphin cells projecting to the medial preoptic area." *Neuroscience* 51(2):391-9, 1992.
Horvath, et al., "Heterogeneity in the neuropeptide Y-containing neurons of the rat arcuate nucleus: GABAergic and non-GABAergic subpopulations," *Brain Res.* 756(1-2):283-286, 1997.
Iyengar, et al., "Characterization of neuropeptide Y-induced feeding in mice: do Y1-Y6 receptor subtypes mediate feeding?" *The Journal of Pharmacology and Experimental Therapeutics* 289(2):1031-1040, 1999.
Japón, et al., "In situ hybridization analysis of anterior pituitary hormone gene expression during fetal mouse development," *The Journal of Histochemistry and Cytochemistry* 42(8):1117-1125, 1994.
Kim, et al., "The central melanocortin system affects the hypothalamo-pituitary thryoid axis and may mediate the effect of leptin," *J. Clin. Invest.* 105(7):1005-11, 2000.
King, et al., "Regulation of neuropeptide Y release by neuropeptide Y receptor ligands and calcium channel antagonists in hypothalamic slices," *J. Neurochem.* 73(2):641-6, 1999.
Kirby, et al., "Defining structrual requirements for neuropeptide Y receptors using truncated and conformationally restricted analogues," *J. Med. Chem.* 36(3):385-393, 1993.
Krude and Grüters, "Implications of proopiomelanocortin (POMC) mutations in humans: the POMC deficiency syndrome," *Trends Endocrino Met* 11(1):15-22, 2000.
Krude et al., "Severe early-onset obesity, adrenal insufficiency and red hair pigmentation caused by POMC mutations in humans," *Nature Genetics* 19:155-157, 1998.
LeBail and Boenf, "What hormones may regulate fodd intake in fish?" First Workshop (COST 827) on voluntary food intake in fish, Aberdeen (UK), Apr. 3-5, 1997. (Abstracts of oral communications and posters).
Lee and Nathans, "Proliferin secreted by cultured cells binds to mannose 6-phosphate receptors," *J. Biol. Chem.* 263(7):3521-7, 1988.
Liu et al., "DNA elements with AT-rich core sequences direct pituitary cell-specific expression of the pro-opiomelanocortin gene in transgenic mice," *Biochem. J.* 312:827-832, 1995.
Liu et al., "Identification of DNA elements cooperatively activating proopiomelanocortin gene expression in the pituitary glands of transgenic mice," *Molecular and Cellular Biology* 12(9):3978-3990, 1992.
Low et al., "Post-translational processing of proopiomelanocortin (POMC) in mouse pituitary melanotroph tumors induced by a POMC-simian virus 40 large T antigent transgene," *The Journal of Biological Chemistry* 268(33):24967-24975, 1993.
Low, "Chapter 12: The identification of neuropeptide gene regulatory elements in transgenic mice," *Methods in Molecular Biology* 13:181-203, 1992.
Low, et al., "Chapter 15: Transgenic analysis of the proopiomelanocortin neuroendocrine system," *Contemporary Endocrinology: Transgenics in Endocrinology*, pp. 319-337.
Lyznicki, et al., "Obesity: Assessment and management in primary care," *American Family Physician* 63(11):2185-2196, 2001.
Malaisse-Lagae, et al., "Pancreatic polypeptide=a possible role in the regulation of fodd intake in the mouse hypothesis," *Experientia* 33:915-917, 1977.
Marks, et al., "Role of the central melanocortin system in cachexia," *Cancer Research* 61:1432-1438, 2001.
Naveilhan, et al., "Attenuation of hypercholesterolemia and hyperglycemia in ob/ob mice by NPY Y2 receptor ablation," *Peptides* 23(6):1087-1091, 2002.
Naveilhan, et al., "Distinct roles of the Y1 and Y2 receptors on neuropeptide Y-induced sensitization to sedation," *J. Neurochem.* 78(6):1201-1207, 2001.
Naveilhan, et al., "Normal feeding behavior, body weight and leptin response require the neuropeptide Y Y2 receptor," *Nat. Med.* 5(10):1188-1193, 1999.
Okada, et al., "Peripherally not centrally adminstered peptide YY(PYY) decreases high fat diet intake," Abstract 520B, 75$^{th}$ Annual Meeting of Endocrine Society, 1993. (Abstract).
Olsson, et al., "CCK, gastric emptying and stomach motility in the rainbow trout, Oncorhyachus," First Workshop (COST 827) on voluntary food intake in fish, Aberdeen (UK), Apr. 3-5, 1997. Abstracts of oral communications and posters.
Peter, et al., "Neuroendocrine regulation of appetite in fish," First Workshop (COST 827) on voluntary food intake in fish, Aberdeen (UK), Apr. 3-5, 1997. (Abstracts of oral communications and posters).
Powis, et al., "Leptin depolarizes rat hypothalamic paraventricular nucleus neurons," *Am. J. Physiol.* 274(5 Pt 2):R1468-72, 1998.
Rotimi et al., "The quantitative trait locus on chromosome 2 for serum leptin levels is confirmed in African-Americans," *Diabetes* 48(3):643-644, 1999.
Rubinstein et al., "Rat and mouse proopiomelanocortin gene sequences target tissue-specific expression to the pituitary gland by not to the hypothalamus of transgenic mice," *Molecular Neuroendocrinology* 58:373-380, 1993.
Schwartz, et al., "Central nervous system control of food intake," *Nature* 404(6778):661-671, Review, 2000.
Smart and Low, "Spontaneous and induced genetic mutations of the POMC system," *Transgenic Models in Endocrinology*, pp. 175-194.
Spanswick, et al., "Leptin inhibits hypothalamic neurons by activation of ATP-sensitive potassium channels," *Nature* 390(6659):521-5, 1997.
Stead, et al., "Effect of environment factors on food consumption and growth of individual Atlantic salmon (salmo salai L.)," First Workshop (COST 827) on voluntary food intake in fish, Aberdeen (UK), Apr. 3-5, 1997. (Abstracts of oral communications and posters).
Tsukada, et al., "Functional analysis of the cell-specific enhancer in the human proopiomelanocortin gene by beta-galactosidase histochemical staining," *DNA Cell Biol.* 13(7):755-62, 1994.
Wardlaw, "Obesity as a neuroendocrine disease: lessons to be learned from proopiomelanocortin and melanocortin receptor mutations in mice and men," *The Journal of Clinical Endocrinology & Metabolism* 86(4):1442-1446, 2001.
Yoshinaga, et al., "Structural requirements of peptide YY for biological activity at enteric sites," *Am. J. Physiol.* 263:G695-701, 1992.
Young, et al., "Authentic cell-specific and developmentally regulated expression of pro-opiomelanocortin genomic fragments in hypothalamic and hindbrain neurons of transgenic mice," *J. Neurosci.* 18:6631-6640, 1998.

* cited by examiner

Leptin (100nM)
Potential (mV)
Times (s)

Depolarization (mV)
EC50=5.9 nM
log [Leptin (M)]

Voltage (mV)
Net Current (pA)

Leptin (100nM)
IPSC Frequency (Hz)
Times (min)

Leptin (100nM)
Potential (mV)
Times (s)

Leptin (100nM)
Potential (mV)
Times (s)

NPY (100nM)
IPSC Frequency (Hz)
Time (min)
D-Trp8- γMSH (7nM)
IPSC Frequency (Hz)
Time (min)

D-Trp8- γMSH (7nM)
Potential (mV)
Time (s)

POMC
GABA
POMC

Target Site
NPY/AGRP
MC3-R
MC3-R
GABA
Y1-R
Y2-R
MOP-R
MC3-R
Lep-R
Y2-R
Lep-R

● c-Fos ● EGFP ● colocalisation

Firing rate (%)
300
200
100
0
Baseline
PYY3-36
Washout
**
Membrane potential (mV)
10 (S)
Normalised firing rate
1200
900
600
300
-250
0
250
500
750
Time (s)
IPSC frequency (%)
Current (pA)
0.2 (s)
-500

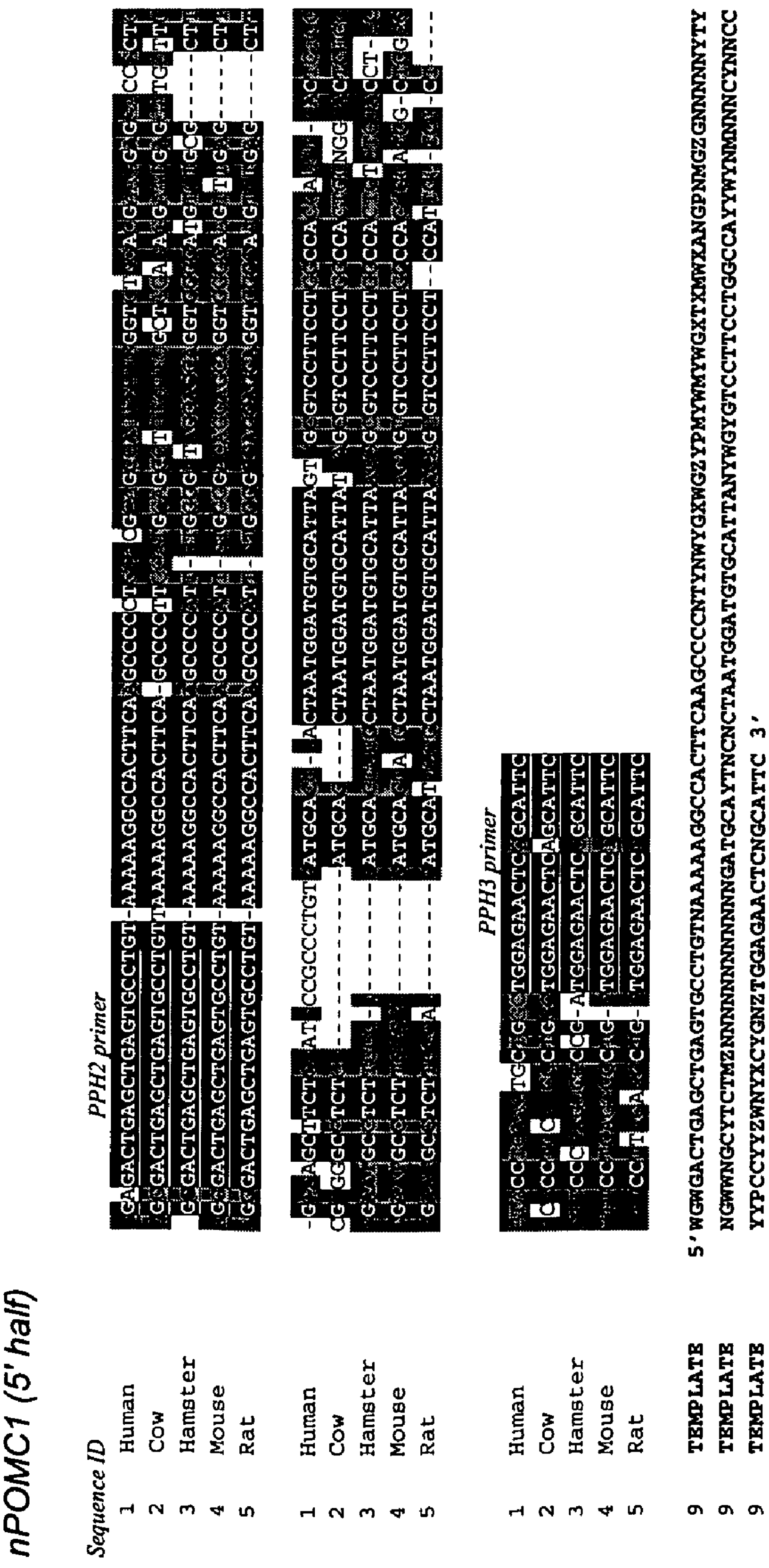

FIG. 10a nPOMC1 (5' half)

*Sequence ID*

[Alignment block with *PPH2 primer* label, showing sequences for:
1 Human
2 Cow
3 Hamster
4 Mouse
5 Rat]

[Second alignment block showing sequences for:
1 Human
2 Cow
3 Hamster
4 Mouse
5 Rat]

[Third alignment block with *PPH3 primer* label, showing sequences for:
1 Human
2 Cow
3 Hamster
4 Mouse
5 Rat]

TEMPLATE 9  5' WGWGACTGAGCTGAGTGCCTGTNAAAAAGGCCACTTCAAGCCCACTTCNCTAATGACAYTNCNCTAATGATGTGCATTANYWGYGTCCTTCCTGGCCAYYWYNMNNCYNNCC

TEMPLATE 9  NGWWNGCYTCTMZNNNNNNNNNGATGCAYTNCNCTAATGATGTGCATTANYWGYGTCCTTCCTGGCCAYYWYNMNNCYNNCC

TEMPLATE 9  YYPCCYYZWNYXCYGNZTGGAGAACTCNGCATTC 3'

FIG. 10b nPOMC1 (3' half)

| Sequence ID | | |
|---|---|---|
| 6 | Human | TTCT-GGAAA...GTAGCAGTCA-TGCTCGAGCCCT ACAA AGGACCATTATCAC CCCTGAGTCA A |
| 7 | Mouse | ...GGAA G GGT AGCAGTCA TG --- CCT A GG GGGCCATT TG C C CTGAGTCA A |
| 8 | Rat | ...GGAA G AGCAGTCA TG --- CCTGA GGG GGCCCATT TG CC C CTGAGTCA A |
| 6 | Human | AT GTGCC CTGGCACC GAGCTC GTCTGGAAAGAGAGGCA CAGGGACGTCATC A CAGAG CTGGTG GT TGTTA TCCA |
| 7 | Mouse | TAGTG C ACTGGCACC GAGCTC GTCTGGA AGGG TCAGGGACGTCATC G AGAG CTGGTG CGT T AC TCCA |
| 8 | Rat | T GTG C CTGGCACC GAGCTC GTCTGGA AGGG TCAGGGACGTCATC C AGAG CTGGTG GT T A ATCCA |
| | | Putative STAT3 binding sites |
| | | TTCCNGGAA |
| | | TTCCNGGAA |
| 6 | Human | CAACAT TTCAGCAAAGAC ACTACTTCCAGGAAGTCTACTTGCAGAGGCCAA CCTTCATT GTGAAAAAAGG CTTG GAT |
| 7 | Mouse | ACAT TTCAGCAAAGAC AC TCCAGGAAGTC A T GA TGC AG CC TCATT TGAAAA AGAG TTG G T |
| 8 | Rat | ACAT TTCAGCAAAGAC AC TCCAGGAAGTC A T GA TGC AG CAA CC TCATT TGAAAA ACCG TTGAG T |
| 6 | Human | AAGGAGTG TTCTAAAAGAATACAT TGGCTCCAG TG CAATATACCCA G TGTAATAA CTCAGGG TAAGAGAGAACCTGCCAT- |
| 7 | Mouse | AAGG G TT AAAG ACA A GGCTC ACA A CCA AA A TGATC -CAGGG-A AGACT- |
| 8 | Rat | AAGG G TT AAAG ACA GGCTC CCA AA A CCA G T T A C -CAGGG-A -AGAGC |
| 6 | Human | TCTCCAT ACTGTCACACAA CTTACAGGC TCTCAC GGT -- CCCAT GAACT |
| 7 | Mouse | T CT A AGCCTT A CA GCCACA T G - TA GCTGC TTG A |
| 8 | Rat | T CT A - CTG TCAA C A ACC CAC TT CCATCATGA CAT |
| 9 | Template | 5' YYYMNGGAAWWGYAGCAGTCANTGNNTGNNNNNNCCTWANNWGGNNNNCCYCAXAAPWGGNCCATTWTGWYCZYCWCTGAGTCAXA |
| 9 | Template | ZTWGTGWCYWCTGGCACCYGAGCTCYGTCTGGAWPWAGYGGYPMCAGGGACGTCATCYWXAGAGYCTGGTGYGPXTXTPAYWTCCA |
| 9 | Template | XWACATYTTCAGCAAAGACPXYACYTCCAGGAAGTCYAYTYMGAYTGCZXAGWZWCAAWCCYTCATTWTGAAAAWAGNGYTTGWGZT |
| 9 | Template | AAGGZWPGXTTXMWAAAGWWYACAPWPGGCTCYWCMWWXAAYAYWCCYAXGYXTNNTWAMCNCAGGGPAZWAGAGNNNNNGNXATN |
| 9 | Template | TMCTWAYWXZXMNXYNYNNZXNCAZWCNNNXKNXNYTXYNNNZYWXXWTNNXPNCNNNWMWNZNMW 3' |

FIG. 11a

SEQUENCE ID NO. 20
"nPOMC 1 element"
Mouse Chromosome 12 nucleotides 3,808,010 - 3,808,587
AGGGACTGAGCTGAGTGCCTGTAAAAAGGCCACTTCAAGCCCCATTGTGGGGACAGCAGCAGGTGGGCAAGTCTGAGCTTTGAATGCCTCTTCCCGTGATGCACTACGCTAATGGATGTGCAT
TAACAGTGTCCTTCCTGGCCACCGCATCGCTCGCCTTTCCTCAGGCCCTGCTGGAGAACTCTGCATTCCTGAGGAAGGGCAGCAGTCAGTGCCTAAAGGCCCCAGAATGGGGCCATTGTGGTC
ATCACTGAGTCACACTAGTGACTACTGGCACCTGAGCTCAGTCTGGAGTAAGTGGTTTCAGGGACGTCATCTGGGAGAGTCTGGTGCGAGTCTAACGTCCAGGACATTTTCAGCAAAGACTGC
ACCTCCAGGAAGTCCATTCTGACTGCCCAGAAACAAACCCTCATTTTGAAAAGAGAGTTTGGGCTAAGGCAAGCTTGGGAGAGGGCACAAAAGGCTCTGCGGAGGAACACGCCTACGCCTTGA
TCCAGGGAACAAGAGTGGGATGTTCTAACAGCCTTGCACCACGCCACGCCACGCCATTGCGATGGCATTAGTGCTGCGTGTAGGA

SEQUENCE ID NO. 21
[redacted]
Human Chromosome 2 nucleotides 2,324,419 - 2,323,806 (REVERSE COMPLEMENT STRAND)
GGAGACTGAGCTGAGTGCCTGTAAAAAGGCCACTTCAAGCCCCCTCCACGCAGCCATTGTTGGGTCTGGAGGAAGGAGGACCGCTCGGAAGCTTCTGAATGCCGCCCTGTGATGCACTCACTA
ATGGATGTGCATTAGTGGCGTCCTTCCTGGCCACCACGTCACTCTCCCTACCTCAACTGCTGGCTGGAGAACTCCGCATTCTTCTGGAAAAGTAGCAGTCATGCTCGAGCCCCTAACAAAGGC
CTGTCCCCCACAAAAGGACCATTATGACCACCGCTGAGTCAGAATGGTGGCCGCTGGCACCTGAGCTCTGTCTGGAAAGAGCGGCAGCAGGGACGTCATCTAGCAGAGCCTGGTGTGTCTGTT
ATGTCCACAACATCTTCAGCAAAGACACTACTTCCAGGAAGTCTACTTGGATTGCAGAGGCGCAAGCCTTCATTGTGAAAAAAGGGCTTGGGATAAGGGAGTGGTTCTAAAAGAATACATGTG
GCTCCACATGGCAATATACCCAGGTGTAATAAGCTCAGGGTAAGAGAGAACCTGCCATTGCTGATGCAGGACTGTGCACACAAACTTACAGGCTCTCTACTGGGGTGTCCCATGGAACTGG

SEQUENCE ID NO. 22
[redacted]
Rat Chromosome 6 nucleotides 1,962,320 - 1,962, 887
AGGGACTGAGCTGAGTGCCTGTAAAAAGGCCACTTCAAGCCCCATTGTGGGGCCAGCAGCAGGTGGGCAAGTCTGAGCTTTGAATGCCTCTTCCCATGATGCATTGCGCTAATGGATGTGCAT
TAACAGTGTCCTTCCTCCATTGCTCTCTTTTCCTTAGACCCTGCTGGAGAACTCTGCATTCCTGAGGAAGAGCAGCAGTCAGTGCCTGAGGGCCTCACAAAGGGCCCATTGTGGTCCTCACTG
AGTCAGACTGGTGACTGCTGGCACCCGAGCTCAGTCTGGAGTAAGTGGTTGCAGGGACGTCATCCGCGAGAGTCTGGTGTGACTCTAATATCCAGGACATCTTCAGCAAAGACTGCACCTCCA
GGAAGTCCATTCTGACTGCCCAGAAACAAACCCTCATTTTGAAAAGAGCGTTTGAGCTAAGGCAAGCTTGGGAAAGGGCACAAGAGGCTCTGCAGAAGAACACGCCTACGCCTTGAGCCAGGG
AACAAGAGCGTGATGTTCTAACGCAGGGCCCTGCGTCACACGGCCTTGCACCACACCATTCCATCATGATGCAATG

FIG. 11b

SEQUENCE ID NO. 23

[redacted]

Mouse Chromosome 12 nucleotides 3,810,499 - 3,810,726
GGCTACTGTGCTAATACATGCATTAGTGGATGAAAGCCGTCTCAAGGGGCTCTTCACCAGGGCCCTTTGGCTGTAATAAAGCAAATTAAAACCCCATCCAAAGGTCAATTGAAATCTCTTTCA
TTCTTCTTCTCCACACAAATTGATTCCTCTTTGCCCTTGAGGTTGCACTGAATGCCATAAAGGGGCCCAACTGTAGCTGGATGGGAACAAGCCTGAAAATGGCT

SEQUENCE ID NO. 24

[redacted]

Human Chromosome 2 nucleotides 2,322,890 - 2,322,659 (REVERSE COMPLEMENT STRAND)
GGCTGCTGCACTAATGCGCGCATTAGTGGATAAAAGCAGTCTCAAGGGTCTCTTCACGAGGTCCCTTTGGCTGGAATAAAGCAAATTAAAACCCCATTCAAAGGTCAATTGAAATCTCTTTCA
TTCCAGTTCTCTGCACAAATTGATTCCTCTTTGCCCTTGAGGTCAAACCGAAGGCTGGTGAAGTAGCCCAGCTGCAGTGCTGCATGAGAGAAGCTCAATGAAAAGGCT

SEQUENCE ID NO. 25

[redacted]

Rat Chromosome 6 nucleotides 1,964,684 - 1,964,909
GGCTGCTGTGCTAATACATGCATTAGTGGATGAAAGCTGTCTCAAGGGGCTCTTCACCGTGGCCCTTTGGCTGTAATAAAGCAAATTAAAACCCCATTCGAAGGTCAATTGAAATCTCTTTCA
TTCCACTTCTCCACACAAATTGATTCCTCTGTGCCCTTGAGGTCACACTGAATGCCATAAAGGGGCCCAGCTGTAGCTGGATGGGACAGCCTGAAAAATTGCT

SEQUENCE ID NO. 26

[redacted]

Mouse Chromosome 12 nucleotides 3,813,451 - 3,813,596
CTGCACCTGCCTTTGTAGCGTACTCACACCCTGGTGACATCTCTTTTCCAATTAAACCCTCCCATGTGAAAAGCTGAGATGACCTCAGCAGAGTGGCCTCAGCCCTGTGCCCACAGCCATCTG
GCATGACTGCAGCCAGGTGCAG

SEQUENCE ID NO. 27

[redacted]

Human Chromosome 2 nucleotides 2,320,149 - 2,320,009
(REVERSE COMPLEMENT STRAND)
CTGCACCTGCCCTTGTAACGCACTCACACCCTGGTGACATCTCTTTTCCAATTAAAACCTCAAAGGTGAAAAGCTGAGATGATGAGAGCAGCCCCAGCCCTACGTCTACAGCCACCTGGCACG
CCCGCAGCCAGGTGCAG

SEQUENCE ID NO. 28

[redacted]

Rat Chromosome 6 nucleotides 1,967,170 - 1,967,309
CTCCACCTGCCTTTGTAACGTACTCACACCTTGGTGACATCTCTTTTCCAATTAAACCCTCCCAGGTGAAAAGCCGGACTGACGGGAGCAGCCCCAGCCCTGTGCCCGCAGCCACCTGGCATG
ACTGCAGCCAGGTGCAG

FIG. 14a

SEQUENCE ID NO. 29

-13kb

GGATCACATCACACAGTCCAGGCTGATCTGGAACTCACGATGTAGCAGAGGGTGGCTTCCAAGTAGTAGCAATCAGCTACCTCAGTTTTCCAACCTGGGACAACAGTCACTTGCCATCCTTAT
TGACTATCTTGGAACGAAATGCATCATACCTATAACGATAGGAGCAATTCTGCAGGGCTGATTTATAAAATGAAGGAATATAGCTGATACTTTGCAAAACAAATAAATAAACAAAATAAAACA
TAACCAAAACGAAAAGAAAAAAAAAAAAAAACCTTTGGAGTCAACCGGCCTTTCCAAGTAAAGGGGTCTGCTAAAGGACCAAGAACAGCCTGCTCTAGTTCTGGCTTCGAGACTTGCTTTCAAT
TCACAACAAGATTTTGGTATACAGAGAGAGCAATGGCTCTTAGTTCTGTTGTGGAGCAGGTCACGATGAGCTGCTCTGCCGGGGCCCAGTGTCATTCACCTGGGACAGCAGGACAGAAGCGG
TCTGAACCTCAATTCCCGCTGCTTGATTTGAAGTCCGGGTTGCTCCGTTCCTTTGTGCAGCAGGCATGAAAACAACAGAGGACACCAGGCGGCAGGGACAGGCACTCAGCTGACTGCCTGTAA
AAAGGCCACTTCAAGCCCCCATTGTGCCCACAGCACCACGGTGCCCAAGTCTCAGCTTTGAATGCCCTCTTCCCCGTCATGCACTACCGCTAATCCATGTGCATTAACACTGTCCTTCCTGCCCACCC
CATGCCTGGCCTTTCCTCAGGCCCTGCTGCAGAACTCTGCATTCCTCAGGAACGGCCAGCCACTCAGTGCCCTAAAGGCCCCCAGAATGCGCCCCATTGTCGTCATCACTCAGTCACACTAGTCACTA
CTGCCACCTGAGCTCACTCTGGACTAACTGCCTTTCAGCCACGTCATCTGCCAGAGTCTGGTGCCAGTCTAACCGTCCAGGACATTTTCAGCAAAGACTGCACCTCCAGGAAGTCCATTCTGACT
GCCCAGAAACAAACCCTCATTTTGAAAAGAGAGTTTGCGCTAACGCAAGCTTGCGACAGCGCCACAAAAGCCTGTGCCCGAGGAACACCGCCTACGCCTTCATCCAGGGAACAAGAGTGCGCATGTT
CTAACAGCCCTTGCCACCACGGCCACCCCACGGCCATTGCCCATGCCATTAGTGCCTGCCGTGTAGGAGTGATGCAGAGGCTGTGACCCAGGCTGCCCGGCCGTCCACAAGATGCTTTTTTTTTTTTTT
TTTTTTTTTTGGNTTTCTGAGACAGGGTTTCTCTGTGTAGCTCTGGCTGTCCTGGAACTCACTCTGTANACCAGGCTGGCCTCGAACTCAAATCTGCCTGCCTCTGCCTCCTGAGTGCTGGGA
TCAAAGGCGTGCTCCACCACGCCCGGCTCACAAAATGCTTTTGCCAGAAGTTTCCGTTACTTAGCAAGAGTTGCCCTTGCCTCCTGCTTCTAGTTTTCTCTGGGATTAGGCAGAAAGATCAAT
CGTTTGCCCGTATTAGGGGACTTTAACATATACAAAGGAAAACAGAGAGACAGATGGACAAATGTCTGACTCCTTGGCTCAGCGCTCAGAGGGCTTTATTGGTCACATTTTGCCTGCCTTCCT
CCCTCCCTCCCCCTTCTTTCCTTCCTCTCCTCTCCTCTCCTCTCCTCTCCTCTCCCTCTCATCTCCTCTCCTCTCCTCTCCTNTCCTCTCCTNTCCTCTCCTCTCCTCTCCTCCCTCCCTTCT
TCATGTACATCAAGATGATCTTGAAATCACTATATAGTTGAAGAGCCTGTAGCTGGTCTTTGCTACTTTGTGGGTTCTCTTTCCCACCTTTTATTCCCCCTGCCAGGTTTCACCCCCATCACA
GGTAGGAGAGAAAGAAGGATAGAGGGGAAGAGAGATATGAGATACCCCACCTAATTTCTTTCCTTTTGTTTCTTCTTTGACCATGGCTACTAATAAACCACAACCATCCCCCCTAAACAACCA
CCAAGCACCAAGGCTCACCCCTTTCTCGGGGCCCTAGCACTTACATGCCTCTGAAAAGTTCCTGTAACTTTTATATGTCACACAGTGGCAGAACCTATCTGTAGTTGGCTTTGCTAGAGGAGA
GGGCAAATCNCAGTCAACTGTGGTGAATAGTCCGAAGCGTCCTCAGGTCTCCATATCTGGGATTAAAATAAAAAACATTTTCTTGCCGGACAGTGGTGATGCACACCTTTAATCCAGCACTTG
GGAGGCAGAGGCAGGTGGATTTTTGAGTTCGAGGCCAGCCTGGTCTACAAAGTGAGTTCCAGGACAGCCAGGACTACACAGAGAAACCCTGTCTCGAAAAACCAAAAAACCAAAAACAGAAGA
AAGAAAGAAAGAAAGAAAGAAAGAAAGAAAGAAAGAAAGAAAGAAAGAAAGAAAGAAAGAAAGGAAGGAAGGAAGGAAGGAAGAAAGAAAGGAAAAGAAAAGAAAGAGAAAGAGAAAGAGAAA
GAAAGAAGAAAAGGAAAGAAAAAACCTTCTTGTAATATTCTGTTTATTTAAAGAAATCCAAATTCCAGAATGTCACTCCAAGAGTCCTAGAGTAGGAGCCACCTCACTTGGTTTTATGCAGC
GCTGAGGATTGAACCCAGAATTCTGTGTGCTAGGCAAGAGATGCCAGCTAGACCTTACTCCCAGTCTCCTCTCACCTCTTCCCCCAGCTTCCTCTTTCCCTCCCCCTCTTCCCCCCCCCCTCC
CTTTTTCTGTAAGGTCTTGCTATGTAGTTCAGATTAGTCTATAACTCACAGTGTTGGGATTACAGGCACGAGTCACCACATTCAACTCCTACCATTTCTTTAGAGTTATATTAAAGATGATTT
TAATCCATAGAACATCATGCCTGGAATGGACCAAAGACCATGGAACCCTGTTTTTTACGATAGGGAGATAGGACAAGGTAGAGCAAGAACCCAGGTTATCTTGCCCTCCCCCTCCCCAAATCC
CTCCCCCTGCCTTCTCCCTTCTCTCTCCCACACTCTGATTTTACTTGGGCCTCAGGGTACTGAAAGCTAATTCCAGGGAGAGGCCGTGCCCTGGCTTTGGGCCTCTGGCCTGGACCCTTCTGT
TCTGTGGGGCATGCAGTCCTTGCAGGCTGCGGGTCGGCTACTGTGCCTAATACATGCCATTAGTGCATGAAAGCCGTCTCAAGCGGCTCTTCACCAGGGCCCTTTGGCTGTAATAAAGCAAATTAA
AACCCCATCCAAAGGTCAATTGAAATCTCTTTCATTCTTCTTCTCCACACAAATTGATTCCTCTTTGCCCCTTCAGGTTGCACTGAATGCCATAAAGCGGCCCAACTGTAGCTGGATGCCAACA
AGCCTGAAAATGCCTTCCCTGGGGCTTTGGCGGGGATGAGAGGCAGNGGCTCCTACCTCCCCCCTTGCTCCCTCCACCCCCACACCATCGGGTCACCAGGGACACTCTCCTTCAGTGTGCTCT
TGGCTTCTGATCCCATCTTTGGATTCTTCCCCCCATCCACCAGGCTGTCCTCAGAGGAGACCCAATTCCCTTTTACTGAGTTGCCCAGCCTAACCTCAGCCTTGAGAGGCCTCTGCCTCAGCA
TCCTGGGTGCTGGGATGGCAGACATGAACTGTGCATCGCAAATGGACCCAGTGTTTACACTGATAATATTTTTGTGTAGTCCTGGGTGTTCTAGAATTTGCACTATAGAATTCAGAGATCCTC
TGCCTCTGCCTCTGGAGTGCTGGATTAAAGGTGTGCAGTGACAATCTTAACAGCGACTGGAATTTCTACAATCTGCTTGAACTCTCACCAGTCAGGTGACGTAGGCCTTTGAGAGGCTCAGAG
AGGTTAAGTAACTTACCCATGGTCACAGAGCTCATGATTTTCTCCCTCAAACCATTTATCCCTCAGCCTCTCTGTGACAGCCCAGTGTGGTACAGCCAGCTGCCAGGCGTCCTGAGAGAACCT
TTAGTCCTCCGAGTGGCTGTGCAGAAATGGCCAGAGGCACTATGCAAGGATGCCTTCTGGATTTTGTCTTTGGCTTGGATCC

-9 kb end (*BamHI*)

FIG. 14b

SEQUENCE ID NO. 30

-11.5 kb

GGCATTATTTACATTCCCATCAGCAGCAAAATACCCTTTCAAGAGTAAATAAATAAGTAGTGAGACCTTATTTATTATCTTGAAATGAAATTCATTGATAATATAACCTTCTCATGTTCATAAT
ACATAGAAAAATAACTTCAACCTAAAGGTTGAACGATAATATAAAGGATAAATTAAAAGAACATAATTTATACATGTTTTTGTTTTTTGAGACAGAGTCTCACTCACTGTGTCACCCAGGCTGGA
GTGCAGAGGCACAATCTTGGCTCACTGCAACTTCCGCCTCCCGGGTTCAAGAGATTCTCCTGCCTCAGCCTCCTGAGCAGCTGGGACTACAGGCACACACCACCACACTCTGCTAATTTTTTGTA
TTTTTAGTAGAGATGAGGTTTTGCCATGTTGGACAGGCTGGTCTCAAACTCCTGACCTCAAGCGATCCACCCACCTTGGCATCCCAAAGTTTTGGGATTATAGGTGTGAGCCACCATGCCCAGCG
AATACATGTTTTTTGAAATGAGATGTTGAAGTCAGAGACTGGCCTTCTCAGGCGGATTAGACCTGGTCTGGAAGCATTTCCCCTAAGGGGTCTGCCAAAGGCTCCAGCCCCAGCCCCTCAATGGC
ACCAAGAACAGCTGCCTAGGGGGATGCTGGGAAAGGAATCACTTTCAACTGGACATAAAGGCTTTGGACAGCGTGTTAAAAACAAACCAAACTACCTTTCAAACCCATTTCAGGAGTCGTTGCAC
CCTTCCCATCACACACACACACACATGCACACACACATACACGTGCATGCACATGCACAGACACACACAGAGTCATGGGCTCTTTGAGCTGCTGCATAGCAGGTCACTGTGCACCAGCTCTGCCC
AGCCTGGTGTCCCTCTCCTGGGGCAATGGGACTGAGGGCACAGTGGGGGCTCTCCGGGCCGCAGGTGGGCTGCCTGGATTCGCTGTCCTGGCTGCTCCATTCCTTTGAGCAGCAGGCATGGAAAT
GGAAGATGGGTACCTAACGGGGGCGGGGGCTGGAGAGCGAGACTGAGCTGAGTGCCCTGTAAAAAGCCCACTTCAAGCCCCCTCCACCGCAGCCATTGTTTGCCGTCTCCACGAAGCAGCACCCCTCCG
AAGCTTCTGAATGCCCCCCTGTGATGCACTCACTAATGCATGTGCATTAGTGCCGTCCTTCCTCCCCACCACGTCACTCTCCCTACCTCAACTCCTCCCTCCACAACTCCCCATTCTTCTCCAAA
AGTAGCAGTCATCCTCGAGCCCCTAACAAACGCCTGTCCCCCACAAAAGCACCATTATCACCACCCCTGAGTCAGAATCCTCGCCCCCTGGCACCTGAGCTCTGTCTGCAAAGACCCCCAGCACCC
AGGTCATCTACCAGAGCCTGGTGTGTCTGTTATGTCCACAACATCTTCAGCAAAGACACTACTTCCAGCAAGTCTACTTGCATTGCAGACCCCCAACCCTTCATTGTCAAAAAACCGCTTGCCAT
AAGGCAGTCCTTCTAAAAGAATACATGTGCCTCCACATGCCAATATACCCAGGTCTAATAAGCTCAGGGTAAGAGACAACCTGCCCATTGCTGATGCAGCACTGTGCACACAAACTTACAGCCTCT
CTACTCGGGTGTCCCATGGAACTCGCTCTGTGTGAGGAGCGGCTGCAGAGGGCTCTTTGATCAGGGCTGGCTTTCCACAGGCCACTTGGACCCCATGGGTGGCTGCCTGCAGCAGGAGTGCTGGT
AATTAGTGGCCCCATTAGTTTCCTCTGGGATTCAGAGTGAACAGAGCAGAGAACTGGCCTGCCCATGTGTGCAGACTGGAGCAGATTCTCAGAGAGAAACAGGACACGAGAAAGGCCCAAGAGAC
AGAAGGACAGAGCTTACCTCCTCAGCCCAGAGGACTCAGCTGTGCCCATTAGGGGCCACGTTCTGTAAGACTATTGTTTGTTTGTTTTTAATCACAGAGCTTGACTCTAGATCTGAGCCTAGAA
TCATAGAATGACAGGCCTGAAACGGACCACATCCTCCCCGCCCCCATTGTTCAAATGAGGGGGCTGAGGCCTGGAGGTGGGGTGGGGGTGGGGGAGTGACTGACCCAGGTCCCTGTGTCTGCTG
GCCACAGAGCTGGGGCTAGAACCCAGGTCACCTCACCCCCTCCCACTGCTTCTTCCTCCACTCTATTTTTTTTTTTTTCTGAGGCAGGGTTTGGCTCTGTTGCCCAGGCTGAAGTGCAGTGGCAT
GATCATGGCTCACTGCAGCCTCCACCTCCCAGGTTCAAGTGATCCTCCCACCTCAGCCTCCTAAGGAGCTGGGACTACAGGCGTGTGCCACCATGCCCGGCTAATTTTTGTATGTGTGTGTATAT
ACGTGTATATATATATATATATTTGTAGAAATGGGGTTCCACCATATTACCTAGGCCCTTCCTCCACTCTTGACTCTGCTTTGGACCCTGAGGGTGCTGACAACCTGCTCTAGGGAGGGGCATGG
ACTCTGGCCCTCCCCACTGTGCTCTGCGGCACCCAGACCATGCAGACCTTGGCCCAGGCTGCTGCACTAATGCGCGCCATTAGTGCATAAAAGCAGTCTCAAGGGTCTCTTCACCAGCTCCCTTTG
GCTGGAATAAAGCAAATTAAAACCCCATTCAAAGGTCAATTCAAATCTCTTTCATTCCAGTTCTCTCCACAAATTCATTCCTCTTTGCCCTTCAGGTCAAACCCAAGGCTGGTCAAGTAGCCCAG
CTGCAGTGCTGCATCAGAGAAGCTCAATGAAAACCCTGAGACTGGGGAGGGCGTGTTGCAGGGGTGAAGCGGGGCAGTGGGATCCGCCTGAATTGTAGGGCCATCTGGGGCACCAGTAACCCTCT
CCTCTGCAGTGCTTCAGGCTTCAGGCCCTTTTCTGGAGGCAGCTCCCTGTCTGCCCTGCAAACCACATCAGGCTCCCCTCAGAGGGATGCTTAATTAGGGTTTCTATTGACAATTGTGGGTGCCA
AGAGAAAATTTCCTTCCTTCACTCTGCCCTCTGAAGTTTTGTTGAAAATGAACTGCTAATAGACAGATTAATAGGGGAACAAGACATACAAATTAATTTCATGTGTATAGCATAGCAGAATGGTG
GGAGAATGATTACCCAGTAACTCAATGAGGTCCAGATGCCTGCAGATATTTCTTGATAGGGGAAGGGAAAATGAGGGGCATAGGAGTAAATGATTTTCTGGGAAAGTGAATGCGCCCGAGGAACA
ATGGCCTGGGACAAAGTTCTTCTCTGTTCTTTGGGTAGGTGGTGTGAAGGTGAGAAGCAGAAAGTCATTGTGAACGCAGCCTGTCTTATTATGCAGGTAACCCCCCTAGGCTATCTCTTGGAGTT
GCCCTCAGAAAAATGCAAGAAAAGTCTGTCTGGAGGCGGTGATGATCCGTCTCTTCTCAGGTGGTTAATCTTTCTTTCCTGGTTATTTGATGAGATTCCTATGAAGGGAGGCTTCAGGCAATTGT
ATTTCTTTTAGAAAGAAGTTTCCTTAGTCAGATATGGAAATGCCAAAGACAGTACCTTCTGGTGTTTTGGAAAAAATCAGAGAGACAGGGAGTGAGGGGAAGGTCAGGGCGAGATTTTGAAGGTT
CTTCAAAGGAACTGAAGCTGCTTCTTTAGTTCCATATTTTGGGGTATAATTTTCTGAGCCCCAGTGCAATTTTAGCGGTAGTTAGGATTTCTTGAAAGTGCTCACGATTCTTGAATGCCCACATA
AAGGGGAAGATACTGGGCTATTTCTCATTCAGACACAATGAAGAGGAGGCACTTCCCTGTTTCAGGTTCATGTGTCCTACAGAGGGAGTACGGAGATGTTACTGGAAAGGAATCCCAATCCGGAC
CCCAAAAGAGGGTCCTTGGATTTCACGCAAAAAAGAATTCTGGGCAAGTCCATAGATTAAAGTGAAAGCAAGTTTATTTATTAGGAAAGTAAAGGAATGAAAGAATGGCTACTCCATAGGCAGAG
CGACCTGGAGGGCTGCTGGTTAACTTTTTTTTTTTTTTTCTGAGACAGAGTCTTACTCTGTTGCCCAGGCTGGAGTGCAGTGGCGTGATCTCAGCTCACTGCAACCTCCGTCTCCCAGGCTCAAG
CAATTCTCTACCTCAGCCTCCCAAGTAGCTGGGATTACAGGCGTCTGCCACCACGCCCGGCTAATTTTTGTATTTTTAGTAGAGACAGAGTTTCACCATCTTGGACAGGCTGGTCTTGAACTCCT
GACCTCGTGATCCACCTGCCACGACCTCCCAAAGTGCTGGGATTACAGGCTTGAGCCACCACGCCTGGCCTGGTTAACTATTTTTATGGTTATTTCTTGATGGTATGCTAAACAAGGGGTGGATT
ATTTATGTTTCCCCTTTTAGACCATATAGGGTGACTTCCTGACATTGCCATGGCATCTGTAAACTGTCATGGCGCTGGTGGGAGTGTAGCAGTGAGGACCAGAGGTCACTCTCTCAGTGGCCATC

SEQUENCE ID NO. 31

-13.8 kb

ATTTGTGTGTTGATTGAATGTATGCTCTGTGTGGATAGGTTCCTGTGGAGGCCAGAAGAGAGCATCAGGCCCTTTGCAACTGGAGTTCCAGTCTGGCTACTTCAGTTGTCCAACCTGGGACA
AGAGTTATTTGCCCCCATGCCCATCCTTGACTATTTTTTTTTTTTTTTTGGTTCTTTTTTTCAGAGCTGGGGACCGAACCCAGGGCCTTGCGCTTCCTAGGTAAGCGCTCTACCACTGAGCTA
AATCCCCAGCCCCCATCCTTGACTATTGATCTATTGGCTATGTTGGAATGAAATGCATCGTGTCTATACTGATAGAAGCAATCCTGCAGGGCTGATTTATAAAATAAAAGAATAACTGATAC
TTTGCCAAACAAACAAACAAAACCTTTGGAGTCAACTGGCTTTTTCAAATAAGGGGCTAAAGGACCAAGAACAGCTGCCCCCGGGAGCTGGCTTACAGACTAGATGCTATCAATTCTCAAGA
TTTTGGTACATGCAGAGAGCATTGGGCTCTTGGTTCTGTTGTGGAGCAGGTCACACTGAGCTGCCTCAGCTGGGGCCCAGTGTCATTCACCCCGGACAGCAGGAGGGAGGCAGCTCTGAACC
TCAGTTTGGGCTGCTTGATTTGAAGTCCAGGCTGCACCGTACCTTTGAGCAGCAGGCATGAGAATAGCAGAGGACCCTAGGCAGCTGGGACAGAGACACGGACTCAGCTGAGTGCCCTGTAAA
AAGGCCACTTCAAGCCCCCATTCTGCCCCCCAGCAGCAGGTGCCCCAAGTCTGAGCTTTGAATGCCCTCTTCCCATCATGCATTGCCCTAATCGGATGTGCATTAACACTGTCCTTCCTCCATTGCT
TTCTTTTCCTTAGACCCTGCTCCAGAACTCTGCATTCCTGAGGAAGACCAGCAGTCAGTGCCCTGAGCCCCTCACAAAGCCCCCATTTGTCCGTCCTCACTCAGTCACACTCCTGACTCCTCCCA
CCCCAGCTCAGTTCTGGAGTAACTGGTTCCACCGACCGTCATCCGGCCACAGTCTGGTGTCACTCTAATATCCAGGACATCTTCAGCCAAAGACTGCCACCTCCAGGAAGTCCATTCTGACTGCCCCA
CAAACAAACCCTCATTTTGAAAACAGCCGTTTGACCTAAGCCAAGCCTTCCGAAACCCCACAAGACAGCCTCTGCAGAAGAACACCCCCTACCGCCTTGAGCCCACGGAACAAGACCGTCATGTTCTAA
CGCAGGGCCCCTGCCGTCACACCCCCCTTGCACCACACCCATTCCATCATGATGCCAATGGGCGCTGCGTGTAGGAGTGATGCAGACAGAGGTTGTGACCCAGGCTGGCCGGCCATCCACCAAATTC
TTTTGCCAGAAGTTTTGGTACTTAACAAGAGGTCTGTCTTGGTTCTAGTTTTCTCTGGGATTAAGCAGAAAGATCGTTGGCCAGCCCATTTGAGGAGACTTTAGCAGATACAAAGGAAAACA
GAGACAGATGGACAAATGTCTAACTCCTTGGCTCAGAGCTCAGACAGCTTTGTTGTGTCCATTGACCATATTTTGTCTTCCCTCCTATCTCATGTAGGCCAAGGCCAAGATGACCTTGAAGT
CACTATATAGTTGAAGACATTTGTGAACTCTTCACTCTTCCGGTACCCATTTCAAGAGCCTGAAGCTGGTCTTTGCTACTTTGTGGGTTCTTTTTTTTTTTTCTAAAAAAGATTTATTCATT
TGTTATATATAAGTGCACTGTAGCTGTCTTCGGACACACCAGAAGAGGTCATCTGATCTTATTACAGATGGTTGTGAGCCACCATGTGGTTGCTGGGATTTTTTTTTTGTTTGTTTGTTTGT
TTCTTTTTCTTTTTTCTTTTTTTCGGAGCTGGGGACCGAACCCAGGGCCTTGCGCTTGCTAGGCAAACCCTCTACCACTGAACTAAATCCCCAACCCCCGGTTGCTGGGATTTGAACTCAGG
AACTCTGGAAGAACAGTCAGTGCTCTTAACCCCTGAGCTATCTCTCCAGCCCAACTTTGTAGATTCTTTTTCCCACCTTTAATTCCCTCCCTGCCAGGTTTCACCCCCTATCACTAGATAGA
AGAGAAAGAAGGATGGGGGGGGGATGAGATCCCCCACCTAATTTCTTTCCTTTTGTTTCTTCTTCTTTTTTTTTCCGGAGCTGAGGATCAAACTTAGGGCCTTGCGCTTGCTAGGCAAACGC
TCTACCACTGAGCTAAATCCCCAACCCCTTTTGTTTCTTCTTTGAGCACGGCTACTAACAAACCACAACCAATTCCATAAACAACCACCAACCTCACCTCTCTCTTGGGGCCCTAGCACTTA
CATACCCTCTGAAAAGTTCCCATAATTCTCAATGTCACACAATGGCAGAAACTATCGTAGCTGGCAAAACCACACCTCTGCTGGAGCAAGAGGCAAATCTTAGTGAGTTGTTTCAAACAATC
CGAAACGTCCTTGTATCTCCATATGTGGGATTAAAATGAAAACATTTTTCTATAATGTTTCTGTGCTTTTTTAAAAAGAAACTAAAATTCCAGAATTATCACTACAAGAGTCCTAGAGTTTC
AGAGGTGGACCACCTCACCTGGCTCCATGCAGTGCTGAGGACTGAACCTAGAGTTCTGTGTACTAGGTAAAAAACGCCAACTGGACCATGCTCCCAGTTTCTTCTCATCTCTTTCCCCCTCT
CCTTTTCCCCCACCCCCTCCCTCCCCTCCACCCCTTTTCTGTAAGGTCTTGCTATGTAGCTCAGATTAGCCTTGAACTCACAGCAGTCCTCCTACCCAAGCCTCTCTCAAGGGTTGGCGTTA
CGGGCAGAAGCCACCACATTCAGCCACCATCATTTCTTCAGAGTCACATTTTAGAGCTGATTTTAATCCATAGAATGTAATGCCTGGAAGGATCAAAGCCACGCATGGAACCCTGCTTGCGC
GCACTTCTCCCTCCCACACTCTGACTTTACTTGGGCCTCAGGGTACTGAAAGCCTGTCCCAGGGAGAGGCCATGCCCTAGCTTTGGGCCTCTAGCCTGGACCCTTCTGTTCTGTAGGGCATG
CAGTCCTTGTAGGCTGTGGTGGGCTGCTGTGCTAATACATGCATTAGTCGATGAAAGCTGTCTCAAGCCGCTCTTCACCGTGCCCCTTTGGCTGTAATAAACCAAATTAAAACCCCATTCCA
ACGTCAATTCAAATCTCTTTCATTCCACTTCTCCACACAAATTGATTCCTCTGTGCCCTTCAGGTCACACTCAATCCCATAAACCCCCCCACCTCTAGCTGCATCCGACACCCTGAAAAATT
GCTTCCCCTGGGGTTTCGGCAGGGACGAGGGTCAGTGGATCCTCCCCTTTCCCTAGAGCATCTGGGGCACCAGGGACACTCTCCTTCAGCATGCTCATGGCTTCAGAACCCATCTGTGGATT
CTCCCCTTTCCCTAGAGCATCTGGGGCACCAGGGACACTCTCCTTCAGCATGCTCATGGCTTCAGAACCCATCTGTGGATTCTTCCCTCAGTCCACCAGGCTGTCCTCAAAGGAGGCCCAAT
GCCCTTTTACTAAGTTGCCCAGCCTAACCTCAACCTTGAGAGGTCCTTGCCTCAGCATCCTGGGTGCTGGGATGGCAGACGTGAACTGTGCATAGCAAGTGGACCCAGTGTTTGCACTGGTA
ATCTTTTTGTGTAGCCCTGGCTGTTCTAGAATTTGCACTACAGAATTCAGAGACTCACCCGCCTCTGCCTCAGGAGTGCTGGGATCAAAGGTGTGCGTGCGTGCGAAGTCTTAACAGCGATT
GGAACTTCTGCAATCTGCTTGACCCCTCACCAGTGAGGTGATGTGGGCCTTTGAGAAGCTCAGAGAGGTTAAGTAACTGCTCATGCTCACTGGGTTCATGCTTTCACCCCTCAGCCTTTCCC
ACATCCCAGTGTGGTGCAGCCAGCTGCTGGGCATCCTGAGAAATTTCAGAACCTTTAGTCTTCGAGTGGCTCTGCAAAAAATGGCCAGAGGCGCCACGCATGGATGCCTTCTGGATCTTGTCT
TTGGCTTGGACCC

SEQUENCE ID NO. 32
-9 kb

AGCATGGCTCCGTTTTGTACTTGACATTGTAAGGGAAGAGAACTCATTATGATCAACTGATATGTTCATTTGAGACAGATCCTTGTAAGTGACAGAGAGAAAAGTAAGGCCTGGGGTGTGGTTCAGTGGCAGATTACCTGG
TTAGTGTGTGAGACCCTGGGTTTGATCCCTGTACTGGCTGGTTTTGTGTCAACTTGACACAGCTGGAGTTATCACAGAGAAAGGAGCTTCAGTTGAGGAAATGCCTCCACGAGATCCAGCTGTAAGGCAGTTTCTCAATTA
GTGATCAAGGGGGAAAGGCCTCTTGTGGGTGGTGCCATCCCTGGGCTGGTAGTCTTGGGTTCTATAAGAGAGCAGGCTGAGCAAGCCAGGGGAGGCAAGCCAGTAAAGAACATCCCTCCATAGCCTCTGCATCAGCTCCTG
CTTCCTGACCTGCTTGCGTTCCAGTCCTGACTTCCTTTGGTGATGAACAGCAATGTGGAAGTGTAAGCTGAATAAACCCCTTTCCTCCCCAACCTGCTTCTTGGTCATGATGTTTGTGCAGAAATAAAAACCCTGACTAAGA
CAATCCCCAATGAGAGAGAGAGAGAGAGAGAGATAGATTGATTTTTTTGTGAGAACCCCCCAAGAGAACAAGATAAGATTCTTGTAGTTTCAGTTTTCTTCAAAACACACACTTGTTCTTGGACTGGACTACGTTCCTGGG
TGTGTACTGGACAGGAGTGAGTTTACTTCAGAGTATTCATTACAAGTGGCCACAATTGGTTTATACGACTCCTTGGGAAAAGGTTTGCCATTGCAGCTTGGCCTCCATGTGCAGCGTGCCCACCATGTGCAGTCTTCCCTT
GTGACTGCACACTTTACTCATGTAACTCCTCCTAACCCTCAGATCATAAACTAGCTGAGGCTCTGACTAAAGTTGGCTATTACGTGAGACTTTAGTGCTCTGTTCTCCCAGGTCCCACCTCCTCTAGGGTAGAGGAGTATG
TATATTCTGTATCTAGGAAATAAGAAGTTCTCAGAATAATAGCTTCAATTCCAGTTTATATACAAAACCTTCAACTTTTATTTATTTATTTATTTATTTATTTATTTAAATATAAAAACAGGATCTTGTGCTGGTCTAGAA
CGTGAGACACAGACCAGGCTGGTCTCCAACTCACAGATCTGTCTCTGCCTCTTAAGTACTTGGAGTAAGGTGTGTGCCACCACATCTGGTGTCTTAACTCCACTCTTAAAAGCTGACCAGCTTCTTTTCTCCACACACAGA
ATCCATCTTATTGTAAGATCTCATTCAGGCCCTTTTCTGACCCTTCCTATCCAGGGCCCCAGAGTGTATCTCTGGCCCTGGAGCTGCTGGGTGGCACACAGCCTGCTTTCTCATGGTGCATGCGCCCTATATCCCACATCG
TGTGCCCACCCGTGGGCTTCTCCCTTCTTTCCCAACATCAACACAATCAGCACCGGGAGAAGCAGGTGCTGGGTTAGTTTCCAGATGGACCTGAGGGAGATGGGAAAGCCACCTTCTGCTCTAGCCTCTTTGGTCACCAAG
GGCAGCATAGAAAGGAACTTATGCTAAGGCGAAGGCAGGCTCCTTGTCTCTTAGTATCCTCTTTCTCCTCTCACAAATAGCCAGAAATTTGCTCTGTGCTGTGCCCTTGGCACCAATCCAGCCTTTGGGGGCCTTTACTCA
AACAGCAATGGAAGCTGTATTTCTGTCAGGGGGCCCTGGAGGCCACAGTGTGCTCCTACTTTAGGGCAGCTACTTCAGTGTTTCCATGGAGATCAGGGGTCAGGGCTGAGCTGAGCTTGCTTGCTCCCCCCCTCAGAAAT
CAGGGAACCCAGCCTCCCAAACATAGCTGGGTAGTAGTCTCATCCCCATGACCTTTCTCCTGGTGAGGTGACCCCTAGTGCTCAGCCCCAGTGGGGAGGCTGAGAGTCAGGCCATCTTCATGTGTCCGGTGTTGGGTTCTC
TGCCATCTGGTCCTCCTCCGAGTCCCCCTCCGTACCCCTTCTAGCCCTTACCTCCCATAAGGAGGCCATCTTGCCACCTGCCCTTTGTAGCCTACTCACACCCTGGTGACATCTCTTTTCCAATTAAACCCTCCCATCTGAA
AAGCTGAGATGAGCTCAGCAGACTGGCCTCAGCCCTGTGCCCACAGCCATCTGGCATGACTGCAGCCCAGGTGCAGAACTCCCAGGAGCCTTTCCCATGCAGGTCACAAGACTCAGAAGCCCTTCCCGGCAGTCTCTCCCTC
TCCCCTTCCCTCCCTCCATCTCTCCTTTCTTCCTTCCACCCTCTGCCTTCCTGCCAGCATTTTGATGGCATCGAGGACAAAGCTTCCCACTTGGCTCCAGGCCCTGCTCTGAGAACTTATTGAGTTCTAACACATGGAGGT
AGCAGTTGATCCAAACAAACTGGTAAAGAACTTTGTGAACCTTCGAAACACATATGCAGCAAGCAAGGACAGTGCTCGAATCTCCTCCGAGTTGTTTTAGGGAAATGAAAGCTAAAGGCCCGGGGATCATGCCAGGCAGC
AAAGTTGCATCCTGAAGGTTCTGGAACACAGGCCAGGCTTTACCCCAACATTTCCTCTGACTGGAACTCCTGCATAGTTCCTGAACCCCCTTTTTGAGTAGGCTGGTCTCTGTTTATCCCTCACCTGTGCAGTGAGTGTGT
GCAGGGTGTTGGGTGAAGGGAAACTCTCTTCAATGTTAAACTTCTTTAGGTTCAGAAGCACATACAGAGAATTCCATAGAGATGGAAAGAGGGGATCCCAGGAGCCCTTACACCCACCATCTCTCACACTTGAGCGTTTTC
AGCCCAGGATCCATAACTGTGGATAACTAGCTTCAGGAGCCATCATCCTCCTCAGGCTCCAAGCTGCCCATGGTGGAGCAGGGACCTGATGCCTGAACCCTACTCTCAGTGCAGATACCTGAGCAGATTAAATGCTGTTCC
TGCAGACCTCTCTCTCTCTCTCTCTCTCTCTCTCCCTCTCTCTCTCTCTCCTAGATTTATTTTTTATGTGTAAGGTACTGGTTAGTTCATATTGTTGTCTAGATTATTTATTATTATATGTAAATACACTGTAGCGGCC
TTCAGACCCGCATCAGATCTCATTACAGATGATTGTGAGCCACCATGTGGTTTCTGGGATTTGAACTCAGGACCTTTGGAAGAAGAGTCAGTGTTCTTAACCACAAAGCCATCTCTCCAGCCCTGCAGACCTCTTAACACT
GGGGTGGGCTGTGACTCACCTAGATAACCAGAGCAGCCATCATTTAATGCTTGGGTACATTTTTATCTTTGTTTCTGCTTCTATCCACACCTTCACCCATATTTATACCTACATCTTTTATGTCCCCCATTTAACAGTACA
CCGTAGCTATTTCTGTTGAAGAATAAATAGCCATATTCTTTTTTAAAGAAGATTTATTCTTATAATTTTTAATCATGTGTGTACCTGTGTGTGAGTTTGTGCACACGAGTGCAGGGGTCTACGGAAGTTGGATGCTTTGGA
TACCTTGGAGCTGGAGCTACAGGCAGCTGTGAACTGCCTGGTGTGGTGCTGCCTAACGTGGGTCCCAGCAAGAACAGTGCGTGCTCTTATCTGCAGAGCGGTCTTTCCAGCTCCTGTTGTTATTTTGGAGAGTCACAGAAT
ATTCCACTGTATGACGTCACTATAATTCTCATAACTGTATCTTAGGATTGACTTTATTTTATTGTTGCTATAACTGACATATGAAGTCTTGAAGAAAATTTAGTGCTAAATAGTTTTCTTGGGATAAATATTAGGACATGC
TAGGTCAGAAGTTTAAAGACTTGACATAAAGAAAACCCATCCATCCTCCTCTGGTTTATCCTACCAGCCTATTTAAATCTTAGAGCTCCTCCTCTTCCCATTTCACCCTTATCCTGTTAGATCAGAAGCCCCCACCCACCCC
ACCCCACTGCAGCTGTGTTCAAGGATCAGCTTCAGTTTTGGATCCCATCTCTGGTCTGCTTAAGGCGTAGAGTACTTGGCTGGGCTTGGTGGTGCACACCTTTAATCCCAGCACTTGGGCAGCAGAGGCAGCAGTAGATCT
CTGAGTTTGTAGGCCAGCCTGATCTACAAAGCAAGTTCAGAACAGCTAGGAATGTTACACAGAGAAACCCTGTAAAAAACAAACAAACAAACAAACAAACAAAAACAGAGTATTTATTTTTCTCATTAGCAACAGTAAGT
TTTGCCTTGCTCCTGGGTTTCCCGAGTCAGTAAATATGTTCTAACCTCTGTTATCTTTTGTTTTGAGACAGGGTCTTATATATTTTCTAGGCTGGCCTGGAACTCTTGATTCCCCTGCCTCATCTTCCTAGATGCTGGGGT
TACAGGTATGCACCCGCTGTGCCTGTCAACGAATGTCATCATCCCTGATCCTGCATGACTTTTGTTGTGACAGGAAGTATTTGTGAACCCCAAAAGACCACCAAGGAATGGTTTCTTTAGGGCCTCTTTATTACAAGCTCT
CCTCCAACCCAACCCAGCAGGACAGGAAGAAAAGAAGGAGCAGCCTTGAACCCTCAGCAGGACAAGGTTTTATAGGAAATGGAAGTGAGCGGGAGTCTGTCCTGACAAGTATCTAACCAAATGTCTATTGTAAGAAGATAG
GTGGGTGCTCTGAATGGGTGTACATTTGAAAGTACCTCTGAAACAATCAGACTAATTTGTGATTAATCATTGCTAGGGAAGTAGCTAGATAGTAATTCTGTCCAAGGATAAGCTGTGGGGTCTTTCCTAGTACCTGTGTGC
AGCTTGGGTTCTGCCCTAGGTCAAGTTTATTTCTCTTTGTAGCTCTGTCTGTCCTGGAACTCACTTGTAGGCCAGACTGGCCTTAAACTCTCTTTTTTTTTAATTAATTTATTTATTTATTATATGTAAGTACACTGTAGC
TGTCTTCAGACGCTCCAGAAGAGGGCATCAGATCTTGTTACAGATGGTTGTGAGCCACCATGTGGTTGCTGGGATTTGAACTCCAGACCTTTGGAAGAGCAGTCAGGTGCTCTTACCCACTGAGCCATCTCACCAGCCCGG
CCTTAAACTCTTAGAGAGCCATCTGCCTCTGCTTCCAAGTGCTGGGATTAAAGGCGCATATCACCAATGCCCAGCCAAAAATAAGATATTTTGAACTAAATGGTAATTTTAAAAATTACATACTAAGAATTGCTAGAAAGA
CATTTACGGTCATATCTACACATGAAAAAAAATAGAGGTTGAATGTCAGTGATATAAGTAAAAATAATAGTTTATTATCCAATTTGAGTACAGAAAGGATAGCTAACTAAGCATGTGGAAAGTAGAAGGTAATAATCACTA
GAAATTTCAAGAATACTTCTGAATAACACACATGCAATAGAGAGAATTAACAATACCAAAGATGACTATTGTTAAAAAAAACTTATAAAATTGATAAACATCTAAGAAAAAGAGAATATAAATTACTAATACAAGACAGCT
AGAGTCTACAGATGCTGAGGACATGATATAGCTCAGTGGTTACCTCAAATGTGTGAAGCTCTGGGTTTAGCCCCCAGTTCCACAAAAACTAAAAGGCCCCCAAACAAACAAACAGAAGAGAAAAGGAAGCTATAATATGCC
ATTTAAGCAAAAACTTAAAGAATTTTTATGAAGTGGATAAATTCCTGAAAAATCACATTGTACTCAAGTTGACACAAGAAGAAATAGACAATGGGAATAGTATTAATTAGGCAATTGAATCTGTAAATAAAAACTGTTCA

FIG. 14e

GCAAGTCAGGGGGTGGTGGAGGCAAACACCTTTAATCCTAGCACTTGGGAGGCAGAGGTAGGCAGATCTCTGTGAGTTCAAGGTCAGCCTGCTCTACAGAATGAGATTCAGGACTACCAGGGCTACACAGAGAAACCCTGT
CTTGGGACACTCCTTCTGCCCAAAGAAATCTGTTCAAAAAACAAAGCAGACATCTTAAAAGCCTCTAAGGTATCAGGTATGTATCACTTCTAACCTTCAATGAAGACATAATAGCACTATCCTGAGTTAAAACAGGAAGGA
GAGAGATTTCAACCTGTCTGTGAAAACAGTGCATTTTTGATACCAAACTTGACAAGAACAATAACAACAAAGAAAGAAAGTTAGAGGTCACTCTCATGAAAGTAGATGTGGCTACGCCAGTGCCTGGCAAATACAGAGGTG
GATGCTCACAGTCATCTATAAGATGGAACACAGGGCCCCCAATGGAGAAGCTAGAGAAAGTACCCAAGGAGCTGAAGGGGTCTGCAACCCTATAGGTGGAACAACAATATGAACTAACCACTACTCCCAGACCTCCTGTCT
CTAGCTGCATATGTAGCAGAAGATGGCCTAGTCGGCCATCATTGGGAAGAGAGGTCCCTTGGTCTAGCAAACTTTATATGACCCAGTACAGGGGAACGCCAGGGCCAAGAAGCAGGAGTGGGTGGGTAGGGGAGCAGGACA
GGGGGAGGGTATAGGGAACTTTCGGGGTAGCATTTGAAATGTATGTAAAGAAAATATCTAATAAAAAAGAAAAAAAATGCTAGCCATGCCAGGCGGTGGTAGTGCACTCCTTTAATCCCAGCACTTGGGAGGCAGAGACAG
GTGGATTTCTGAGTTTGAGACCAGCCTGGTCTACAAAGTGAGTGCCAGGATAGCCAGAGCTATACAGAGAAACCCTGTCTGGAAAAAACCAATCAACCAACCAAACAAACAAAAACCCAACAACAAAAAACAAACAAACAA
AAGTCAACCAAACAAACAAAAAAACCCGCTAGCCACGGGGCTGGGATATGACTCAGTGGTTAAGAGCATTGACTGTTCTTCTAGAGGTCCTGAGTTCAATTCCTGGCAACCACATGGTGGCTCACAACAACCTGATGTCCT
TTCCTAGTGTATCTGAAGACAGCTACAGTGTACTCATATAAATAAATAAGTCTTAAAAAAAAGAAGAAGAAGAAGAAGAAGAAGAGTGCTCAGCGGTTAAGAGCACTGACTGCTCTTCTGAAGGTCCTGAGTTCAAATCCC
AGCAACCACATGGTGACTCACAACCATTCGTAATGAGATCTGGTGCCTTCTTCTGGTGCATCTGAAGACAACTACAGTGTCCTTAGATGTAATAATAAATAAATCTTAAAAACCAAAAGGCCCCAGAAGCTAGTTATATTA
GATGCACTCATCAGTATTAATTTGGCTTCTTTGGAAGCACAGTGTGTTAAGCATTGGAAAGCAATCAAGAATTCACTACAGTGTTACACTAAGTGAGGCCTTCAGAGGCACCTGCTCCAGGCTATCAAAGAAGAACTATTA
ATGTTAAGATGCAAAGAAAATGGAGACTTTTTCCTGGTGACATCCATGTTCAATGCCTGTGTGGTAACAGGATATCCTGTGGCCTTTGACCCTGATTCTGATCTGGTTTTCTTTTCTTCTTTTTTAAAATATTTTTTAATC
TTTAATTTTTATTTTATGTCCTCTGATGAGTGTATGGGATTGTGGAATCCCTCAGAGCTGGAGTTTATAGACAGGCATGAACTGCCATGTACGTGTTGAGAATTGAACCCAGGACCTCTGGAAGAACAGCCAGTGCACTTA
ACCACTGAGCCATCTCTCTAGGCCCTGGTTTTCTTTTCTCTTTACTGATTTTGGCCGTGGGTCCAGCCACCCTGTCTCCTGCCCTCCCCCTTTACATCCTATAGCCCAACCAGTGTTTCCTAATGTTGTTTAATAACTTTT
CAAGCTTTTCAGTTCATATTGGCCAAAGCAAGTTCTTCTATATATAATTAGGAGCCCAGATGATGGGCCAACCCAAACTTACCTTGATTTGACTTTGAGGCTGCCAGTAGCAAGCAGCCCCCTAAAGACAGAACAATAAAG
CAAAGGAAAACAAAGACAAAATCACCACAATTAGAGAGCTGGTGAGCCTGATGTCGGTGAGGGCAGAGGTGGATGGGAGGTTGAAGACAGAAGTGTATTAGTTCAAGTATAATAAGCTACATATACAGATGAGACAAGAAT
GGGGTTCCCTGCCGAACACAGATCATTTCTCAGGCTCCTGGCAGAAATAATAGCCAAAGGGGGCTTAATATGAACTGGGAGATGATGGGGAGTAACCTCACTGGAGGGACAGAGGGTGCTAAGCTTCCGGGAAACACTCAG
GGAAGTAGAGGCAGAAAGTAGTGCTCATGGAGTATGAGTGTTGGGAGTATGTGACACCCAGGATACAAGATGGACAGCAGGAAGTCACTCCGGAAAGAGGCCACAGCCAGGTGACACACTCCTTGCTCTTGTTTGGGAGCT
TGGTGTGTTCTCTCATGGCACAAAAGGAAAAGATTTTTGGATGCCAATCAGAAAAGCTGAACTCTCAAAGGAGCCCTGGAATCCCCCAAACAAAACAAAGCAAATAGACAAGCAAACAGCGTCTAACTGGGGAGTGAAGTT
CCTTCAGCTGGTAGATTAGGCAGGCACCCCGACTGGTCTGGTACAGGCCTGGTCCTGCTGCCAGCCACAGCTCTCTTCACAAGTTTTGCTCTTTGTGCTGGCTCAGGTAGATGCCACTGCAGGTCTGTTCTTCCTTCTGTT
TTGGCCTGTGAGTTCACAGCTAAGCCAGAATGCCTGGGCCTGGCCACATGGTGAGGGCTGTCAGACAATCCCCACCCAGACCATTCTGCCAGCTCAGCCCCGGG

-0.68 kb (*SmaI* restriction endonuclease sites are underlined)

FIG. 14f

SEQUENCE ID NO. 33

-7 kb

TTTGTTTTGGTGGGTTTTGGCCGGCTTCTTTACTGCAAACTGTTTTATCAGCAAGGTCTTTATAACCTGTATCTTGTGCCGACCTCCTATCTCATCCAATGACTTAGAATGCCTAACCATCTGGG
AATGCAGCCCAGTAGGTCTCAGCCTCATTTTACCCAGTCCCTATTCAAGATGGAGTTGCTCTGGTTCAAACGCCTCTGACAAAGAGGGTTTTGGAGAATCATGAGTTTCTGCAAACTGAGGGTTA
AGAGGGAGAGGGTCTCCCTTCCTCATTCATCCCCTCCTACCCTTGCTGTACAAATATTTTTCAAGCACCAACTCTCTACCAGGCACTGATTATGGGAGCTGTGCCCTTAGAGGCAACCGGCACCA
GCTGAGCAGCCCAAGGGCCCCTCTAGACCAAACAACAGCAGGAATGAAGAGGCCCTGGCTGAGCCTAAGGAGTTCCGAGAAGGGACAATTGTTATTCCATGAGACAGGGATGGCAGCTGCCCCCA
GCTTGTCCATGGAGACTATGGAGAGAGAATGAAGAAGGGCGTGCCAAGGTGGAGCTGGGGCTCCTCGTTCAGACCCTTAAGGCATGAATTGGTGCTTATTCCAGCAAAGTCCCCCACAGACATGA
GGCAGCTTCATCCCTAAGTCTTCTCTTCTCCCAGGGTAATGTCCCCCATTGCCAGTCCCAATGCCTGGAGGCTGACAACGAGGCCACCCTCCTTGTACCTCCTTATCCCCTGCCCCATGTTGGGC
TCTGCCACCCTGTCCTTGTTTCTGTCCTCTCAGTCATCAGCCTCCCCTGCACCTGCCCCTTGTAACCCACTCACACCCTGGTCACATCTCTTTTCCAATTAAAACCTCAAAGCTCAAAAGCTCAGA
TGATGAGACCAGCCCCAGCCCCTACCTCTACAGCCACCTGGCACGCCCCGCAGCCAGGTGCAGGTGCATCGCCCCGGCCCCAGGAGTCCTCACAAGCAGGGTCTCCCAACAAACCCATCAGCTACCC
TGTCCAAAAGACCCTGTGTCTGCTCCTGTCTTACCTCCTTCCCTCCTTTCTTCCCTCCTTCCTTCTTTCATTTATTCCTTCCCTCCTTTCTTCCTTCCCTCCCTCCTTCCTTCTTGTCTTCCTTC
CTTCTTTCCTTCCCTCCTCCCTTCTTTTATGTCTTCCTTCCCTCCCTTCCTTGCTTCTTCCTCCCTCTCTTTCTCCCTCCTTCCAACCTTGCCTTCTTTCCTTCCCTCCCTCCTTCTACTTCCTT
CCTCCCTCTATCCCTCTCTCCCTCTCTCCCTTCCTTCCTTCCTTCCTTCCTTCCTTCCTTCCTTCCTTCCTTCCTCTTCCCTCCTCCCTTCTCACCAACACTCCCATAATATTAAAGTTAAGGGC
TAGCAGTTGTACAGGACTAACTAGGGACCAGGCCCTGCTCTAAGATCTTTACATGAATTGCCTCCTTTAATCCATATGACAGATAGTGGTCGAGCTGGAGTATACAAACAAAAAGAAGCTTTTGA
GCCCCTGAAATACCATAGGCAGGAAGCAAGCAAGAAAATTATTCAGGTGCAAATCTTGGCTATTATGGAAAAGGAAAGCTAACACAGAGAATAGACCAAGAGCCCAGAGGATGGAACCAAGAGCC
CAGAGGATGGAACCAAGAGCTAAGGAGATTCATTCCGGGCAGTGGAACTGCCTTCTGAAGGAACTGGTCACGTGGTCACACGTGCCAGGCCAGATTTCAGAATTTCCTTTTTTCTCTTTTCTCTA
TTTCTTTCTTTCTTTCCTTTTTTTTTTTTTTTGACAGAGGCTTGCTCTGTTGCCCAAGCTGGAGTGCAATGGCCTCACTGCAACCTCCGCCTCCCAGGCTTAAGCGATTCTCCTGCCTCAGCCT
CCCAAATTGCTGGGATTACAGGTGCAAGCCACCATGTCTGGCTAATTTTTGTATTTTTAGTAGAGATGGGGTTTCACCATGTTGATCAGGCTGGTCTCGAACTCCTGACCTTGCGATCTGCCCGC
CTTGGCCTCCCAAAGTGCTGGGATTACAGGCATGAGCCACCACGCCTGGCCCTTTCTGCCATCTTTATCCTTGATCCAACATTACCCTCCACCCACAATCACCATTCAGTTCATAGAGTTTTGTT
TTGTTTTGTTTTGTTTTGAAACAGAGTCTCGCTCTTGTTGCCCAGGCTGGAGTGCAGTGGCATGATCTTGGCTCACTGTAACCTCTGACTTCCGGATTCAAGCAATTCTCCTGCCTCAGCTTCCT
GAGTAGCTAGGACTACAGACATGCGCCACCATGCCTGGCTAATCTTTGTACTTTTAGTAGAGACGGGATTTCACCATGTTGGCCACAGTGGTCTGGAACTCCTGACCTCAGGTGATCCGCCTGCC
TCGGCCTCCCAAAGTGCTGGGATTACAGGCGTGAGCCACTGTGCCCGGCTGAGTTGTGCTGTTTTTATGCCAGGATCAAATGGAGAAATGCACAAAAATAGTGAGGAGATTTAAAAAGCATACTT
TTCTCAGTAACTAATAGAATAAGACGACAAATAGCAAGGATATAGGTAGAGAAAGGATATAGAATATTTGAGAATATACAGTCACAGAATACAGTGCAGTGAGACACTTCTTTTGGAGTGCACAG
GAAGCCCTAATCAAAATGAGCCCTATGTTTATCTGTTAAGCAAGCCTCAAAAAATTTCGAAGGTCTGAAATCAAACAGAGCATATTCTCTGACTACAAGGGAATTAAGCAAAAAATTAGTTTAAA
AACATGACTGGAAAATCCCCAAGGTTTAGAAGTTTTTCTTTTTTTTCTAAGTTGGTAATATGAATTGGAAGGGTTAGAGGTTAAGCAGAATATATTTGAATAACCTATAGGTCAAAGAAGACATC
TCAATGAAAATAAAAAGATATTTTGAACAAATGGTAATTGAAATATGACATATCAAAAGTTGTGGGATGCATATAAAGCTGTACTTAGAAAGAAAATATAGCCATAAATACATATGTAAAAAAAG
AATAAAGGAGCTGGGCACAGTGGCATGCATCTATAGTCCCAGCTACTAGAGAGACTGAAGTGGGAGGATCACTGGAGCCCAAGAGTTGAAGATGAGTCAAGGCAATATTAAAAAAAAAAAAAAAA
AAAAGGAAAAAAATGGTTCAATATCAATTATCTAAGTAAAAGTATTTATTTAATGTCCAACTCATGAGTATAGGAAAAGAATAGCTAATTAAACCCAAAGATGTAGAAGGCACGATATAATAAGA
GTAAAAATTTCAGAAATATAAAAAAGTATACATATAGTACAGAAAATTAACAGAACCAAAATGGATTATTAAAAAGACTAATAAAATGGATAACACCCTAAGAAAACTAATCAAGAGGCCAGGCA
CAGTGGCTCACGCCTGTAATCCCAGCACTTTGGGAGGCTGAGGCCGGCAGATCACCTGAGGTCAGGAGTTTGAGACCAGCCTGGCCAATATGGAGAAACCTCATCTCTACTAAAAATACAAAAAA
TAAGCCAGATGTGGTGGCACATCCCTGTAATCCCAGCTACTTGGGAGGCTGAGGCAGGAGAATTGCTTGAACCCGGGAGGCGGAGGTTGCAGTAAGCCGAGATCATGCCATTGCACTCCAGCCTG
GGCAATAAGAGTGAAAGTCTGTCTCAAAAAGAAAAAAGAAAATGAATCAAGAAAAAAGAGAACACAAATAACCAATATCAGAGATGAAAAGGGCCAAAACCACAGATCCCAGATGCTTAAAATAT
ATAATAAACAATTTTAAGCCAATAAATTAAAGAATTTAGATGAAATAGACAAATTCCTAGAAATACATATCTGACTCAAACTGACACATGAAGAAGTAGACAATTGAAATAGTGCCACTTAAGTA
ATTGAATTTGTAATGGTTTAAAACATTTTTCCTTCTTTTTTCCAGCTCCAGCTGAAAGGATTGATTCTGTAATTAAAAACTTCAATGAACAAACAATCTTAAAGATTTAGATGGCATCACTGGTG
AATCATCCCAAACATTTAAGGACGAGATAACACCATTATACGCAAATTATTCTACTTAATTATAAAAAGGGGGAGGGAAGATGGATTTCCAACTTGTTTTATGAGAACAGCATAATTTTTTGATA
CTCAAATTAGACAAGAATTCCACAAGAAAGGAAAATTACAGGCCCATCTCATGAACATCAATGCAAATGTCTTAAATAAAATATTAGCAAATTGAGTCCAGTGCTTTCTGTATAAGGATAATACA
TCATAATCAAATTGGGTTTAATCTAAGAAGCCATGGTAGGTTTAACACCAAAAAATCAACAATGCAATAATTCACCACATTACTAGAATAAAGGTGAAAAATTATGTCATGTCAGACAATCAAAG

FIG. 14g

GCACCTGTTCTAGGCTTTCAAAGAGGAGCTAGTGGTACAAGGATGCAAGGGCAGTGGTGACTCCTTTCTAGTGGCATTAGCTGAAGTGAGAATGGCAGCGTCCCATCCTGGGGACAGAAGTGACG
TCTATGTCAGACGCCTGTGGTCTTGACATGCCCCTTGTGGCCCCTTGTGGTCTGTTTTTTTTTTCTCCACTGGATGTGATTTTGGCCATGGTTCCAGCCACACTGTGTCCCTGCCCATTTTTAGA
TCCTGGTCCCCCAACCTGCCCAGTGATTTTTTTTTTTTTTTAGATGGAGTCTTGCTGTGTCGCCAGGCTGGAGTGCAGTGGCGCGATCTCGGCTCACCGCAACCTCCGCCTCCCAGGTTCAAGCG
ATTCTCCTGCCTCAGCCACCCGAGTAGCTGGGACTACAGGTGTGCGCCACCACGCCCGGCTAATTTTTGTATTTTTAGTAGAGACGGGGTTTCGCCATCTTGGCCAGGAATGTCTCCATCTCTTG
ACCTCGTGATCTGCCCAACTCAGCCTCCCAGAGTGCTGGGATTACAGGCGTGAGCCACTGTGCCCCGCCTACCCAGTGATTCTAAATGCAGTTCAATGGCCTTTCAGTTCATGGAGGCCAAAGCA
GGTTCTGCTGCATTAAATTAAGAAACTGGGCTGGGTGTGGTGGCTAACACCTGTAATCCCAGCACTTCAGGATACTGATGTGGATTACTTGAGCCCAGGAGCTTGAGACCAGCCTAGGCAACATA
GTGAAACCCTGTCTCTACCAAAAACAAAAACAAAAACAAAACAAAAAACCAAAACCCAAAATTAGCTGGGCATGGTGGCATGCATCTGTGGTTCCAGGTACTCAGGAGGCTGAAGCATGAGGATC
ACTTGAGCCCAGGAGGTGGAGGCTGCAGTGAGCAGTGTTCACACTGCTGCATTCCAGCCTGGGCAACAGAGTGAGACCCTAATTCAAAAACAAACAAACAGAATGAGAGAGAGAGAGAAGAAAAG
AAAGAAGGAACCCAGTTAAAGAAGTTGGGTCCATTTGGATTTTTCCTGGTTTGTTTTATCTGCTGCCACCAGCAGCCTCCTGAAGTTACAAAAATAACACAAAGTAAAATAAGGCAAAACCACCA
TCTGCTTGAAAGAGTTTACAAACCTGATGGTGGTCGTGGGGTGGATGGAAGATTAAAAAAATGGGGACAGAAGTGAATTAGTGCAAGCCACTTGCACTGACAAGATGGGGATGGACTTCTGTGGA
AGGCAGAGGAGGTCATGCCTCATGCCCCTGGTAGGAAAAGTGGCCAAAGAGGGCTTCAGAGAACAGGGGCTGATGGATGGGCTACATCTTGATGTGAGTCAAGCTCCTGGATGGCTGGAGAGAGG
AAGGATGTTCTAGTTGGGGGAACAGCTTGGACAATGGAGACCCAAGAAAGCCATGTTCTAGCAGTGTGAATGTTGTGGATGCTGAAGTGCCAGGATGCAAGGTGGAGAACTGGGAAATGGCCCTG
GAAAGGGGCCAAAGCCGGGTGATGAAGCACCTTGTCTACTGTGACGGAGCTTGGATCTCTCTTGTGGTCCAAAGGGAAAGGATTGCTGAATGTAAAGCCAATGTCACCAGAAAAGCTGAATCCAC
AAGAGAGTCCTGGAGTCCAAAAGAGCATCTCATGGGGAATCAGGAAAGTTCTGGCATTTGGCAGATTAAGCAAGTGTCTTGATTTGAAGTCCAGTTTAGTCCCAATACTCCCTCCCACACCCACC
ACATCGCACAATTTGGTTTTGTTTATTTACTCCAGGTTAAGGTAGAGTCTCTTAGCTTGGTTTGAGTGCTGTACTCTTCTCTCTGGTCTGATATTTGGAACTAAAGCCAAGCCAGAACTCCAGGG
CCAAGGGGGATGTTGAAAATTGTCTGAGTCCCCAGACCACCCTGCCAGCTCATGGCAAAGGGAGGGATCAGAG

-0.7 kb

UPSTREAM CONTROL ELEMENTS OF THE PROOPIOMELANOCORTIN GENE AND THEIR USE

PRIORITY

This is a divisional of U.S. patent application Ser. No. 10/336,091 filed Jan. 3, 2003, now U.S. Pat. No. 7,125,979 which is a continuation-in-part of U.S. application Ser. No. 10/255,175, filed Sep. 24, 2002 now abandoned, which claims the benefit of U.S. Provisional Application No. 60/324,406, filed Sep. 24, 2001, and claims the benefit of U.S. Provisional Application No. 60/392,109, filed Jun. 28, 2002. All of the prior applications are incorporated by reference in their entirety herein.

STATEMENT OF GOVERNMENT SUPPORT

This invention was made with United States government support pursuant to grants TW01233 and DK55819, from the National Institutes of Health. The United States government has certain rights in the invention.

FIELD

This application relates to the field of transcriptional control elements, specifically to enhancers of the proopiomelanocortin (POMC) gene, and the use of these elements to direct expression of a heterologous nucleic acid sequence. Transgenic mice carrying a transgene that include transcriptional regulatory regions of a POMC gene are also disclosed.

BACKGROUND

POMC neurons of the hypothalamus are critical components of the neural circuitry controlling appetite, feeding, and metabolism. In addition they modulate the activity of other hypothalamic neurons which control reproduction, thyroid hormone levels, growth hormone secretion, prolactin secretion, and neuroendocrine stress responses. These neurons also are involved in the nervous system's endogenous analgesic and reward circuits. POMC is a prohormone that is postranslationally processed into several different biologically active neuropeptides. The most important of these neuropeptides within the hypothalamus are alpha-MSH, gamma-MSH, and the opioid beta-endorphin. The two MSH peptides are potent anorexigenic substances that play a fundamental role in modulating weight homeostasis. β-endorphin also modulates food intake by at least two distinct mechanisms. It can directly increase food intake when administered acutely, but it also modulates the neural circuitry underlying the rewarding aspects of food ingestion and thereby influences an organism's motivation to work to obtain food.

Genetic evidence in humans implicates the POMC gene in the regulation of weight and fat mass. Rare mutations causing null alleles result in a syndrome of adrenal cortical insufficiency, red hair, and obesity. The three components of the syndrome are secondary to losses of peripheral ACTH, peripheral MSH, and central MSH, respectively. However, a number of other gene association and quantitative trait loci analyses in human populations suggest a much more common role for the POMC gene in weight homeostasis.

The POMC promoter has been identified. For example, in the rat, 5' flanking sequences form −323 to −34 are sufficient for correct spatial, temporal and hormonally regulated expression of POMC in the pituitary gland (e.g. see Liu et al., *Mol. Cell. Biol*. 12:3978-3990, 1992; Liu et al., *Biochem. J.*

312:827-832, 1995). In addition, a transgene including approximately 13 kilobases (kb) of the mouse POMC gene has been demonstrated to produce cell specific and developmentally regulated expression of POMC in transgenic mice (Young et al., *J. Neurosci*. 18:6631-6640, 1998). However, other specific nucleic acid elements involved in tissue specific expression, such as a POMC enhancer, have not been identified.

SUMMARY

The nucleic acid sequence of the transcriptional control region of the proopiomelanocortin (POMC) gene is disclosed herein. Specifically, a human, rat, rabbit, mouse, hamster, and cow POMC enhancer element are described herein, and the use of these enhancer elements to direct transcription is disclosed. Hybrid transgenes, comprising a POMC transcriptional control element operably linked to a nucleic acid sequence encoding a marker are also enclosed. In addition, transgenic mice carrying a hybrid transgene including a POMC control element operably linked to a marker are disclosed herein.

Specifically, an isolated POMC enhancer element is disclosed herein. The element has a nucleic acid sequence set forth as a) SEQ ID NO: 9 or at most fifty conserved enhancer substitutions thereof; b) SEQ ID NO: 15 or at most twenty conserved enhancer substitutions thereof; or c) SEQ ID NO: 19 or at most fifteen conserved enhancer substitutions thereof.

A POMC enhancer element is disclosed herein that includes one or more of a) an nPOMC1 element comprising a nucleic acid sequence as set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, or a conserved enhancer substitution thereof based on a template nucleic acid sequence as set forth as SEQ ID NO: 9; b) an nPOMC2 element comprising a nucleic acid sequence as set forth as SEQ ID NO: 10, SEQ ID NO: 11, SEQ ID NO: 12, SEQ ID NO: 13, SEQ ID NO: 14, or a conserved enhancer substitution thereof based on a template nucleic acid sequence as set forth as SEQ ID NO: 15; c) an nPOMC3 element comprising a nucleic acid sequence as set forth as SEQ ID NO: 16, SEQ ID NO: 17, SEQ ID NO: 18, or a conserved enhancer substitution thereof based on a template nucleic acid sequence as set forth as SEQ ID NO: 19. These expression elements direct expression of a heterologous nucleic acid sequence in a proopiomelanocortin neuron. An isolated enhancer element including a nucleic acid sequence at least 90% homologous to an enhancer element comprising a nucleic acid sequence set forth as SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, or SEQ ID NO: 19 is also disclosed. The enhancer element directs expression of a heterologous nucleic acid sequence in a proopiomelanocortin neuron. Vectors including these enhancer elements, and host cells transfected with these vectors, are also disclosed.

A transgenic mouse is described that expresses a marker in proopiomelanocortin neurons. The mouse carries a transgene comprising a nucleic acid encoding the marker operably linked to a proopiomelanocortin enhancer sequence. The proopiomelanocortin enhancer sequence directs expression of the marker in proopiomelanocortin neurons in the arcuate nucleus, nucleus of the solitary tract, and immature granular layer neurons of the dentate gyrus of the hippocampus of the mouse. A section of the arcuate nucleus of the mouse can be used to determine if an agent affects caloric intake, food intake, appetite, or energy expenditure.

A method is disclosed herein for screening for an agent that affects caloric intake, appetite, energy expenditure or food intake. The method includes contacting a histological section of an arcuate nucleus from a non-human transgenic animal, with an agent to be tested. Proopiomelanocortin neurons in the histological section express a heterologous marker that distinguishes the proopiomelanocortin neurons from other cells in the histological section. An electrophysiological response of a proopiomelanocortin neuron in the histological section is assessed, thereby determining if the agent affects caloric intake, appetite, energy expenditure, or food intake.

The foregoing and other features and advantages will become more apparent from the following detailed description of several embodiments, which proceeds with reference to the accompanying figures.

BRIEF DESCRIPTION OF THE FIGURES

FIG. 1 is a set of diagrams and digital images showing the generation of transgenic mice expressing EGFP in ARC, brainstem, and hippocampal neurons. FIGS. 1*i* and 1*j* are a set of digital images showing total nuclear staining with the fluorescent dye Hoechst 33258 and immature granular layer neurons by EGFP fluorescence, respectively, in the dentate gyrus (DG) of the hippocampus. FIG. 1*k* is a digital image showing a higher magnification of the EGFP-positive neurons in the DG depicted in FIG. 1*j*. FIGS. 1*l* and 1*m* are a set of digital images showing the identification of immature granular layer neurons by immunohistochemistry with an antisera directed against GFP in the DG of a 2 month old and an 18 month old transgenic mouse, respectively.

FIG. 2 is a tracing and graphs showing activation of MOP-Rs hyperpolarizes the EGFP-labeled POMC neurons by opening G protein-coupled inwardly-rectifying potassium channels.

FIG. 3 are tracings and graphs demonstrating that leptin depolarizes POMC neurons via a non-specific cation channel, and decreases GABAergic tone onto POMC cells.

FIG. 4 is a set of images showing that the GABAergic inputs to POMC cells are from NPY neurons that co-express GABA. FIGS. 4*a*, 4*b* and 4*c* are representative.

FIG. 5 is a set of digital images of c-fos expression in Pomc-EGFP mice.

FIG. 6 is a set of images relating to the electrophysiological and neuropeptide responses to $PYY_{3-36}$ and Y2A.

FIG. 8 is a set of digital images of sections of the arcuate nucleus.

FIG. 9 is a set of diagrams showing sequence alignments.

FIG. 11 is the nucleotide sequences of mouse (*M. musculus*), human (*H. sapiens*), and rat (*R. norvegicus*) nPOMC1 (FIG. 11*a*), nPOMC2 (FIG. 11*b*), and nPOMC3 (FIG. 11*b*) elements. NPOMC1 element from mouse chromosome 12 nucleotides 3,808,013-3,808,447 (SEQ ID NO: 20), nPOMC1 element from human chromosome 2 nucleotides 2,324,416-2,323,942 (SEQ ID NO: 21), and the nPOMC1 element from rat chromosome 6 nucleotides 1,962,320-1, 962,887 (SEQ ID NO: 22); nPOMC2 element from mouse chromosome 12 nucleotides 3,810,489-3,810,724 (SEQ ID NO: 23), nPOMC2 element from human chromosome 2 nucleotides 2,322,890-2,322,659 (SEQ ID NO: 24), and the nPOMC2 element from rat chromosome 6 nucleotides 1,964, 684-1,964,909 (SEQ ID NO: 25); nPOMC3 element from mouse chromosome 12 nucleotides 3,813,451-3,813,596 (SEQ ID NO: 26), nPOMC3 element from human chromosome 2 nucleotides 2,320,149-2,320,009 (SEQ ID NO: 27), and the nPOMC3 element from rat chromosome 6 nucleotides 1,967,170-1,967,309 (SEQ ID NO: 28) are shown.

FIG. 12 is a set of graphs demonstrating that Ghrelin increases the secretory activity of NPY neurons onto POMC neurons hyperpolarizes POMC neurons, and decreases the frequency of action potentials in POMC neurons. FIG. 12*a* and FIG. 12*b* were recorded in conventional whole cell mode.

FIG. 13 is a set of graphs demonstrating that fenfluramine (d-FEN) increases the frequency of action potentials and depolarizes POMC neurons.

FIG. 14 shows the sequences of the POMC regulatory region. FIG. 14*a* is the sequence of the mouse POMC regulatory region from −13 to −9 kilobases (SEQ ID NO: 29). FIG. 14*b* is the sequence of the human POMC promoter region from −11.5 to −7 kilobases (SEQ ID NO: 30). FIG. 14*c* is the sequence of the rat POMC promoter region from −13.8 to −9.8 kilobases (SEQ ID NO: 31). The nucleotide sequences of the nPOMC1 and nPOMC2 elements are highlighted in gray in FIGS. 14*a*-14*c*. FIGS. 14*d*-14*e* are the sequence of the mouse POMC promoter region from −9 to −0.7 kilobases (SEQ ID NO: 32). FIGS. 14*f*-14*g* are the sequence of the human POMC promoter region from −7 to −0.7 kilobases (SEQ ID NO: 33). FIG. 14*f* is the sequence of the rat POMC promoter region from −9.8 to −0.7 kilobases (SEQ ID NO: 34). The nucleotide sequences of the nPOMC3 element is highlighted in gray in FIGS. 14*d-f.*

SEQUENCE LISTING

Figure 1A:
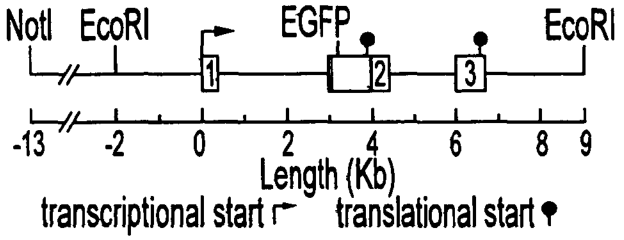
FIG. 1*a* is a schematic diagram of the structure of the POMC-EGFP transgene.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is the nucleic acid sequence of the 5' half of the human nPOMC1.

SEQ ID NO: 2 is the nucleic acid sequence of the 5' half of the cow nPOMC1.

SEQ ID NO: 3 is the nucleic acid sequence of the 5' half of the hamster nPOMC1.

SEQ ID NO: 4 is the nucleic acid sequence of the 5' half of the mouse nPOMC1.

SEQ ID NO: 5 is the nucleic acid sequence of the 5' half of the rat POMC enhancer.

SEQ ID NO: 6 is the nucleic acid sequence of the 3' half of the human nPOMC1.

SEQ ID NO: 7 is the nucleic acid sequence of the 3' half of the mouse nPOMC1.

SEQ ID NO: 8 is the nucleic acid sequence of the 3' half of the rat nPOMC1.

SEQ ID NO: 9 is the nPOMC1 complete template based on multiple species.

SEQ ID NO: 10 is the nucleic acid sequence of the human nPOMC2.

SEQ ID NO: 11 is the nucleic acid sequence of the cow nPOMC2.

SEQ ID NO: 12 is the nucleic acid sequence of the rabbit nPOMC2.

SEQ ID NO: 13 is the nucleic acid sequence of the mouse nPOMC2.

SEQ ID NO: 14 is the nucleic acid sequence of the rat nPOMC2.

SEQ ID NO: 15 is the nPOMC2 complete template based on multiple species.

SEQ ID NO: 16 is the nucleic acid sequence of the human nPOMC3.

SEQ ID NO: 17 is the nucleic acid sequence of the mouse nPOMC3.

SEQ ID NO: 18 is the nucleic acid sequence of the rat nPOMC3.

SEQ ID NO: 19 is the nPOMC3 complete template based on multiple species.

SEQ ID NO: 20 is the nucleic acid sequence of the complete mouse nPOMC1.

SEQ ID NO: 21 is the nucleic acid sequence of the complete human nPOMC1.

SEQ ID NO: 22 is the nucleic acid sequence of the complete rat nPOMC1.

SEQ ID NO: 23 is the nucleic acid sequence of the complete mouse nPOMC2.

SEQ ID NO: 24 is the nucleic acid sequence of the complete human nPOMC2.

SEQ ID NO: 25 is the nucleic acid sequence of the complete rat nPOMC2.

SEQ ID NO: 26 is the nucleic acid sequence of the complete mouse nPOMC3.

SEQ ID NO: 27 is the nucleic acid sequence of the complete human nPOMC3.

SEQ ID NO: 28 is the nucleic acid sequence of the complete rat nPOMC3.

SEQ ID NO: 29 is the nucleic acid sequence of the mouse POMC 5' flanking region from approximately −13 to −9 kilobases from the transcriptional start site.

SEQ ID NO: 30 is the nucleic acid sequence of the human POMC 5' flanking region from approximately −11.5 to −7 kilobases from the transcriptional start site.

SEQ ID NO: 31 is the nucleic acid sequence of the rat POMC 5' flanking region from approximately −13.8 to −9.8 kilobases from the transcriptional start site.

SEQ ID NO: 32 is the nucleic acid sequence of the mouse POMC 5' flanking region from approximately −9 to −0.7 kilobases from the transcriptional start site.

SEQ ID NO: 33 is the nucleic acid sequence of the human POMC 5' flanking region from approximately −7 to −0.7 kilobases from the transcriptional start site.

SEQ ID NO: 34 is the nucleic acid sequence of the rat POMC 5' flanking region from approximately −9.8 to −0.7 kilobases from the transcriptional start site.

SEQ ID NO:35 is the consensus core binding site for STAT3.

SEQ ID NO:36 is a highly conserved palindromic oligonucleotide sequence within the nPOMC1 template (SEQ ID NO: 9).

SEQ ID NO: 37 is the sequence of an exemplary polylinker.

DETAILED DESCRIPTION

I. Abbreviations

α-MSH: alpha melanocortin stimulating hormone
Arc: arcuate nucleus of the hypothalamus
CPP: m-CPP hydrochloride, 1-(3-Chlorophenyl)piperazine 5-$HT_{2B/2C}$ receptor agonist
d-FEN: fenfluarmine
DG: dentate gyrus of the hippocampuis
EPSP: excitatory postsynaptic potential
GABA: γ-aminobutyric acid
GFP, EGFP: green fluorescent protein, enhanced green fluorescent protein
hGH: human growth hormone
IPSC: inhibitory postsynaptic current
kb: kilobase
kg: kilogram
MOP-R: μ-opioid receptor
MK: MK212 hydrochloride, or 6-Chloro-2-(1-piperazinyl)pyrazine 5-$HT_{2C}$ serotonin receptor agonist.
MV: millivolts
nPOMC1: neural POMC regulatory element 1
nPOMC2: neural POMC regulatory element 2
nPOMC3: neural POMC regulatory element 3
NPY: neuropeptide Y
NTS: nucleus tractus solitarius
pmol: picomole
POMC: proopiomelanocortin
RIA: radioimmunoassay
RPA: RNase protection assay
s.e.m.: standard error of the mean TH: tyrosine hydroxylase
μM: micromolar
V: volts
Y2A: N-acetyl ($Leu^{28}$, $Leu^{31}$) NPY (24-36)

II. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Action potential: A rapidly propagated electrical message that speeds along an axon of a neuron and over the surface membrane of many muscle and glandular cells. In axons they are brief, travel at constant velocity, and maintain a constant amplitude. Like all electrical messages of the central nervous system, the action potential is a membrane potential change caused by the flow of ions through ion channels in the membrane. In one embodiment, an action potential is a regenerative wave of sodium permeability.

Affinity Tag: A nucleic acid sequence which can be included in a vector which can aid in the purification of a protein encoded by the vector. The term affinity tag refers to the nucleic acid sequence for the tag, and the tag protein sequence encoded by the nucleic acid sequence. Examples of affinity tags include, but are not limited to: histidine, such as 6× histidine, S-tag, glutathione-S-transferase (GST) and streptavidin.

Agent: Any polypeptide, compound, small molecule, organic compound, salt, polynucleotide, or other molecule of interest.

Animal: Living multi-cellular vertebrate organisms, a category that includes, for example, mammals and birds. The term mammal includes both human and non-human mammals. Similarly, the term "subject" includes both human and veterinary subjects.

Antibiotic Resistance Cassette: A nucleic acid sequence encoding a selectable marker which confers resistance to that antibiotic in a host cell in which the nucleic acid is translated. Examples of antibiotic resistance cassettes include, but are not limited to: kanamycin, ampicillin, tetracycline, chloramphenicol, neomycin, hygromycin, and zeocin.

Antagonist: A substance that tends to nullify the action of another, as an agent that binds to a cell receptor without eliciting a biological response, blocking binding of substances that could elicit such responses.

Appetite: A natural desire, or longing for food. In one embodiment, appetite is measured by a survey to assess the desire for food. Increased appetite generally leads to increased feeding behavior.

Binding: A specific interaction between two molecules, such that the two molecules interact. Binding can be specific and selective, so that one molecule is bound preferentially when compared to another molecule. In one embodiment, specific binding is identified by a disassociation constant ($K_d$).

An oligonucleotide binds or stably binds to a target nucleic acid if a sufficient amount of the oligonucleotide forms base pairs or is hybridized to its target nucleic acid, to permit detection of that binding. Binding can be detected by physical or functional properties of the target: oligonucleotide complex. Binding between a target and an oligonucleotide can be detected by any method known to one skilled in the art, including functional and physical binding assays. Binding can be detected functionally by determining whether binding has an observable effect upon a biosynthetic process such as expression of a gene, DNA replication, transcription and translation.

Physical methods of detecting the binding of complementary strands of DNA or RNA are well known in the art, and include such methods as DNase I or chemical foot printing, gel shift and affinity cleavage assays, Northern blotting, dot blotting and light absorption detection procedures. For example, a method which is widely used, because it is simple and reliable, involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target dissociate or melt.

The binding between an oligomer and its target nucleic acid is frequently characterized by the temperature ($T_m$) at which 50% of the oligomer is melted from its target. A higher $T_m$ means a stronger or more stable complex relative to a complex with a lower $T_m$.

CAAT box: An upstream promoter element generally located at −75 to −80 relative to the RNA start site. It influences the frequency of initiation, most likely by acting directly on the basal transcription factors to enhance their assembly into an initiation complex. The sequences between the CAAT and TATA elements are irrelevant and the distance between them is flexible. The separation between the CAAT and TATA elements can usually be changed by 10 to 30 base pairs before rendering them inoperable.

Caloric intake or calorie intake: The number of calories (energy) consumed by an individual.

Calorie: A unit of measurement in energy. A standard calorie is defined as 4.184 absolute joules, or the amount of energy it takes to raise the temperature of one gram of water from 15° C. to 16° C. (or 1/100th the amount of energy needed to raise the temperature of one gram of water at one atmosphere pressure from 0° C. to 100° C.). Food calories are actually equal to 1,000 standard calories (1 food calorie=1 kilocalorie).

Conserved Enhancer Substitution: A modification made in an enhancer sequence that does not alter the ability of the sequence to direct expression of an operably linked nucleic acid sequence. Modifications include substitutions (base replacements), insertions, and/or deletions of nucleic acid residues. In several specific, non-limiting examples, conserved enhancer substitutions include at most about fifty, such as at most about one, at most about two, at most about five, at most about ten, at most about fifteen, or at most about twenty base substitutions in a POMC enhancer element. A POMC enhancer element includes, but is not limited to, an element with a sequence set forth as SEQ ID NO: 9, SEQ ID NO: 15, or SEQ ID NO: 19. In several other specific non-limiting examples conserved enhancer substitutions include at most about fifty substitutions in any one of SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8. In other specific, non-limiting examples, conserved enhancer substitutions include at most fifty, such as one, at most two, at most five, at most ten, or at most twenty insertions or deletions in any one of SEQ ID NO: 1, SEQ ID NO: 2, SEQ ID NO: 3, SEQ ID NO:

4, SEQ ID NO: 5, SEQ ID NO: 6, SEQ ID NO: 7 or SEQ ID NO: 8. Additional examples are described below.

Conservative variation: The replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

Non-limiting examples of conservative amino acid substitutions include those listed below:

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Current: The amount of charge per unit time. Current is generated in a cell membrane of a neuron by an action potential or by opening of ion channels in the cell membrane and serves to depolarize or hyperpolarize adjacent membrane areas.

Deletion: The removal of a sequence of nucleic acid, such as DNA, the regions on either side being joined together.

DNA (deoxyribonucleic acid): DNA is a long chain polymer which comprises the genetic material of most living organisms (some viruses have genes comprising ribonucleic acid, RNA). The repeating units in DNA polymers are four different nucleotides, each of which comprises one of the four bases, adenine, guanine, cytosine, and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Depolarization: An increase in the membrane potential of a cell. Certain stimuli reduce the charge across the plasma membrane. These can be electrical stimuli (which open voltage-gated channels), mechanical stimuli (which activate mechanically-gated channels) or certain neurotransmitters (which open ligand-gated channels). In each case, the facilitated diffusion of sodium into the cell increases the resting potential at that spot on the cell creating an excitatory postsynaptic potential (EPSP). Depolarizations can also be generated by decreasing the frequency of inhibitory postsynaptic currents (IPSCs), these are due to inhibitory neurotransmitters facilitating the influx of chloride ions into the cell, creating an IPSC. If the potential is increased to the threshold voltage (about −50 mV in mammalian neurons), an action potential is usually generated in the cell.

Electroporation: A method of inducing or allowing a cell to take up macromolecules by applying electric fields to reversibly permeabilize the cell walls. Various methods and apparatuses used are further defined and described in: U.S. Pat. No. 4,695,547; U.S. Pat. No. 4,764,473; U.S. Pat. No. 4,946,793; U.S. Pat. No. 4,906,576; U.S. Pat. No. 4,923,814; and U.S. Pat. No. 4,849,089.

Enhancer: A cis-regulatory sequence that can elevate levels of transcription of a coding sequence from an adjacent promoter. Many tissue specific enhancers can determine spatial patterns of gene expression in higher eukaryotes. Enhancers can act on promoters over many tens of kilobases of DNA and can be 5' or 3' to the promoter they regulate. Enhancers can function either by initiating transcription from a promoter operably linked to the enhancer or by providing binding sites for gene regulatory proteins that increase transcription of a minimal promoter.

Eukaryotic cell: A cell having an organized nucleus bounded by a nuclear membrane. These include simpler organisms such as yeasts, slime molds, and the like, as well as cells from multicellular organisms such as invertebrates, vertebrates, and mammals. Multicellular organisms include a variety of cell types, such as: endothelial cell, smooth muscle cell, epithelial cell, hepatocyte, cells of neural crest origin, tumor cell, hematopoetic cell, immunologic cell, T cell, B cell, monocyte, macrophage, dendritic cell, fibroblast, keratinocyte, neuronal cell, glial cell, adipocyte, myoblast, myocyte, chondroblast, chondrocyte, osteoblast, osteocyte, osteoclast, secretory cell, endocrine cell, oocyte, and spermatocyte. These cell types are described in standard histology texts, such as McCormack, *Introduction to Histology*, (c) 1984 by J.P. Lippincott Co.; Wheater et al., eds., *Functional Histology*, 2nd Ed., (c) 1987 by Churchill Livingstone; Fawcett et al., eds., Bloom and Fawcett: *A Textbook of Histology*, (c) 1984 by William and Wilkins.

Exon: A portion of a gene whose nucleotide sequence is transcribed by RNA polymerase and is present in both the primary heteronuclear RNA transcript and the mature messenger RNA following splicing and deletion of the transcribed intron sequences. An exon (or portion of an exon) can be either nontranslated and contain regulatory information for processing or stabilization of the RNA or translated by ribosomal complexes into an encoded protein sequence.

Food intake: The amount of food consumed by an individual. Food intake can be measured by volume or by weight. In one embodiment, food intake is the total amount of food consumed by an individual. In another embodiment, food intake is the amount of proteins, fat, carbohydrates, cholesterol, vitamins, minerals, or any other food component, of the individual. "Protein intake" refers to the amount of protein consumed by an individual. Similarly, "fat intake," "carbohydrate intake," "cholesterol intake," "vitamin intake," and "mineral intake" refer to the amount of proteins, fat, carbohydrates, cholesterol, vitamins, or minerals consumed by an individual.

Gene: A DNA sequence that comprises control and coding sequences necessary for the production of a polypeptide or protein. The polypeptide can be encoded by a full-length coding sequence or by any portion of the coding sequence in some embodiments, so long as at least a portion of the desired activity of the polypeptide is retained. A "foreign gene" is any nucleic acid (e.g., gene sequence) that is introduced into the genome of an animal by experimental manipulations and can include gene sequences found in that animal so long as the introduced gene contains some modification (e.g., a point mutation, the presence of a selectable marker gene, a non-native regulatory sequence, or a native sequence integrated into the genome at a non-native location, etc.) relative to the naturally-occurring gene.

Hyperpolarization: A decrease in the membrane potential of a cell. Inhibitory neurotransmitters inhibit the transmission of nerve impulses via hyperpolarization. This hyperpolarization is called an inhibitory postsynaptic potential (IPSP). Although the threshold voltage of the cell is unchanged, a hyperpolarized cell requires a stronger excitatory stimulus to reach threshold.

Inhibitory PostSynaptic Current: A current that inhibits an electrophysiological parameter of a postsynaptic cell. The potential of a postsynaptic cell can be analyzed to determine an effect on a presynaptic cell. In one embodiment, the postsynaptic cell is held in voltage clamp mode, and postsynaptic currents are recorded. If necessary, antagonists of other classes of current can be added. In one specific, non-limiting example, to record GABAergic IPSCs, blockers of excitatory channels or receptors can be added. The instantaneous frequency over time is then determined.

In one embodiment, IPSCs give a measure of the frequency of GABA release from an NPY neuron. Thus, as NPY neurons release GABA onto POMC neurons, measurement of IPSC frequency is a gauge of the inhibitory tone that POMC neurons are receiving, and can be used to assess the effect of an agent that affects an NPY neuron, such as an antagonist or agonist of PYY.

Intron: An intragenic nucleic acid sequence in eukaryotes that is not expressed in a mature RNA molecule. Introns of the present disclosure include full-length intron sequences, or a portion thereof, such as a part of a full-length intron sequence.

In vitro amplification: Techniques that increases the number of copies of a nucleic acid molecule in a sample or specimen. An example of amplification is the polymerase chain reaction, in which a biological sample collected from a subject is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of in vitro amplification may be characterized by electrophoresis, restriction endonuclease cleavage patterns, oligonucleotide hybridization or ligation, and/or nucleic acid sequencing, using standard techniques. Other examples of in vitro amplification techniques include strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

Isolated: An isolated biological component (such as a nucleic acid, peptide or protein) has been substantially separated, produced apart from, or purified away from other biological components in the cell of the organism in which the component naturally occurs, i.e. other chromosomal and extrachromosomal DNA and RNA, and proteins. Nucleic acids, peptides and proteins that have been isolated include nucleic acids and proteins purified by standard purification methods. The term also embraces nucleic acids, peptides, and proteins prepared by recombinant expression in a host cell as well as chemically synthesized nucleic acids. The term further includes a nucleic acid sequence isolated from the adjacent 5' and/or 3' nucleic acid sequences as found in the endogenous chromosomal location.

Marker: A protein, or a gene encoding a protein, for which a system is available to identify cells that produce the protein. Specific non-limiting examples of a marker include drug resistance markers, such as G148 or hygromycin. Additionally, a marker can be a protein or a gene encoding a protein for which negative selection can be used to identify the cell expressing the marker. A specific, non-limiting examples of a negative selection marker includes, but is not limited to, the HSV-tk gene. This gene will make the cells sensitive to agents such as acyclovir and gancyclovir. Another specific, non-limiting example of a selectable marker is a protein, or a gene encoding a protein, wherein selection can be made by using a cell surface marker, for example, to select overexpression of the marker by fluorescence activated cell sorting (FACS). In another specific, non-limiting example of a selectable marker is a protein, or a gene encoding a protein, that can be identified in a cell based on its fluorescent or enzymatic properties. Specific, non-limiting examples include, but are not limited to, enhanced fluorescent green protein (EGFP), alkaline phosphatase, or horseradish peroxidase. A marker can also be a polypeptide or antigenic epitope thereof, wherein an antibody that specifically binds the polypeptide can be used to identify cells that express the polypeptide or antigenic epitope. One specific, non-limiting example of a polypeptide of use is human growth Hormone (hGH).

Membrane potential: The electrical potential of the interior of the cell with respect to the environment, such as an external bath solution. One of skill in the art can readily assess the membrane potential of a cell, such as by using conventional whole cell techniques. Activation of a cell is associated with less negative membrane potentials (for example shifts from about −50 mV to about −40 mV). These changes in potential increase the likelihood of action potentials, and thus lead to an increase in the rate of action potentials.

The rate of action potentials can be assessed using many approaches, such as using conventional whole cell access, or using, for example, perforated-patch whole-cell and cell-attached configurations. In each event the absolute voltage or current is not assessed, rather the frequency of rapid deflections characteristic of action potentials is assessed, as a function of time (therefore this frequency is an instantaneous frequency, reported in “bins”). This time component can be related to the time at which a compound, such as a PYY agonist, is applied to the bath to analyze the effect of the compound, such as the PYY agonist, on action potential firing rate.

Neuropeptide Y (NPY): A 36-amino acid peptide that is a neuropeptide identified in the mammalian brain. NPY is believed to be an important regulator in both the central and peripheral nervous systems and influences a diverse range of physiological parameters, including effects on psychomotor activity, food intake, central endocrine secretion, and vasoactivity in the cardiovascular system. High concentrations of NPY are found in the sympathetic nerves supplying the coronary, cerebral, and renal vasculature and have contributed to vasoconstriction. NPY binding sites have been identified in a variety of tissues, including spleen, intestinal membranes, brain, aortic smooth muscle, kidney, testis, and placenta. In addition, binding sites have been reported in a number of rat and human cell lines.

NPY binds to several receptors, including the Y1, Y2, Y3, Y4 (PP), Y5, Y6, and Y7 receptors. These receptors are recognized based on binding affinities, pharmacology, and sequence (if known). Most, if not all of these receptors are G protein coupled receptors. One of skill in the art can readily determine the dissociation constant ($K_d$) value of a given compound for a Y receptor. This value is dependent on the selectivity of the compound tested. For example, a compound with a $K_d$ which is less than 10 nM is generally considered an excellent drug candidate. However, a compound that has a lower affinity, but is selective for the particular receptor, can also be a good drug candidate. In one specific, non-limiting example, an assay, such as a competition assays, is used to determine if a compound of interest is a Y2 receptor agonist. Assays useful for evaluating neuropeptide Y receptor antagonists are also well known in the art (see U.S. Pat. No. 5,284,839, which is herein incorporated by reference, and Walker et al., *Journal of Neurosciences* 8:2438-2446, 1988).

Oligonucleotide: A linear polynucleotide sequence of up to about 200 nucleotide bases in length, for example a polynucleotide (such as DNA or RNA) which is at least 6 nucleotides, for example at least 15, 50, 100 or even 200 nucleotides long.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

Polylinker: An artificial nucleic acid sequence of about twenty to thirty nucleotides in length that is designed to include restriction sites cleaved by several restriction enzymes. A specific non-limiting example of a polylinker is: 5'-GCCCGGGCTCGAGTTTAAAGCGCGC-3' (SEQ ID NO: 36), that includes the restrictions sites for SrfI, SmaI, XhoI, DraI, and, BssHII.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" as used herein are intended to encompass any amino acid sequence and include modified sequences such as glycoproteins. The term "polypeptide" is specifically intended to cover naturally occurring proteins, as well as those which are recombinantly or synthetically produced. The term "polypeptide fragment" refers to a portion of a polypeptide, for example such a fragment which exhibits at least one useful sequence in binding a receptor. The term "functional fragments of a polypeptide" refers to all fragments of a polypeptide that retain an activity of the polypeptide. Biologically functional peptides can also include fusion proteins, in which the peptide of interest has been fused to another peptide that does not decrease its desired activity.

Promoter: An array of nucleic acid control sequences which direct transcription of a nucleic acid. In one embodiment, a promoter includes necessary nucleic acid sequences near the start site of transcription, such as, in the case of a polymerase II type promoter, a TATA element. Enhancer and repressor elements can be located adjacent to, or distal to the sequences necessary for the start site of transcription, and can be located as much as several thousand base pairs from the start site of transcription. A "heterologous promoter" is a promoter from one gene operably linked to a control element or a protein coding sequence from another gene or another species of animal. In one specific, non-limiting example, a POMC enhancer is operably linked to a heterologous promoter (e.g. a promoter that is not from a POMC gene from the same species of animal), such as an SV40, thymidine kinase, beta actin, tyrosine hydroxylase, or other promoter. In another specific non-limiting example, a heterologous promoter is not a POMC promoter.

A promoter can be a "strong" promoter, which promotes transcription of RNA at high levels, for example at levels such that the transcriptional activity of the promoter generally accounts for about 25% of transcriptional activity of all transcription within a cell. The strength of a promoter is often tissue-specific and thus can vary from one cell type to another. For example, the promoter of the human cytomegalovirus early gene 1 is a classic strong promoter because it generates high levels of transcriptional activity in many cell types.

In other embodiments, the promoter is a "tissue-specific promoter," which promotes transcription in a single cell type or narrow range of tissues. In one embodiment, a tissue specific promoter promotes expression in the pituitary and/or the hypothalamus, but not in other tissues. In another embodiment, a tissue specific promoter promotes expression in the pituitary, but not in other tissues. In a further embodiment, a tissue specific promoter promotes expression only in a limited subset of neurons (e.g. in the arcuate nucleus of the hypothalamus and nucleus tractus solitarius), but not in other tissues (e.g., heart, lung, pancreas, intestines, skin, etc.)

In other embodiments, the promoter is a "minimal" promoter, which has very low intrinsic transcriptional activity in the absence of operably linked enhancer sequences. A minimal promoter is one that does not have inherent cell-specific or tissue-specific activity, but may direct transcriptional initiation in multiple eukaryotic cell types when operably linked to a cell- or tissue-specific enhancer sequence. One specific, non-limiting example of a minimal promoter is the minimal promoter sequences of the herpes simplex virus type 1thymidine kinase (HSV1-tk) gene.

A "POMC promoter" is the array of nucleic acid control sequences that direct transcription of a POMC nucleic acid in the endogenous chromosomal location of a species of interest. In one embodiment, a POMC promoter includes necessary nucleic acid sequences near the start site of transcription, such as a polymerase II type promoter, a TATA element, and a SP1 site. In one specific, non-limiting example, in the rat, the POMC promoter is located at the 5' end of the rat POMC gene. In one specific, non-limiting example the rat POMC promoter is the approximately 700, or approximately 400, base pairs immediately 5' of the transcription start site (Hammer et al., *Molec. Endocrinol.* 4:1689, 1990), such as the sequence located from −323 to −34. The rat POMC promoter cooperatively directs transcription to corticotrophs and melanotrophs in transgenic mice. In the rat, the activator SP1 interacts with a GC-rich region in the promoter (see Liu et al., *Biochem. J.* 312:827-832, 1995).

Proopiomelanocortin (POMC): A glycosylated protein of a molecular weight of 31 kDa. POMC has been demonstrated to be synthesized mainly in the anterior pituitary, in the hypothalamus, and in the brainstem. However, other tissues, cell types, or neurons also express the POMC gene, albeit at lower levels. This protein is a precursor protein, post-translational processing of POMC yields several neuroactive peptides upon specific cleavage. The POMC coding sequence includes the amino acid sequences of adrenocorticotropic (ACTH) hormone and beta-lipotropin. ACTH is processed to produce the polypeptides melanotropin (alpha-MSH) and corticotrophin-like intermediate lobe peptide (CLIP). Beta-lipotropin is processed to produce the peptides γ-lipotropin, beta-endorphins, and beta-melanocyte stimulating hormone (β-MSH). The amino-terminal fragment of POMC is processed to a family of gamma-MSH peptides and to a peptide with putative mitogenic stimulatory activity of the adrenal cortical cells. The biological activity of POMC-derived peptides is further regulated in a tissue-specific manner by acetylation of the amino-terminal amino acid residue and/or amidation of the carboxyterminal amino acid residue by the enzyme peptidyl-α-monooxygenase (PAM).

The POMC gene (human chromosome 2p23) contains three exons and two introns: one, of about 3.5 kb, interrupts the N-terminal fragment of the common precursor mostly encoded in exon 3. Exon 2 contains the sequence for a portion of the 5' untranslated portion of the mRNA, all of the signal sequence which directs insertion of the precursor protein into the endoplasmic reticulum, and 8 amino acids of the N-terminal fragment. The overall arrangement of introns and exons in the POMC gene is almost identical in all mammalian species. Hormonal control of POMC gene transcription and release of peptide products derived from the POMC precursor is tissue-specific; for example, glucocorticoids specifically inhibit anterior but not intermediate pituitary POMC transcription.

Purified: The term purified does not require absolute purity; rather, it is intended as a relative term. Thus, for example, a purified protein preparation is one in which the protein is more pure than the protein in its natural environment within a cell. Such proteins may be produced, for example, by standard purification techniques, or by recombinant expression. In some embodiments, a preparation of a protein is purified such that the protein represents at least 50%, for example at least 70%, of the total protein content of the preparation.

PYY: A peptide YY polypeptide obtained or derived from any species. Thus, PYY includes the human full length polypeptide (as set forth in SEQ ID NO: 1) and species variations of PYY, including e.g. murine, hamster, chicken, bovine, rat, and dog PYY. In one embodiment, PYY agonists do not include NPY. A “PYY agonist” is any compound which binds to a receptor that specifically binds PYY, and elicits an effect of PYY. In one embodiment, a PYY agonist is a compound that affects food intake, caloric intake, or appetite, and/or which binds specifically in a Y receptor assay or competes for binding with PYY, such as in a competitive binding assay with labeled PYY. PYY agonists include, but are not limited to, compounds that bind to the Y2 receptor.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g. by genetic engineering techniques, such as those described in Sambrook et al. (in *Molecular Cloning: A Laboratory Manual*, Cold Spring Harbor, N.Y., 1989).

Restriction Enzyme: An enzyme that cleaves a specific nucleic acid sequence. A restriction enzyme usually recognizes a specific short sequence of bases in the DNA. Different restriction enzymes recognize different sequences, i.e., they have different specificities. Consequently, restriction enzymes allow DNA to be cleaved at specific, pre-determined locations. The sequence which a restriction enzyme recognizes and digests the nucleic acid is called a restriction site. The process of cutting the DNA is called a restriction digest or a digestion. Specific, non-limiting examples of restriction sites are EcoR I or Bgl II, or a StuI site, where the first part of the name refers to the strain of bacteria which was the source of the enzyme (e.g., *Escherichia coli* RY 13) and the second part of the name is a Roman numeral.

Sequence identity: The similarity between amino acid sequences is expressed in terms of the percentage of conservation between the sequences, otherwise referred to as sequence identity. Sequence identity is frequently measured in terms of percentage identity (or similarity or homology); the higher the percentage, the more similar the two sequences are. Homologues or variants of a POMC sequence will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.*, 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the Internet, for use in connection with the sequence analysis programs blastp, blastn, blastx, tblastn and tblastx. A description of how to determine sequence identity using this program is available on the NCBI website on the internet. Other specific, non-limiting examples of sequence alignment programs specifically designed to identify conserved regions of genomic DNA of greater than or equal to 100 nucleotides are PIPMaker (Schwartz et al., *Genome Research* 10: 577-586, 2000) and DOTTER (Erik et al., *Gene* 167: GC1-10, 1995).

Homologues and variants of a POMC enhancer sequence are typically characterized by possession of at least 75%, for example at least 80%, 90%, 95%, 98%, or 99%, sequence identity counted over the full length alignment with the originating POMC enhancer sequence using the NCBI Blast 2.0, set to default parameters. Methods for determining sequence identity over such short windows are available at the NCBI website on the internet. One of skill in the art will appreciate that these sequence identity ranges are provided for guidance only; it is entirely possible that strongly significant homologues could be obtained that fall outside of the ranges provided.

Substantially purified: A polypeptide which is substantially free of other proteins, lipids, carbohydrates or other materials with which it is naturally associated. For example, the polypeptide may be at least 50%, 80% or 90% free of other proteins, lipids, carbohydrates or other materials with which it is naturally associated.

TATA box: An upstream promoter element; a DNA conserved sequence TATAAA that is generally located −25 to −30 base pairs relative to the transcriptional start site. This sequence is part of the promoter sequence of eukaryotic genes and binds transcription factor IID (TFIID). RNA polymerase recognizes the TFIID-TATA protein-DNA complex. The TATA box sequence is critical both for promoter activity and for determining the exact point of RNA chain initiation. For example, in the human POMC gene the sequence of the TATA box is TATATAA and is located 28 bases 5' to the transcriptional start site. In the mouse POMC gene the TATA box sequence is TATAAAA and is located 30 bases 5' of the transcriptional start site.

Transcriptional enhancement: A property of producing an increase in the rate of transcription of linked sequences that contain a functional promoter.

Transcriptional unit: A polynucleotide sequence that includes the entire coding region, including all exons and introns, the translational start and stop codons, and the cleavage and polyadenylation consensus sequence.

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' of the 5' end of the RNA transcript are referred to as "upstream sequences"; sequence regions on the DNA strand having the same sequence as the RNA and which are 3' to the 3' end of the RNA transcript are referred to as "downstream sequences".

Transduced and Transfected: A virus or viral vector transduces a cell when it transfers nucleic acid into the cell. A cell is "stably transduced" by a nucleic acid transduced into the cell when the DNA becomes stably replicated by the cell, either by incorporation of the nucleic acid into the cellular genome, or by episomal replication. As used herein, the terms transduced and transfected encompass all techniques by which a nucleic acid molecule might be introduced into such a cell, including transfection with viral vectors, transfection with plasmid vectors, and introduction of naked DNA by electroporation, lipofection, injection, and particle gun acceleration.

Transgene: A foreign gene that is placed into an organism by introducing the foreign gene into embryonic stem (ES) cells, newly fertilized eggs or early embryos. In one embodiment, a transgene is a gene sequence, for example a sequence that encodes a marker polypeptide that can be detected using methods known to one of skill in the art. In another embodiment, the transgene encodes a therapeutic polypeptide that can be used to alleviate or relieve a symptom of a disorder. In yet another embodiment, the transgene encodes a therapeutically effective oligonucleotide, for example an antisense oligonucleotide, wherein expression of the oligonucleotide inhibits expression of a target nucleic acid sequence. In a further embodiment, the transgene encodes an antisense nucleic acid or a ribozyme. In yet another embodiment, a transgene is a stop cassette.

In other embodiments, a transgene contains regulatory sequences (e.g. an enhancer, such as a POMC enhancer) operably linked to a transcriptional unit. Thus, the transgene can include regulatory sequences operably linked to a nucleic acid sequence encoding a polypeptide, such as a marker.

Transgenic Cell: Cells that contain foreign, non-native DNA.

Transgenic Animal: An animal, for example, a non-human animal such as a mouse, that has had DNA introduced into one or more of its cells artificially. By way of example, this is commonly done by random integration or by targeted insertion. DNA can be integrated in a random fashion by injecting it into the pronucleus of a fertilized ovum. In this case, the DNA can integrate anywhere in the genome, and multiple copies often integrate in a head-to-tail fashion. There is no need for homology between the injected DNA and the host genome. In most cases, the foreign transgene is transmitted to subsequence generations in a Mendelian fashion (a germ-line transgenic).

Targeted insertion, the other common method of producing transgenic animals, is accomplished by introducing the DNA into embryonic stem (ES) cells and selecting for cells in which the DNA has undergone homologous recombination with matching genomic sequences. For this to occur, there often are several kilobases of homology between the exogenous and genomic DNA, and positive selectable markers are often included. In addition, negative selectable markers are often used to select against cells that have incorporated DNA by non-homologous recombination (random insertion).

Vector: A nucleic acid molecule used to introduce foreign DNA into a cell, thereby producing a transfected cell. A vector can include nucleic acid sequences that permit it to replicate in the cell, such as an origin of replication. A vector can also include one or more marker or therapeutic transgenes and other genetic elements known in the art.

In some embodiments, the vector is a non-viral vector, such as a bacterial plasmid vector. In other embodiments, the vector is a viral vector. Examples of viral vectors include, but are not limited to adenoviral vectors, retroviral vectors, and Herpes viral vectors.

Voltage: An electric potential or potential difference, expressed in volts.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." All publications, patent applications, patents, and other references mentioned herein are incorporated by reference in their entirety. In case of conflict, the present specification, including explanations of terms, will control. In addition, the materials, methods, and examples are illustrative only and not intended to be limiting.

POMC Enhancer Elements

POMC neurons of the hypothalamus are critical components of the neural circuitry controlling appetite, feeding, and metabolism. In addition, POMC-derived peptides synthesized in neurons of the central nervous system participate in the control of body temperature, blood pressure, stress-induced analgesia, reproductive function, cognitive abilities, emotional states, rewarding behavior, responses to drugs of abuse, including opioids and ethanol, and neuroimmunomodulation. They also modulate the activity of other hypothalamic neurons which control reproduction, thyroid hormone levels, growth hormone secretion, prolactin secretion, and neuroendocrine stress responses. These neurons also are involved in the nervous system's endogenous analgesic and reward circuits.

Figure 10C:
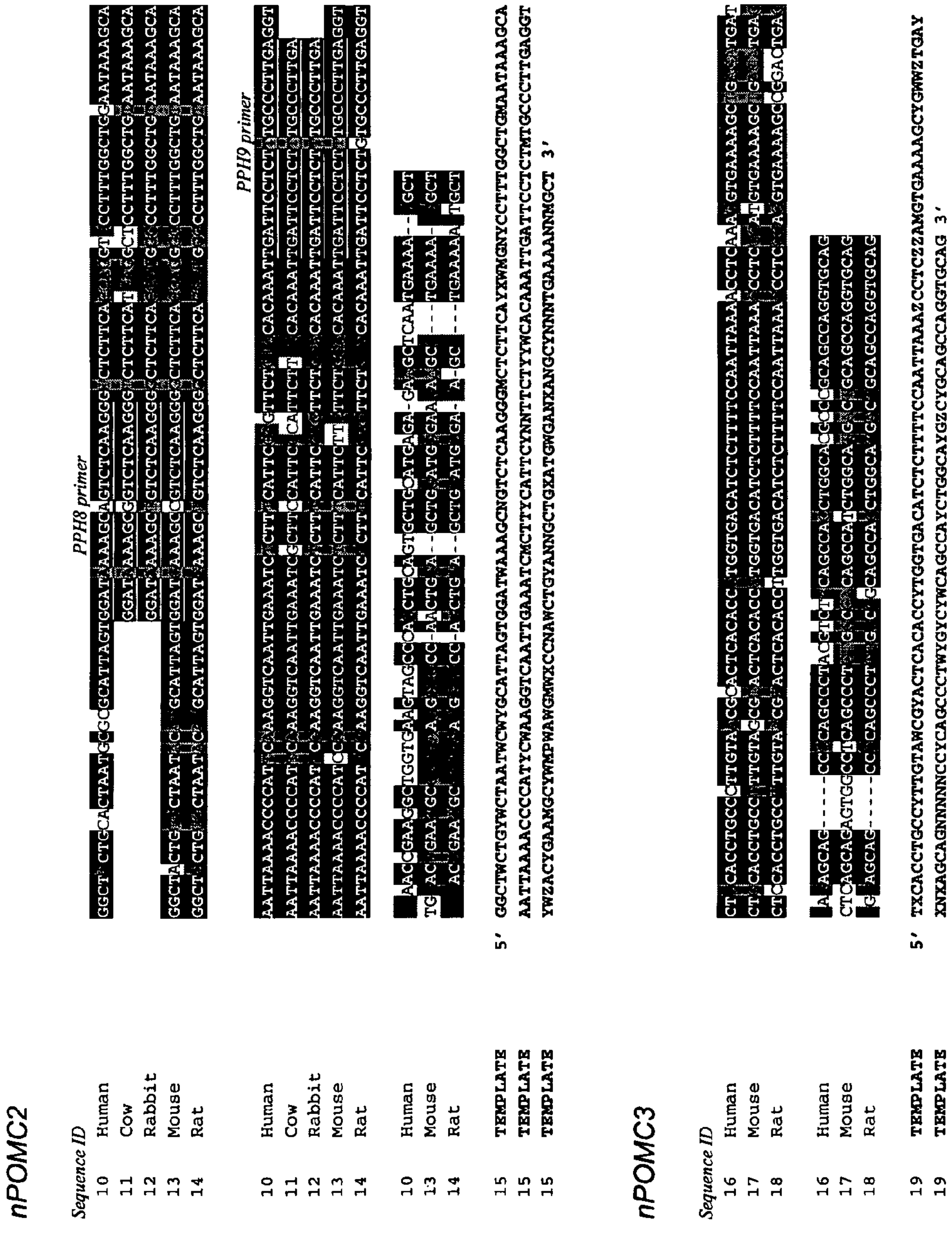
FIG. 10 is the sequence alignments of nPOMC1 (FIG. 10*a*) (5' half, human (SEQ ID NO: 1), cow (SEQ ID NO: 2), hamster (SEQ ID NO: 3), mouse (SED ID NO: 4), and rat (SEQ ID NO: 5)), nPOMC1 (FIG. 10*b*) (3' half, human (SEQ ID NO: 6), mouse (SEQ ID NO: 7), and rat (SEQ ID NO: 8)), nPOMC1 complete template (SEQ ID NO: 9) and nPOMC2 (FIG. 10*c*) (human (SEQ ID NO: 10), cow (SEQ ID NO: 11), rabbit (SEQ ID NO: 12), mouse (SEQ ID NO: 13), and rat (SEQ ID NO: 14)), nPOMC2 template (SEQ ID NO: 15) and nPOMC3 (FIG. 10*c*) (human (SEQ ID NO: 16), mouse (SEQ ID NO: 17), and rat (SEQ ID NO: 18)), and nPOMC3 template (SEQ ID NO: 19). PPH2 and PPH3 primers (underlined) were designed based on the sequences of human and mouse nPOMC1 (5' half) and used to amplify the corresponding sequences from cow and hamster genomic DNA. PPH8 and PPH9 primers (underlined) were designed based on the sequences of human and mouse nPOMC2 and used to amplify the corresponding sequences from cow and rabbit genomic DNA. The consensus binding site for STAT3 (TTCCNGGAA) is shown adjacent to putative STAT3 binding sites within the nPOMC1 (3' half) element. In the templates shown, in addition to the standard nucleotides (A, G, C, T) M=G/T, N=any nucleotide or a blank, P=A/T, W=A/G, X=C/G, Y=C/T, Z=A/C.

Disclosed herein are the sequences of several mammalian POMC enhancer elements. These sequences are of use in directing expression of a gene product to the POMC neurons. Generally, a POMC enhancer includes at least one NPOMC1, nPOMC2, or an nPOMC3 element. A POMC enhancer can also include at least two nPOMC1, nPOMC2, or nPOMC3 elements. A POMC enhancer can also include an nPOMC1, nPOMC2, and an nPOMC3 element. Templates for nPOMC1 (SEQ ID NO: 9), nPOMC2 (SEQ ID NO: 15) and nPOMC3 (SEQ ID NO: 19) are shown in FIGS. 10*a*-10*c*. The sequences of several exemplary nPOMC1, nPOMC2, and nPOMC3 elements are also shown in FIGS. 10*a-c*. Transgenes including a POMC enhancer element are diagrammed in FIG. 7.

In one specific, non-limiting example, the enhancer is approximately 4 kilobases in length that is located upstream of the POMC coding sequences of the endogenous chromosomal of the mammal of interest. In other specific, non-limiting examples, the enhancer includes an nPOMC1 element and an nPOMC2 element, an nPOMC1 element and an nPOMC3 element, an nPOMC2 and an nPOMC3 element, or an nPOMC1, nPOMC2, and an nPOMC3 element. Generally, any combination of these elements is of use, provided they direct expression to POMC neurons. In yet another specific, non-limiting example, a POMC enhancer does not include a POMC promoter. Generally, a POMC promoter includes necessary nucleic acid sequences near the start site of transcription, such as a polymerase II type promoter, a TATA element, and a SP1 site near the POMC start of transcription (as measured from the endogenous chromosomal location). In one specific, non-limiting example, in the rat, the POMC promoter is located at the 5' end of the rat POMC protein coding sequences. In one specific, non-limiting example the rat POMC promoter is the approximately 700, or approximately 400, base pairs immediately 5' of the transcription start site (Hammer et al., *Molec. Endocrinol.* 4:1689, 1990), such as the sequence located from −323 to −34. The rat POMC promoter cooperatively directs transcription to corticotrophs and melanotrophs in transgenic mice. Similarly, sequences from the mouse POMC gene containing 2 kb of 5' flanking region (Rubinstein et al., *Neuroendocrinology* 58:373-380; 1993) or from the human POMC gene promoter containing 2.9 kb of the 5' flanking region of the human gene (Tsukada et al., *DNA Cell Biol.* 13:755-762; 1994) are active in pituitary cells.

A template for the complete nPOMC1 sequence based on sequence comparisons among multiple mammalian species is set forth as SEQ ID NO: 9. In one embodiment, an nPOMC1 sequence is at least 90% identical to SEQ ID NO: 9, such as a sequence 95% identical, 98% identical, or 99% identical to SEQ ID NO: 9. In another embodiment, an nPOMC1 sequence includes at most fifty conserved enhancer substitutions of SEQ ID NO: 9, such as, but not limited to, at most about two, at most about five, at most about ten, at most about twenty, or at most about fifty conserved enhancer substitutions of SEQ ID NO: 9.

Several specific nPOMC1 elements are disclosed herein. These sequences include the 5' half of the nPOMC element, which includes SEQ ID NO: 1, SEQ ID NO: 2, SEQ ID NO: 3, SEQ ID NO: 4 and SEQ ID NO: 5. These sequences can also include the 3' half of an nPOMC1 element, as set forth as SEQ ID NO: 6, SEQ ID NO: 7, and SEQ ID NO: 8. In one embodiment, an nPOMC1 sequence also includes the 3' half of the element, as set forth as SEQ ID NO: 6, SEQ ID NO: 7, and SEQ ID NO: 8. In several embodiments, an nPOMC1 sequence includes SEQ ID NO: 1 and SEQ ID NO: 6, SEQ ID NO: 4 and SEQ ID NO: 7, or SEQ ID NO: 5 and SEQ ID NO: 8. In other embodiments, the nPOMC1 element includes any one of SEQ ID NOs: 1-5 in combination with any one of SEQ ID NOs: 6-8.

It should be noted that modifications can be made in these sequences that do not alter their ability to direct expression of a heterologous gene in POMC neurons. Modifications include substitutions, insertions, and/or deletions of nucleic acid residues. Although these POMC sequences do not encode proteins, and thus do not fit under the classical definition of conservative substitutions (see above), these substitutions can be considered "conserved enhancer" substitutions. In several specific, non-limiting examples, conserved enhancer substitutions include at most fifty, such as at most about one, at most about two, at most about five, at most about ten, or at most about twenty substitutions in any one of SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8. In other specific, non-limiting examples, conserved enhancer substitutions include at most one, at most two, at most five, at most ten, or at most twenty deletions in any one of SEQ ID NO: 1, SEQ ID NO: 2, SEQ ID NO: 3, SEQ ID NO: 4, SEQ ID NO: 5, SEQ ID NO: 6, SEQ ID NO: 7 or SEQ ID NO: 8.

As shown in FIGS. 10*a*-10*b*, several conserved areas of nPOMC1 have been identified (see black and gray boxes). Thus, in several specific, non-limiting examples, conserved enhancer substitutions include at most one, at most two, at most five, at most ten, or at most twenty substitutions outside of conserved areas any one of SEQ ID NO: 1, SEQ ID NO: 2, SEQ ID NO: 3, SEQ ID NO: 4 and SEQ ID NO: 5, SEQ ID NO: 6, SEQ ID NO: 7 or SEQ ID NO: 8. For example, in SEQ ID NO: 1, the first nucleic acid reside (a guanine, G), can be replaced by a cytosine (C), adenine (A), or thymine (T). Similarly, in SEQ ID NO: 1, the first nucleic acid residue can be deleted, yet the sequence can still be used to appropriately direct expression in a POMC neuron. Similarly, the third nucleic acid residue, "A," can be replaced by a G, C, or T, as long as the nucleic acid sequence can be used to appropriately direct expression to a POMC neuron. In another example, nucleic acid residue 21 in SEQ ID NO: 2, "T" can be replaced by an A, G, C, or deleted. In addition, other nucleic acid elements can be added to these sequences without interfering with their function, such as promoter sequences.

In another embodiment, an nPOMC1 sequence of use includes an element at least about 70% homologous with the corresponding originating POMC sequence. For example, a sequence at least 80%, at least 90%, at least 95%, at least 98%, or at least 99% homologous with the corresponding originating POMC sequence, such as SEQ ID NO: 1, SEQ ID NO: 2, SEQ ID NO: 3, SEQ ID NO: 4, and SEQ ID NO: 5, SEQ ID NO: 6, SEQ ID NO: 7, or SEQ ID NO: 8. In one specific, non-limiting example, identical regions (shown in black, FIGS. 10*a-b*) are retained. In other, specific, non-limiting examples identical regions between two or more (shown in gray are retained). In a further, non-limiting example, non-conserved regions (shown white) are substituted to create the sequences with the desired identity to the originating sequences.

A template for the complete nPOMC2 sequence based on sequence comparisons among multiple mammalian species is set forth as SEQ ID NO: 15. In one embodiment, an nPOMC2 sequence is about 90% identical to SEQ ID NO: 17, such as about 95% identical, 98% identical, or 99% identical to SEQ ID NO: 15. In another embodiment, an nPOMC2 sequence includes at most twenty conserved enhancer substitutions of SEQ ID NO: 15, such as at most two, at most five, at most ten, or at most fifteen conserved enhancer substitutions of SEQ ID NO: 15.

Several specific nPOMC2 elements are disclosed herein. These sequences include, but are not limited to, SEQ ID NO: 10, SEQ ID NO: 11, SEQ ID NO: 12, SEQ ID NO: 13, and SEQ ID NO: 14. It should be noted that modifications can be made in these nPOMC2 sequences that do not alter their ability to direct expression of a heterologous gene in POMC neurons. Modifications include substitutions, insertions, and/or deletions of nucleic acid residues. In several specific, non-limiting examples, conserved enhancer substitutions include at most twenty conserved enhancer substitutions, such as at most one, at most two, at most five, at most ten, or at most fifteen substitutions in any one of SEQ ID NO: 10, SEQ ID NO: 11, SEQ ID NO: 12, SEQ ID NO: 13, and SEQ ID NO: 14. In other specific, non-limiting examples, conserved enhancer substitutions include at most one, at most two, at most five, at most ten, or at most twenty deletions in any one of SEQ ID NO: 10, SEQ ID NO: 11, SEQ ID NO: 12, SEQ ID NO: 13, and SEQ ID NO: 14.

As shown in FIG. 10*c*, several conserved areas of nPOMC2 have also been identified (see black and gray boxes). Thus, in several specific, non-limiting examples, conserved enhancer substitutions include at most one, at most two, at most five, at most ten, or at most twenty substitutions outside of conserved areas any one of SEQ ID NO: 10, SEQ ID NO: 11, SEQ ID NO: 12, SEQ ID NO: 13, and SEQ ID NO: 14. For example, in SEQ ID NO: 10, the fourth nucleic acid residue (a thymine, T) can be replaced by a cytosine (C), adenine (A), or guanine (G). Similarly, in SEQ ID NO: 11, the eleventh nucleic acid residue can be deleted, yet the sequence can still be used to appropriately direct expression in a POMC neuron. Similarly, the eleventh nucleic acid residue in SEQ ID NO: 11, “G,” can be replaced by an A, C, or T, as long as the nucleic acid sequence can be used to appropriately direct expression to a POMC neuron. In another example, nucleic acid residue 9 in SEQ ID NO: 13, “T” can be replaced by an A, G, C or deleted. In addition, other nucleic acid elements can be added to these sequences without interfering with their function, such as, but not limited to, promoter sequences.

In another embodiment, an nPOMC2 sequence of use includes an element at least 70% homologous with the corresponding originating nPOMC2 sequence. For example, a sequence at least 80%, at least 90%, at least 95%, at least 98%, or at least 99% homologous with the corresponding originating nPOMC2 sequence, such as SEQ ID NO: 10, SEQ ID NO: 11, SEQ ID NO: 12, SEQ ID NO: 13, and SEQ ID NO: 14. In one specific, non-limiting example, identical regions (shown in black, FIG. 10*c*) are retained. In other, specific, non-limiting examples identical regions between two or more (shown in gray are retained). In a further, non-limiting example, non-conserved regions (shown white) are substituted to create the sequences with the desired identity to the originating sequences.

A template for the complete nPOMC3 sequence based on sequence comparisons among multiple mammalian species is set forth as SEQ ID NO: 9. In several examples, an nPOMC3 sequence is at least about 90% identical to SEQ ID NO: 19. In other examples, an nPOMC sequence is about 95% identical, 98% identical, or 99% identical to SEQ ID NO: 19. In another embodiment, an nPOMC3 sequence includes at most fifteen conserved enhancer substitutions of SEQ ID NO: 19, such as at most 2, at most 5, at most ten, at most twelve conserved enhancer substitutions of SEQ ID NO: 19.

Several specific nPOMC3 elements are disclosed herein. These sequences include, but are not limited to, SEQ ID NO: 16, SEQ ID NO: 17, and SEQ ID NO: 18. It should be noted that modifications can be made in these nPOMC3 sequences that do not alter their ability to direct expression of a heterologous gene in POMC neurons. As described above, modifications include substitutions, insertions, and/or deletions of nucleic acid residues. In several specific, non-limiting examples, conserved enhancer substitutions include at most about twenty substitutions, such as at most one, at most two, at most five, at most ten, or at most fifteen substitutions in SEQ ID NO: 16, SEQ ID NO: 17, or SEQ ID NO: 18. In other specific, non-limiting examples, conserved enhancer substitutions include at most one, at most two, at most five, at most ten, or at most twenty deletions in any one of SEQ ID NO: 16, SEQ ID NO: 17, or SEQ ID NO: 18.

As shown in FIG. 10*c*, several conserved areas of nPOMC3 have also been identified (see black or gray boxes). Thus, in several specific, non-limiting examples, conserved enhancer substitutions include at most one, at most two, at most five, at most ten, or at most twenty substitutions outside of conserved areas of SEQ ID NO: 16, SEQ ID NO: 17, or SEQ ID NO: 18. For example, in SEQ ID NO: 16, the first nucleic acid residue a “C,” can be replaced by a G, T, or an A, and/or the second nucleic acid residue, a “T,” can be replaced by a G, A, or a C, and/or the third nucleic acid residue, a “G,” can be replaced by an A, T, or C. Alternatively, the first, second, and/or third nucleic acid residues can be deleted. Similarly, in SEQ ID NO: 17, the first nucleic acid reside a “C,” can be replaced by a G, T, or an A, and/or the second nucleic acid residue, a “T,” can be replaced by an A, G, or a C, and/or the third nucleic acid residue, a “G,” can be replaced by an A, T, or C, as long as the sequence can still be used to appropriately direct expression in a POMC neuron. In addition, other nucleic acid elements can be added to these sequences without interfering with their function, such as, but not limited to, promoter sequences.

In another embodiment, an nPOMC3 sequence of use includes an element at least 70% homologous with the corresponding originating POMC sequence. For example, a sequence at least 80%, at least 90%, at least 95%, at least 98%, or at least 99% homologous with the corresponding originating POMC sequence, such as SEQ ID NO: 16, SEQ ID NO: 17, or SEQ ID NO: 18. In one specific, non-limiting example, identical regions (shown in black, FIG. 10*c*) are retained. In other, specific, non-limiting examples identical regions between two or more (shown in gray are retained). In a further, non-limiting example, non-conserved regions (shown white) are substituted to create the sequences with the desired identity to the originating sequences.

In several other embodiments, an isolated POMC enhancer includes several kilobases (kb) of sequence 5' (upstream) of the POMC promoter and the transcription start site (which is generally considered to start at nucleotide 1 of the coding sequence) of the POMC gene. Thus, in one specific, non-limiting example, a POMC enhancer includes the nucleotide sequences from about −13 kilobases relative to the transcription start site and the transcription start site. This genomic fragment of about 13 kb directs eutopic expression of operably linked genes to neurons of the arcuate nucleus of the hypothalamus and the nucleus of the tractus solitarius and to pituitary corticotrophs and melanotrophs, all cell types where the endogenous POMC gene is normally expressed.

In another specific, non-limiting example, a POMC enhancer includes the nucleotide sequences from about −13 kilobases to about −0.7 kilobases relative to the transcription start site of the mouse POMC gene or equivalent mammalian gene sequence (e.g. mouse, rat, cow, hamster or human sequence). In a further specific, non-limiting example, a POMC enhancer includes the nucleotide sequence located between about −9 kilobases to about −0.7 kilobases relative to the transcription start site of a mouse proopiomelanocortin gene, or any other mammalian species (e.g. rat, cow, hamster, human, etc.). In a further specific, non-limiting example, a POMC enhancer includes the nucleotide sequence located from about −13 kilobases to about −6.5 kilobases of an upstream region of a start site of a proopiomelanocortin protein coding sequence. In yet another non-limiting example, a POMC enhancer includes the nucleotide sequence located from about −13 kilobases to about −9 kilobases of an upstream region relative to the transcription start site of a mouse proopiomelanocortin gene, or any other mammalian species (e.g. rat, cow, hamster, human, etc.). Each of these enhancers direct eutopic expression of operably linked genes to neurons of the arcuate nucleus of the hypothalamus and the nucleus of the tractus slitarius, and/or to pituitary corticotrophs and melanotrophs. All of these cell types express the endogenous POMC gene.

A human large genomic contig (Homo sapiens chromosome 2 reference contig) including the complete POMC gene and the nPOMC1, nPOMC2 and nPOMC3 elements can be found in GenBank, the NIH sequence database maintained by the National Center for Biotechnology Information (NCBI). The information relating to this sequence is as follows: Accession No.: NT_005204.

A mouse large genomic contig (*Mus musculus* chromosome 12 WGS supercontig) including the complete POMC gene and the nPOMC1, POMC2 and nPOMC3 elements) can also be found in GenBank. The information relating to this sequence is as follows: Accession No.: NW_000041.

A rat large genomic contig (*Rattus norvegicus* chromosome 6 WGS supercontig) including the complete POMC gene and the nPOMC1, POMC2 and nPOMC3 elements) can also be found in GenBank. The information relating to this sequence is as follows: Accession No.: NW_043940.

All these GenBank entries (human, mouse, and rat) are incorporated herein by reference in their entirety. Using the information provided herein, and the information provided in GenBank, one of skill in the art can readily isolate the relevant sequences.

The POMC enhancer sequences described above can be obtained by many methods. The more common include chemical synthesis by known methods such as phosphotriester, phosphite, or phosphoramidite chemistry, using solid phase techniques such as described in EP 266,032 published May 4, 1988, or deoxynucleoside H-phosphonate intermediates as described by Froehler et at., *Nucl. Acids Res.* 14:5399-5407, 1986. A POMC enhancer sequences can also be amplified directly from the genomic DNA using the polymerase chain reaction (PCR) as described in U.S. Pat. No. 4,683,195 issued Jul. 28, 1987. Finally, the desired nucleotide sequence (whether double or single stranded) can be readily synthesized by any number of commercial suppliers such as Genset (San Diego, Calif.) or Clontech (Palo Alto, Calif.). Commercial suppliers, as well as anyone synthesizing or PCR amplifying the sequence themselves, can create the sequences with particular requested overhangs to match any particular cloning needs.

Expression Systems

A POMC enhancer can be included in an expression vector to direct expression of a heterologous nucleic acid sequence. Thus other expression control sequences including appropriate promoters, transcription terminators, a start codon (i.e., ATG) in front of a protein-encoding gene, splicing signal for introns, maintenance of the correct reading frame of that gene to permit proper translation of mRNA, and stop codons can be included with a POMC enhancer in an expression vector. Generally expression control sequences include a promoter, a minimal sequence sufficient to direct transcription.

The expression vector typically contains an origin of replication, a promoter, as well as specific genes which allow phenotypic selection of the transformed cells. Vectors suitable for use include, but are not limited to the pMSXND expression vector for expression in mammalian cells (Lee and Nathans, *J. Biol. Chem.* 263:3521, 1988). Generally, the expression vector will include a promoter. The promoter can be inducible or constitutive. The promoter can be tissue specific. Suitable promoter include the thymidine kinase promoter (TK), metallothionein I, polyhedron, neuron specific enolase, tyrosine hydroxylase, beta-actin, or other promoters. In one embodiment the promoter is a POMC promoter. In another embodiment, the promoter is a heterologous promoter.

In one example, the POMC enhancer is located upstream of the desired promoter, but enhancer elements can generally be located anywhere on the vector and still have an enhancing effect. However, the amount of increased activity will generally diminish with distance. Additionally, two or more copies of a POMC enhancer sequence can be operably linked one after the other to produce an even greater increase in promoter activity.

Generally, an expression vector includes a nucleic acid sequence encoding a polypeptide of interest. A polypeptide of interest can be a polypeptide that affects a function of the transfected cell. Polypeptides of interest include, but are not limited to, polypeptides that confer antibiotic resistance, receptors, oncogenes, and neurotransmitters. A polypeptide of interest can also be a marker polypeptide, which is used to identify a cell of interest. Marker polypeptides include fluorescent polypeptides, enzymes, or antigens that can be identified using conventional molecular biology procedures. For example, the polypeptide can be a fluorescent marker (e.g., green fluorescent protein, *Aequoria Victoria*, or *Discosoma* DSRed), an antigenic markers (e.g., human growth hormone, human insulin, human HLA antigens), a cell surface marker (e.g., CD4, or a any cell surface receptor), or an enzymatic marker (e.g., lacZ, alkaline phosphatase). Techniques for identifying these markers in host cells include immunohistochemistry and fluorescent microscopy, and are well known in the art.

RNA molecules transcribed from an expression vector need not always be translated into a polypeptide to express a functional activity. Specific non-limiting examples of other molecules of interest include antisense RNA molecules complementary to an RNA of interest, ribozymes, small inhibitory RNAs, and naturally occurring or modified tRNAs.

Expression vectors including a POMC enhancer can be used to transform host cells. Hosts can include isolated microbial, yeast, insect and mammalian cells, as well as cells located in the organism. Biologically functional viral and plasmid DNA vectors capable of expression and replication in a host are known in the art, and can be used to transfect any cell of interest. Where the cell is a mammalian cell, the genetic change is generally achieved by introduction of the DNA into the genome of the cell (i.e., stable) or as an episome.

A "transfected cell" is a cell into which (or into an ancestor of which) has been introduced, by means of recombinant DNA techniques, a DNA molecule including a POMC enhancer element. Transfection of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences including the POMC enhancer, and a second foreign DNA molecule encoding a selectable phenotype, such as neomycin resistance. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). Other specific, non-limiting examples of viral vectors include adenoviral vectors, lentiviral vectors, retroviral vectors, and pseudorabies vectors.

The POMC enhancer elements disclosed herein can also be used in the production of transgenic animals such as transgenic mice, as described below.

Transgenic Animals

In one embodiment, in order to direct expression of a marker into POMC neurons, a non-human animal is generated that carries a transgene comprising a nucleic acid encoding a polypeptide operably linked to a POMC nucleic acid sequence, including a POMC enhancer element. In one specific, non-limiting example, expression of the marker distinguishes the POMC neurons from all other cells within the arcuate nucleus.

The POMC enhancer elements disclosed herein can be used to direct expression of a marker in POMC neurons in the arcuate nucleus of the non-human animal. The POMC enhancer element is operably linked to a promoter. Specific promoters of use include, but are not limited to, a tissue specific promoter such as the POMC promoter. Specific promoters of use also include a constitutive promoter, such as, but not limited to the thymidine kinase promoter or the human ββ-globin minimal, or an actin promoter, amongst others.

The promoter is operably linked to a nucleic acid encoding a marker, such as a polypeptide. The marker can be, but is not limited to, any polypeptide of interest. Markers include, but are not limited to, fluorescent markers (e.g., green fluorescent protein, *Aequoria Victoria*, or *Discosoma* DSRed), antigenic markers (e.g., human growth hormone, human insulin, human HLA antigens), cell surface markers (e.g., CD4, or a any cell surface receptor), or enzymatic markers (e.g., lacZ). In another non-limiting example the promoter is operably linked to induce expression of a marker that is a functionally active RNA molecule (e.g. antisense RNA molecules, ribozymes, small inhibitory RNAs, and naturally occurring or modified tRNAs).

The cDNA that encodes the marker can be fused in proper reading frame under the transcriptional and translational control of regulatory sequence of interest, such as a promoter and a POMC enhancer sequence that directs expression of the marker in the POMC neurons of the arcuate nucleus of the hypothalamus and the nucleus of the tractus solitarius. The sequences include, but are not limited to, an nPOMC1, nPOMC2, and/or nPOMC3 element(s), as disclosed herein, that direct expression of the marker in the POMC neurons of the arcuate nucleus. Specific, non-limiting examples of POMC sequences of use include, but are not limited to, murine, human, bovine, hamster, and rabbit POMC sequences. Variants of these POMC sequences, such as, but not limited to deletions, insertions, and additions are also of use, provided that these variants are conserved enhancer substitutions that direct expression of the polypeptide of interest in POMC neurons of interest (see above). In one embodiment, the POMC sequences can include the nPOMC1, nPOMC2 sequences, and/or the POMC promoter (see the Examples section below), provided that the sequences are included in a recombinant vector. In the chromosomal location of the endogenous POMC gene, intervening sequences are found between the POMC enhancer and the POMC promoter. For example, in the mouse, the POMC enhancer elements are located between approximately −13 kb and −6.5 kb upstream of the initiation site, while the POMC promoter is located in the region of −4.7 to 0 upstream of the initiation site. Thus, intervening sequences are located between position −6.5 to −0.7 upstream of the initiation site. Thus, in one embodiment, an POMC enhancer element is operably linked to a POMC promoter, and at least a portion of the intervening sequences are not included in the construct. Thus, for some sequences (e.g. mouse), at least a portion, such as about 1 kb, about 2 kb, about 3 kb, about 4 kb, about 5 kb, or about 6 kb of intervening sequences are not included in the transgene.

This construct can be introduced into a vector to produce a product that is then amplified, for example, by preparation in a bacterial vector, according to conventional methods (see, for example, Sambrook et al., *Molecular Cloning: a Laboratory Manual*, Cold Spring Harbor Press, 1989). The amplified construct is thereafter excised from the vector and purified for use in producing transgenic animals.

Any animal can be of use in the methods disclosed herein, provided the animal is any non-human animal. A "non-human animal" includes, but is not limited to, a non-human primate, a farm animal such as swine, cattle, and poultry, a sport animal or pet such as dogs, cats, horses, hamsters, rodents, or a zoo animal such as lions, tigers, or bears. In one specific, non-limiting example, the non-human animal is a transgenic animal, such as, but not limited to, a transgenic mouse, cow, sheep, or goat. In one specific, non-limiting example, the transgenic animal is a mouse.

A transgenic animal contains cells that bear genetic information received, directly or indirectly, by deliberate genetic manipulation at the subcellular level, such as by microinjection or infection with recombinant virus, such that a recombinant DNA is included in the cells of the animal. This molecule can be integrated within the animal's chromosomes, or can be included as an extrachromosomally replicating DNA sequences, such as might be engineered into yeast artificial chromosomes. A transgenic animal can be a "germ cell line" transgenic animal, such that the genetic information has been taken up and incorporated into a germ line cell, therefore conferring the ability to transfer the information to offspring. If such offspring in fact possess some or all of that information, then they, too, are transgenic animals.

Transgenic animals can readily be produced by one of skill in the art. For example, transgenic animals can be produced by introducing into single cell embryos DNA encoding a marker, in a manner such that the polynucleotides are stably integrated into the DNA of germ line cells of the mature animal and inherited in normal Mendelian fashion. Advances in technologies for embryo micromanipulation permit introduction of heterologous DNA into fertilized mammalian ova. For instance, totipotent or pluripotent stem cells can be transformed by microinjection, calcium phosphate mediated precipitation, liposome fusion, retroviral infection or other means, the transformed cells are then introduced into the embryo, and the embryo then develops into a transgenic animal. In one non-limiting method, developing embryos are infected with a retrovirus containing the desired DNA, and transgenic animals produced from the infected embryo.

In another, specific, non-limiting example, the appropriate DNA(s) are injected into the pronucleus or cytoplasm of embryos, preferably at the single cell stage, and the embryos allowed to develop into mature transgenic animals. These techniques are well known. For instance, reviews of standard laboratory procedures for microinjection of heterologous DNAs into mammalian (mouse, pig, rabbit, sheep, goat, cow)

fertilized ova include: Hogan et al., *Manipulating the Mouse Embryo*, Cold Spring Harbor Press, 1986; Krimpenfort et al., *Bio/Technology* 9:86, 1991; Palmiter et al., *Cell* 41:343, 1985; Kraemer et al., *Genetic Manipulation of the Early Mammalian Embryo*, Cold Spring Harbor Laboratory Press, 1985; Hammer et al., *Nature* 315:680, 1985; Purcel et al., *Science* 244:1281, 1986; Wagner et al., U.S. Pat. No. 5,175, 385; Krimpenfort et al., U.S. Pat. No. 5,175,384.

The disclosure of the neural-specific regulatory elements of the POMC gene is disclosed herein. This discovery was based on a combination of two approaches used in a sequential and iterative process (see the examples section below). A functional screen of reporter gene expression in transgenic mice was used to identify the broad regions of the POMC gene necessary for neural expression. A computational comparative genomics approach was also applied to narrow the search for highly conserved DNA sequences across species. The POMC sequences can be used for (1) development of transgenic animal models with heterologous protein expression targeted specifically to POMC neurons; (2) development of genetic screening for human POMC alleles which carry polymorphisms in the neural regulatory elements and affect the level of POMC gene expression and POMC neuropeptides in the central nervous system; (3) development of novel therapeutics based on small molecules that modulate POMC gene expression in the brain by interaction with the neural-specific DNA elements; and (4) identification of novel transcription factors and intracellular signaling pathways and molecules in POMC neurons that control the expression of the POMC gene or otherwise control the production, processing, or release of the biologically active neuropeptide products from the neuronal terminals.

As disclosed herein, expression of a marker in a POMC neuron allows specific identification of these neurons in a histological section. As such, sections from a non-human animal expressing a marker in proopiomelanocortin (POMC) neuron can be used to identify agents affecting either POMC neurons directly or indirectly (e.g. agents acting on NPY neurons that make synaptic contact with nearby POMC neurons) as the ability to identify the POMC neurons allow the measurement of specific neurophysiological parameters of these cells. The ability to identify and measure electrophysiological parameters of the POMC neurons enables screening for agents that affect these cells, such as agents that affect caloric intake, food intake, or appetite. In addition, the ability of agents to alter the electrophysiological parameters of the POMC neurons provides an assay to screen for agents that affect the control of body temperature, blood pressure, stress-induced analgesia, reproductive function, cognitive abilities, emotional states, rewarding behavior, responses to drugs of abuse, including opioids and ethanol, and neuroimmunomodulation

Methods for Screening

Methods for screening for an agent that affects caloric intake, food intake, appetite, and/or energy expenditure are disclosed herein. Methods are also disclosed to screen for an agent that affects body temperature, blood pressure, stress-induced analgesia, reproductive function, cognitive abilities, emotional states, rewarding behavior, responses to drugs of abuse, including opioids and ethanol, and neuroimmunomodulation. The methods include contacting a histological section of an arcuate nucleus from a non-human animal expressing a marker in proopiomelanocortin (POMC) neurons with the agent to be tested. The expression of the marker distinguishes the proopiomelanocortin neurons from the other neurons (and other cells) in the arcuate nucleus, such that electrophysiological measurements can be made on the POMC neurons. An electrophysiological parameter of the POMC neurons is measured. The effect of the agent on this parameter indicated if the agent has an effect on appetite, caloric intake, food intake, or energy expenditure upon administration of a therapeutically effective amount of the agent to a subject. Similarly, an effect on an electrophysiological parameter can indicate that an agent affects body temperature, blood pressure, stress-induced analgesia, reproductive function, cognitive abilities, emotional states, rewarding behavior, responses to drugs of abuse, including opioids and ethanol, and neuroimmunomodulation A histological section of the arcuate nucleus from a non-human animal expressing a marker in the POMC neurons is prepared using methods known to one of skill in the art, and the section is contacted with a test agent of interest. The marker is essential for the identification of the POMC neurons. An electrophysiological parameter of a POMC neuron is then assessed. Suitable electrophysiological parameters include, but are not limited to, hyperpolarization of the membrane potential of the POMC neuron and/or an increase in IPSCs in the POMC neuron. In one non-limiting example, an agonist is selected that causes hyperpolarization of the membrane potential of a POMC neuron, and increases IPSCs in a POMC neuron. Thus, an agent that affects appetite, caloric intake, food intake, energy expenditure, or can be selected. Similarly, and agent that affects body temperature, blood pressure, stress-induced analgesia, reproductive function, cognitive abilities, emotional states, rewarding behavior, responses to drugs of abuse, including opioids and ethanol, and neuroimmunomodulation can be selected.

One of skill in the art can readily assesses neuron firing rate, membrane voltage, depolarization, action potentials, and IPSC frequency. Exemplary methods are described in the examples section below. However, the methods disclosed herein are not limited to the devices and measurements described in the Examples section. For example, any electrophysiology amplifier can be utilized, such as, but not limited to, devices produced by Dagan Instruments, Minneapolis, Minn., or Heka Elektronik, Lambrecht/Pfalz, Germany.

In one embodiment, the membrane potential, action potential rate, and/or the frequency of IPSCs in a POMC neuron treated with an agent is compared to a control. Suitable controls include, but are not limited to, a section contacted with a buffer alone, in the absence of an agent, a sample contact with a control agent, such as an agent known to have an effect on the frequency of IPSCs, action potential rate, or to alter membrane potential of a POMC neuron, or an agent known not to have an effect on IPSCs, action potential rate, or membrane potential of a POMC neuron.

In one specific, non-limiting example, a section of the arcuate nucleus is contacted with an agent, and the effect on the membrane potential of a POMC neuron is measured. In this example, a change in the membrane potential of about 2 to about 50 mV indicates that the agent affects the activity of POMC neurons and therefore affects food intake, caloric intake, appetite, and/or energy expenditure when administered to a subject. In another specific, non-limiting example, a change in IPSC frequency is measured. In this example, a change in the IPSC frequency is measured. In this example, a change of the IPSC frequency from about 2% to a ten fold increase, or completely stopping IPSCs indicates that the agent affects food intake, caloric intake, appetite, and/or energy expenditure. In another embodiment, a change in the action potential rate of a POMC neuron is measured. In this example, a change in the action potential rate of about 2% to completely stopping, or a change in the action potential rate of greater than, or equal to, about a 20-fold, 50-fold or 100-fold increase indicates that the agent affects food intake, caloric intake, appetite, and/or energy expenditure. Alternatively, a change from no firing to activity of a POMC neuron indicates that the agent affects food intake, caloric intake, appetite, and/or energy expenditure. Other approaches to measuring activity include, but not be limited to, an analysis of the expression of c-fos.

One of skill in the art can readily identify a statistically analysis of use in assessing data obtained from the methods disclosed herein. The statistical analyses are standard, such as tests for repeatability, for example analysis of variance, or wilcoxin signed rank test, are performed, using an appropriate confidence level, such as, but not limited to, $p<0.05$.

It should be noted that parameters of a POMC neuron, such as, but not limited to, ion fluxes (e.g., a potassium flux), enzyme activation (e.g., a serine/threonine kinase), changes in cyclic nucleotides (e.g., cAMP, cADP, cGMP, cGDP, etc.), among others, can also be measured. A specific, non-limiting example of a signaling event is the generation of a $K^+$ flux following the interaction of an agent with a POMC neuron. A "physiological indicator," which is any compound in which a measurable property changes in a response to a physical parameter of the cell, can be used to measure the signaling event. One specific, non-limiting example of a measurable property is a change is in fluorescence of a physiological indicator in response to an ion flux.

Fluorescence is one spectral property that can be used as the means of detecting a physiological parameter of a cell. A "fluorescent property" refers to the molar extinction coefficient at an appropriate excitation wavelength, the fluorescence quantum efficiency, the shape of the excitation spectrum or emission spectrum, the excitation wavelength maximum and emission wavelength maximum, the ratio of excitation amplitudes at two different wavelengths, the ratio of emission amplitudes at two different wavelengths, the excited state lifetime, or the fluorescence anisotropy. A measurable difference in any one of these properties between a cell contacted with an agent as compared to a control cell suffices to identify a compound as being of interest. A measurable difference can be determined by determining the amount of any quantitative fluorescent property, e.g., the amount of fluorescence at a particular wavelength, or the integral of fluorescence over the emission spectrum. Optimally, the physiological indicator is selected to have fluorescent properties that are easily distinguishable. A specific, non-limiting example of a fluorescent indicator of use is fura-2. This dye measures intracellular calcium. Increased intracellular calcium is an indicator of increased neuronal activity, while decreased intracellular calcium is an indicator of decreased neural activity.

Any agent can be screened using the methods disclosed herein to determine if it affects body temperature, blood pressure, stress-induced analgesia, reproductive function, cognitive abilities, emotional states, rewarding behavior, responses to drugs of abuse, including opioids and ethanol, and neuroimmunomodulation.

In addition, an agent can be screened to determine if it affects appetite, food intake, caloric intake, and/or energy metabolism. Suitable test agents include, but are not limited to, agents that bind, or are suspected of binding a receptor on either a POMC neuron, or a NPY neuron. Receptors on a POMC neuron include, but are not limited to a melanocortin receptor, a μ-opioid receptor, a leptin receptor, and an insulin receptor. Receptors on a NPY neuron include, but are not limited to, a Y2 receptor, a leptin receptor, an insulin receptor, a melanocortin receptor, or an opiod receptor. In one specific, non-limiting example the agent is a receptor agonist, or is suspected of being a receptor agonist. In another specific, non-limiting example, the agent is a Y2 receptor agonist, or is suspected of being a Y2 receptor agonist.

Agents that can be tested using the methods disclosed herein include polypeptides, chemical compounds; biological agents such as, but not limited to polypeptides, cytokines, and small molecules, peptidomimetics; antibodies; and synthetic ligands, amongst others. Receptor agonists and antagonists can be screened.

"Incubating" includes conditions that allow contact between the test compound and the histological section. "Contacting" includes in solution and solid phase. The test compound may also be a combinatorial library for screening a plurality of compounds. Compounds that are polypeptides that are identified in the method of the invention can be further evaluated, detected, cloned, sequenced, and the like, either in solution of after binding to a solid support, by any method usually applied to the detection of a specific DNA sequence, such as PCR, oligomer restriction (Saiki et al., *Bio/Technology* 3:1008-1012, 1985), allele-specific oligonucleotide (ASO) probe analysis (Conner et al., *Proc. Natl. Acad. Sci. U.S.A.* 80:278, 1983), oligonucleotide ligation assays (OLAs) (Landegren et al., *Science* 241:1077, 1988), and the like. Molecular techniques for DNA analysis have been reviewed (Landegren et al., *Science* 242:229-237, 1988).

In one specific, non-limiting example, the agent is an antagonist for a receptor on an NPY neuron, or a POMC neuron. Thus, the agent can be, but is not limited to, an antagonist of a Y2 receptor. An electrophysiological property of the POMC neurons is measured. Increased activity of NPY neurons, measured as increased frequency of IPSCs in POMC neurons, hyperpolarization of POMC neurons, and/or a decrease in the action potential firing rate of POMC neurons indicates the antagonist is of use in increasing feeding behavior. Without being bound by theory, antagonists, such as Y2 antagonists, can stimulate NPY neurons by reducing the tonic inhibition of those neurons mediated by the Y2 R and as such will be of use in treating anorexia and cachexia. Thus, the methods described herein can be use to screen for agents that increase appetite, food intake, caloric intake and decrease energy expenditure.

In another specific, non-limiting example the agent is an agonist for a leptin receptor on a POMC neuron or an NPY neuron that makes synaptic contact with a POMC neuron. An electrophysiological property of the POMC neuron is measured. Increased activity of POMC neurons, measured as decreased frequency of IPSCs in POMC neurons, depolarization of POMC neurons, and/or an increase in the action potential firing rate of POMC neurons indicates the agonist is of use in decreasing feeding behavior.

The binding affinities of receptor agonists (or antagonists) can also be determined in either cells or a membrane preparation expressing the receptor. For example, assays are utilized in which a labeled ligand is employed. A number of labels have been indicated previously (e.g., radiolabels, fluorescence labels, among others) to be of use. The candidate compound is added in an appropriate buffered medium. After an incubation to ensure that binding has occurred, the surface may be washed free of any nonspecifically bound components of the assay medium, particularly any nonspecifically bound labeled ligand, and any label bound to the surface determined. The label may be quantitatively measured. By using standards, the relative binding affinity of a candidate compound can be determined.

Following screening using the methods disclosed herein, further testing can be performed, either in animal models or in clinical trials, to confirm that the agent affects food intake, caloric intake, appetite, or energy expenditure. Similarly further testing can be done to confirm that the agent affects body temperature, blood pressure, stress-induced analgesia, reproductive function, cognitive abilities, emotional states, rewarding behavior, responses to drugs of abuse, including opioids and ethanol, and neuroimmunomodulation. Exemplary in vivo assays for food intake, caloric intake, appetite, or energy expenditure are described in the Examples section below. However, one of skill in the art can readily design alternative in vivo assays or clinical trials.

A PYY agonist or antagonist can be screened using the methods disclosed herein, in order to determine if the PYY agonist will affect caloric intake, food intake, appetite, and/or energy metabolism. A PYY agonist is a molecule that binds to a receptor that specifically binds PYY, and elicits an effect of PYY. Suitable PYY agonists and antagonists that can be screened using the methods disclosed herein include compounds that bind specifically in a Y receptor assay or competes for binding with PYY, such as in a competitive binding assay with labeled PYY. Suitable PYY agonists include, but are not limited to, compounds that bind to the Y2 receptor.

Thus, in one embodiment, a PYY agonist is selected using the methods disclosed herein that binds to a NPY neuron in the arcuate nucleus, and results in an electrophysiological effect on an NPY neuron. The electrophysiological effect on the NPY neuron can result in a further electrophysiological effect on a POMC neuron. Thus, one specific, non-limiting example, a PYY agonist is selected, using the methods disclosed herein, that causes depolarization of the membrane potential of a POMC neuron. In another specific, non-limiting example, a PYY agonist is selected using the method disclosed herein that causes an decrease in IPSCs in a POMC neuron, and/or an increased activity of a POMC neuron. In several non-limiting examples, agonists that cause hyperpolarization of the membrane potential of a POMC neuron, increase in IPSCs in a POMC neuron, are selected using the methods disclosed herein.

PYY and agonists that can be screened using the methods disclosed herein include, but are not limited to, polypeptides comprising, or alternatively consisting of, the amino acid sequence for PPY and agonists thereof, e.g., mutants, fragments and/or variants thereof. Variants include deletions, insertions, inversions, repeats and substitutions (e.g., conservative substitutions and non-conservative substitutions). More than one amino acid (e.g., 2, 3, 4, 5, 6, 7, 8, 9, 10, etc.) can be deleted or inserted or substituted with another amino acid. Typically conservative substitutions are the replacements, one for another, among the aliphatic amino acids Ala, Val, Leu and Ile; interchange of Ser and Thr containing hydroxy residues, interchange of the acidic residues Asp and Glu, interchange between the amide residues Asn and Gln, interchange of the basic residues Lys and Arg, interchange of the aromatic residues Phe and Tyr, and interchange of the small-sized amino acids Ala, Ser, Thr, Met and Gly.

As another example, polypeptide fragments may contain a continuous series of deleted residues from the amino (N)- or the carboxyl (C)-terminus, or both. Any number of amino acids, ranging from 1 to 24, can be deleted from the N-terminus, the C-terminus or both.

Furthermore, the agonist polypeptides that are screened using the methods disclosed herein, also include, but are not limited to, polypeptides comprising, or alternatively consisting of, internal deletions of the amino acid sequences for PPY and/or agonist thereof. Such deletions may comprise one or more amino acid residue deletions (e.g., one, two, three, four, five, six, seven, eight, nine, ten, etc.) and may begin at any amino acid position (e.g., two, three, four, five, six, seven, eight, nine, ten, etc.). In addition, polypeptides can be screened that contain one or more such internal deletions. Such deletions are can be made in PPY, NPY and PP.

Also contemplated is the screening of agonist peptides that are PPY, NPY and/or PP chimeras having high affinity and/or selectivity for the Y2 receptor. These chimeras may comprise amino acid substitutions of one or more amino acids (e.g., 1, 2, 3, 4, 5, 6, 7, 8, 9, 10, etc.) from PPY, NPY and/or PP, variants, mutants and/or deletions thereof, with one or more amino acids (e.g., 1, 2, 3, 4, 5, 6, 7, 8, 9, 10, etc.) from a second PPY, NPY, or PP, variants, mutations and/or deletions thereof. These substitutions may begin at any amino acid position (e.g., two, three, four, five, six, seven, eight, nine, ten, etc.).

In one embodiment, the agents that are screened using the methods disclosed herein are selective for the Y2 receptor. That is, they bind with higher affinity to Y2 compared to other receptors, such as Y1, Y2, Y3, Y4, Y5 and Y6. In another embodiment, the peptides are selective for the Y2 and Y5 receptors over the Y1, Y3, Y4 and Y6 receptors.

Other polypeptide fragments that can be screened are fragments comprising structural or functional domain of the polypeptides of this disclosure. Such fragments include amino acid residues that comprise a polyproline-type II helix (residues 1-8), beta-turn (residues 9-14), amphipathic alpha-helix (residues 15-32) and/or a C-terminal turn structure (residues 33-36). See, Kirby et al., *J Med Chem* 36:385-393, 1993.

In addition, this disclosure includes the screening of a polypeptide or agonist comprising, or alternatively consisting of, the amino acid sequence for PPY, NPY and PP species variants and/or mutants, and fragments thereof. Also contemplated is the screening of fusion proteins, whereby a PYY or PYY agonist will be fused to another protein or polypeptide (the fusion partner) using recombinant methods known in the art, to identify fusion proteins of use in reducing appetite, caloric intake, food intake, and/or energy expenditure. These fusion proteins can be synthetically synthesized by any known method. Any known peptide or protein can be used as the fusion partner (e.g., serum albumin, carbonic anhydrase, glutathione-S-transferase or thioredoxin, etc.).

The disclosure is illustrated by the following non-limiting Examples:

EXAMPLES

Example 1

Material and Methods

Generation of POMC-EGFP mice: The EGFP cassette contains its own Kozak consensus translation initiation site along with SV40 polyadenylation signals downstream of the EGFP coding sequences directing proper processing of the 3' end of the EGFP mRNA. The EGFP cassette was introduced by standard techniques into the 5' untranslated region of exon 2 of a mouse Pomc genomic clone containing 13 kb of 5' and 2 kb of 3' flanking sequences (Young et al., *J Neurosci* 18:6631-40, 1998). The transgene was microinjected into pronuclei of one-cell stage embryos of C57BL/6J mice (Jackson Laboratories) as described (Young et al., *J Neurosci* 18:6631-40, 1998). One founder was generated and bred to wildtype C57BL/6J to produce $N_1$ hemizygous mice. In addition, $N_2$ and subsequent generations of mice homozygous for the transgene were also generated. The mice are fertile and have normal growth and development.

Immunofluorescence and GFP co-localization: Anesthetized mice were perfused transcardially with 4% paraformaldehyde and free-floating brain sections prepared with a vibratome. Sections were processed for immunofluorescence and colocalization of GFP fluorescence using standard techniques. Primary antisera and their final dilutions were rabbit anti-β-endorphin, 1:2500 v/v; rabbit anti-NPY, 1:25,000 v/v (Alanex Corp.); rabbit anti-ACTH, 1:2000 v/v; rabbit anti-GFP 1:10,000 v/v (AbCam); and mouse anti-TH, 1:1000 v/v (Incstar). After rinsing, sections were incubated with 10 mg/ml biotinylated horse anti-mouse/rabbit IgG (Vector Laboratories) followed by Cy-3 conjugated streptavidin, 1:500 v/v (Jackson Immunoresearch Laboratories). Photomicrographs were taken on a Zeiss Axioscop using FITC and RITC filter sets (Chroma Technology Corp.). Other tissue sections were developed with ABC reagent (Vector Laboratories) and either diaminobenzidine or benzidine dihydrochloride as the chromagen.

Electrophysiology (Example 2): 200 μm thick coronal slices were cut from the ARC of four-week old male POMC-EGFP mice. Slices were maintained in (in mM) [NaCl, 126; KCl, 2.5; $MgCl_2$, 1.2; $CaCl_2.2H_2O$, 2.4; $NaH_2PO_4.H_2O$, 1.2; $NaHCO_3$, 21.4; Glucose, 11.1] (Krebs) at 35° C. and saturated with 95% $O_2$ 5% $CO_2$ for 1 hour (hr) prior to recordings. Recordings were made in Krebs at 35° C. Slices were visualized on an Axioskop FS2 (Zeiss) through standard infra red optics and using epifluorescence through a FITC filter set (see FIG. 1*c*). Whole cell recordings were made from fluorescent neurons using an Axopatch 1D amplifier (Axon Instruments) and Clampex 7 (Axon Instruments). Resting membrane potentials were determined using an event detection protocol on a PowerLab system (AD Instruments, Mountain View, Calif.) to average expanded traces of the membrane potential. Drugs were applied to the bath over the times indicated. The resting membrane potential was stable for up to an hour in cells treated with Krebs alone. I-V relationships for the Met-Enk currents were established using a step protocol; (−60 mV holding potential, sequentially pulsed (40 ms) from −120 to −50 mV, cells were returned to −60 mV for 2 seconds between voltage steps). The protocol was repeated after Met Enk addition. The net current was the difference between the two I-V relationships. This protocol was repeated in Krebs with 6.5 mM $K^+$. I-V relationships to identify the postsynaptic leptin current were performed similarly with slow voltage ramps (5 mV/s from −100 to −20 mV) before and 10 minutes after the addition of leptin (100 nM). GABAergic IPSCs were recorded using a CsCl internal electrode solution (in mM) [CsCl, 140; Hepes, 10; $MgCl_2$, 5; Bapta, 1; (Mg)-ATP, 5; (Na)GTP, 0.3]. Both mini IPSCs and large amplitude (presumably multisynaptic) IPSCs were observed in the untreated slices. TTX (1 μM) abolished large IPSCs. Data were acquired before and after addition of drug for the times indicated on the figures at a −50 mV holding potential in 2 second sweeps every 4 seconds Mini postsynaptic currents were analyzed using Axograph 4 (Axon Instruments). IPSCs and excitatory postsynaptic currents (EPSCs) were distinguished on the basis of their decay constants; additionally picrotoxin (100 μM) blocked all IPSCs. POMC neurons receive a low EPSC tone and the frequency was not modulated by any of the treatments described here.

Immunostaining for light and electron microscopy: Double immunocytochemistry for NPY and POMC using different color diaminobenzidine(DAB) chromogens was carried out on fixed mouse hypothalami according to published protocols (Horvath et al., *Neuroscience* 51:391-9, 1992). For electron microscopy, preembedding immunostaining for β-endorphin was using an ABC Elite kit (Vector Laboratories) and a DAB reaction followed by post-embedding labeling of GABA and NPY using rabbit anti-GABA, 1:1000 v/v and gold conjugated (10 nm) goat anti-rabbit IgG or sheep anti-NPY and gold conjugated (25 nm) goat anti-sheep IgG. Finally, sections were contrasted with saturated uranyl acetate (10 minutes) and lead citrate (20-30 seconds) and examined using a Philips CM-10 electron microscope.

Animals: Male Pomc-EGFP mice were studied at 5-6 weeks of age and were generated as described above. Male mice aged 8-12 weeks and between 20-30 g bodyweight were kept under controlled temperature (21-23° C.) and light conditions (lights on 06:00-18:00) with ad libitum access to water and food except where stated. All studies were performed in the early light-phase (0700-0800).

Intraperitoneal injections: Mice were accustomed to IP injection by injections of 0.5 ml saline on the two days prior to study. For all studies, animals received an IP injection of either $PYY_{3-36}$ or saline in 100 μl.

Electrophysiology: Whole cell patch clamp recordings were made from POMC neurons in the hypothalamus of 180 μm thick coronal slices from Pomc-EGFP mice, as previously reported (Cowley et al., *Nature* 411:480-484, 2001). "Loose cell-attached" recordings were made using extracellular buffer in the electrode solution, and maintaining seal resistance between 3-5 Mohm throughout the recording. Firing rates were analyzed using mini-analysis protocols (Mini-Analysis, Jaejin Software, N.J.). Vehicle controls were used in this system, previously validated for the electrophysiological actions of neuropeptides (Cowley et al., *Nature* 411:480-484, 2001). Data were analyzed by ANOVA, Neuman-Keuls posthoc comparison, and Wilcoxon Signed Rank Test.

C-fos expression: C-fos expression was measured in Pomc-EGFP mice 2 hours after IP administration of saline or $PYY_{3-36}$ (5 μg/100 g) using standard immunohistochemical techniques (Hoffinan et al., *Front. Neuroendocrinol.* 14:173-213, 1993). Data were obtained from 5 mice in each group. For the Pomc-EGFP mice 5 anatomically matched arcuate nucleus sections (Franklin et al., *The Mouse Brain in Stereotaxic Coordinates* (Academic Press, San Diego, 1997) were counted from each animal, and images acquired using a Leica TSC confocal microscope (Grove et al., *Neuroscience* 100: 731-40, 2000).

Measurements of Energy Expenditure: To determine the actions of PYY on energy expenditure the OXYMAX system (Columbus Instruments, Columbus, Ohio) is utilized with rodents following PYY injection into a treatment cohort. This system is also utilized with rodents following a saline injection (control cohort). The equipment measures $O_2$ consumption and $CO_2$ production; the efficiency with which the body produces $CO_2$ from $O_2$ gives a reliable index of caloric or metabolic efficiency.

POMC sequences: A human large genomic contig (*Homo sapiens* chromosome 2 reference contig) including the complete POMC gene and the nPOMC1, nPOMC2 and nPOMC3 elements can be found in GenBank, the NIH sequence database maintained by the National Center for Biotechnology Information (NCBI). The information relating to this sequence is as follows:

Accession No.: NT_005204.

A mouse large genomic contig (*Mus musculus* chromosome 12 WGS supercontig) including the complete POMC gene and the nPOMC I, POMC2 and nPOMC3 elements) can also be found in GenBank. The information relating to this sequence is as follows:

Accession No.: NW_000041

A rat large genomic contig (*Rattus norvegicus* chromosome 6 WGS supercontig) including the complete POMC gene and the nPOMC1, POMC2 and nPOMC3 elements) can also be found in GenBank. The information relating to this sequence is as follows:

Accession NO.: NW_043940

All these GenBank entries are incorporated herein by reference in their entirety.

Example 2

Neural Network in the Arcuate Nucleus

Figure 1B:
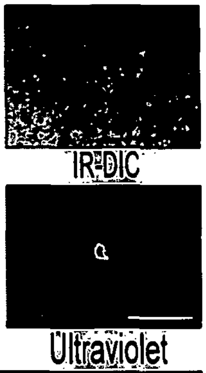
FIG. 1*b* is a digital image showing the identification of a single POMC neuron (arrowhead on recording electrode tip) by EGFP fluorescence (upper) and IR-DIC microscopy (lower) in a living ARC slice prior to electrophysiological recordings.
Figure 1C:
FIG. 1*c* is a set of digital images showing the co-localization (bright, on right) of EGFP (left) and β-endorphin immunoreactivity (middle) in ARC POMC neurons. Scale bars: b & c, 50 μm.
Figure 1D:
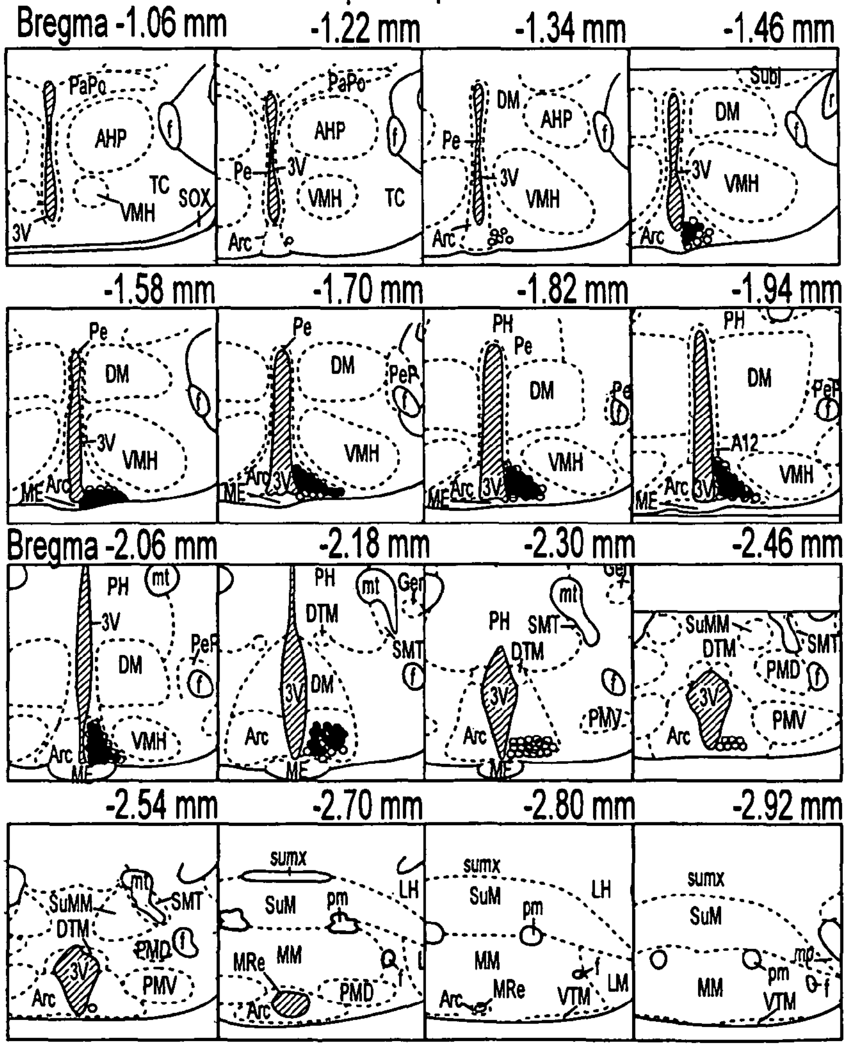
FIG. 1*d* is a set of diagrams showing the distribution of EGFP-positive neuronal soma throughout the ARC nucleus. ○=5 cells, ●=10 cells.
Figure 1E:
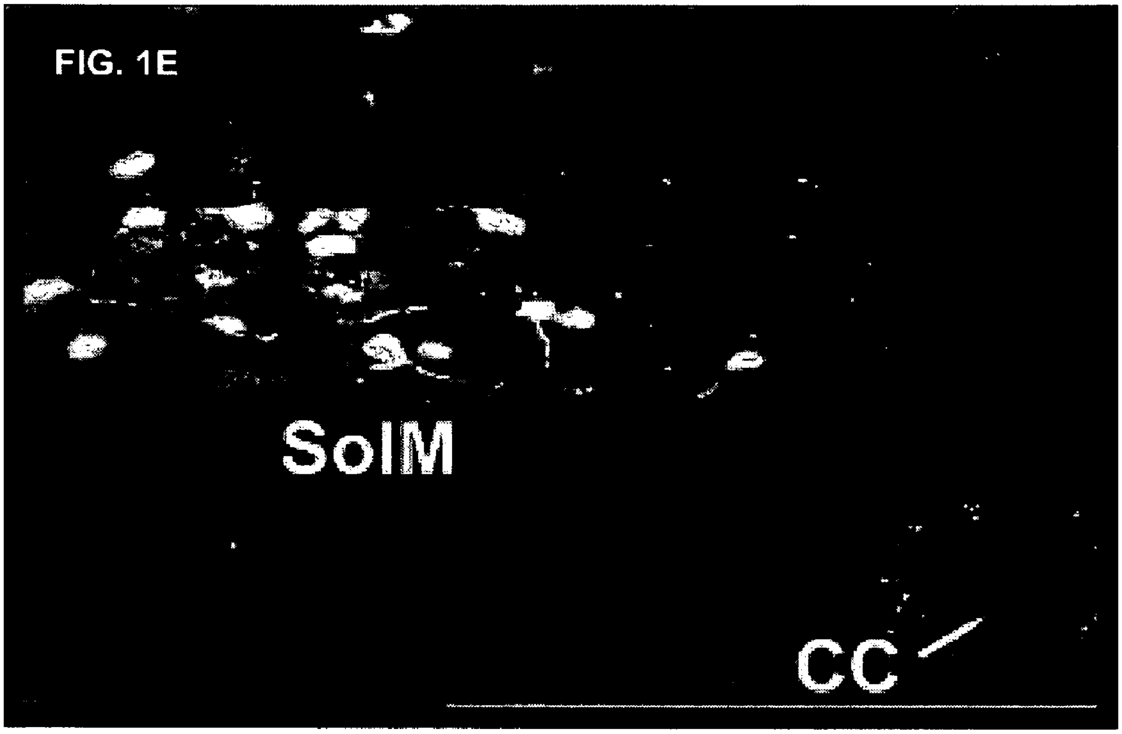
FIG. 1*e* is a digital image showing the identification of POMC neurons by EGFP fluorescence in the medial nucleus of the solitary tract (SolM) adjacent to the central canal (CC) in the medullary region of the brainstem.
Figure 1F:
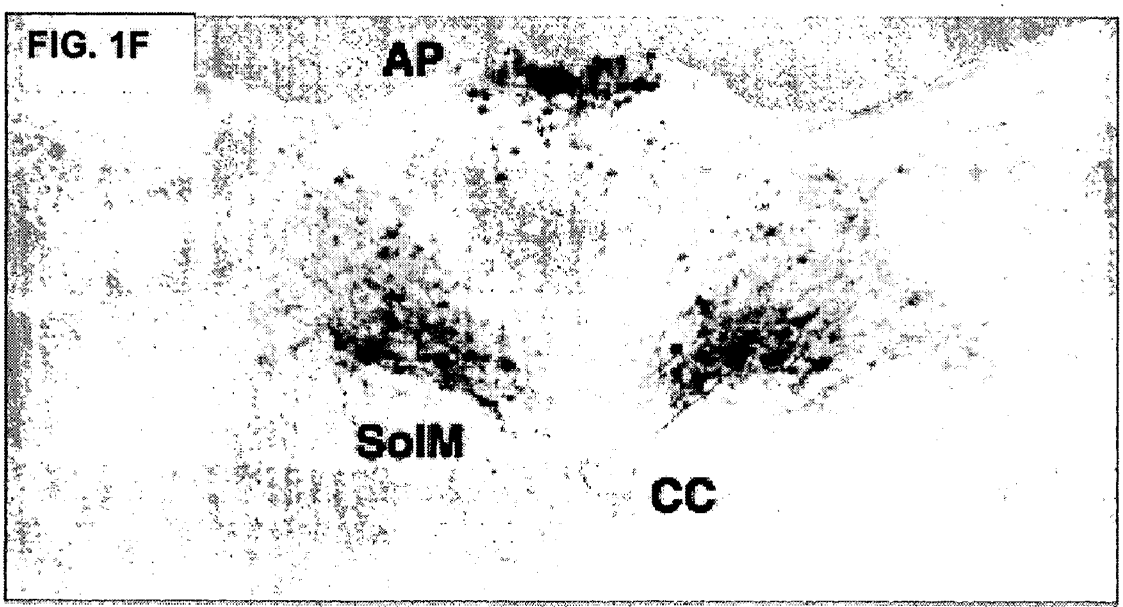
FIG. 1*f* is a lower magnification digital image showing the identification of POMC neurons by immunohistochemistry with an antisera directed against GFP in the SolM and area postrema (AP).
Figure 1G:
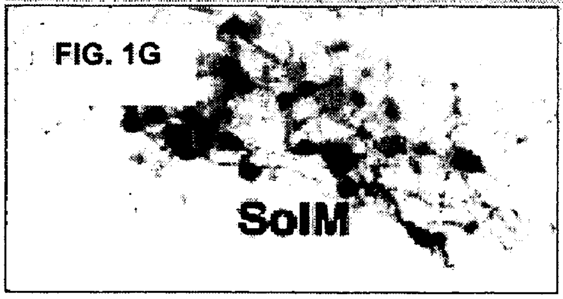
FIGS. 1*g* and 1*h* are a set of digital images showing higher magnifications of the neurons in the SolM and AP, respectively, depicted in FIG. 1*f*.
Figure 1H:
Figure 1N:
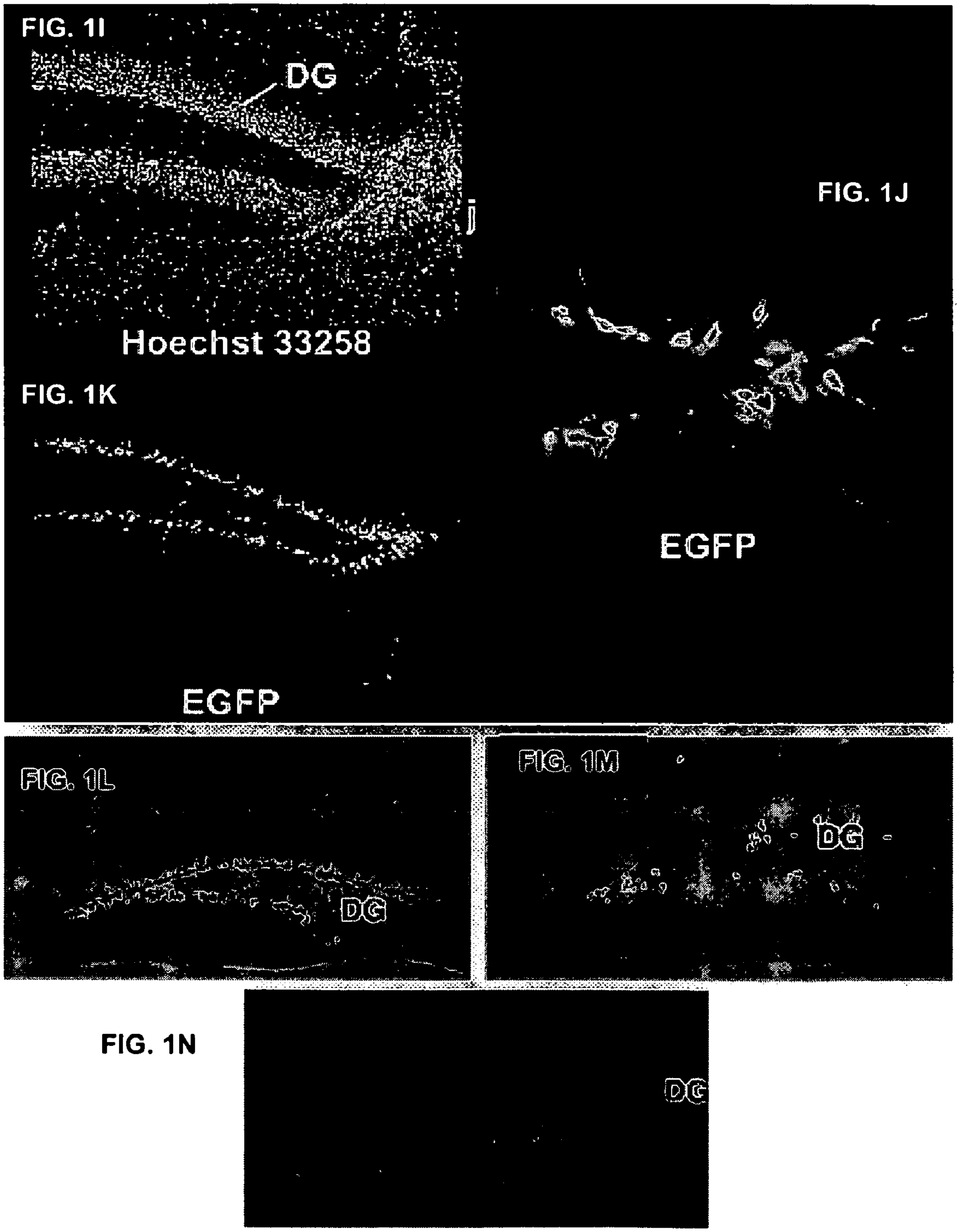
FIG. 1*n* is a digital image showing a higher magnification of the EGFP-immunopositive neurons in the DG depicted in FIG. 1*l*.

A strain of transgenic mice was generated expressing green fluorescent protein (EGFP Clontech), under the transcriptional control of mouse Pomc genomic sequences that include a region located between −13 kb and −2 kb required for accurate neuronal expression (Young et al., *J Neurosci* 18:6631-40, 1998) (FIG. 1*a*). Bright green fluorescence (509 nm) was seen in the two CNS regions where POMC is produced: the ARC and the nucleus of the solitary tract. Under ultraviolet (450-480 nm) excitation POMC neurons were clearly distinguished from adjacent, non-fluorescent neurons (FIG. 1*b*) visualized under infrared optics. Double immunofluorescence revealed >99% cellular co-localization of EGFP and POMC peptides within the ARC (FIG. 1*c*). There was close apposition of both tyrosine hydroxylase (TH)- and NPY-stained terminals on EGFP-expressing POMC neurons, but no evidence of co-localization of the TH or NPY immunoreactivity with EGFP. Total fluorescent cell counts performed on coronal hypothalamic sections revealed 3148±62 (mean±s.e.m. n=3) POMC-EGFP neurons distributed through the entire ARC (Franklin et al., *The Mouse Brain in Stereotaxic Coordinates* (Academic Press, San Diego, Calif., 1997) (FIG. 1*d*). POMC neurons in the mouse are located both medially and ventrally within the ARC, in contrast to a predominantly lateral position in the rat ARC. FIG. 1*e* shows fluorescently labeled neurons in the nucleus of the tractus solitarius. FIGS. 1*f-h* show immunohistochemically labeled neurons in the nucleus of the solitary tract and area postrema. FIGS. 1*i-k* show fluorescently labeled neurons in the granular cell layer of the dentate gyrus of the hippocampus. FIGS. 1*l-m* show immunohistochemically labeled neurons in the granular cell layer of the dentate gyrus of a young (two-month old) and an old (18-month old) POMC-EGFP mouse.

Figures 2A, 2B, 2C:
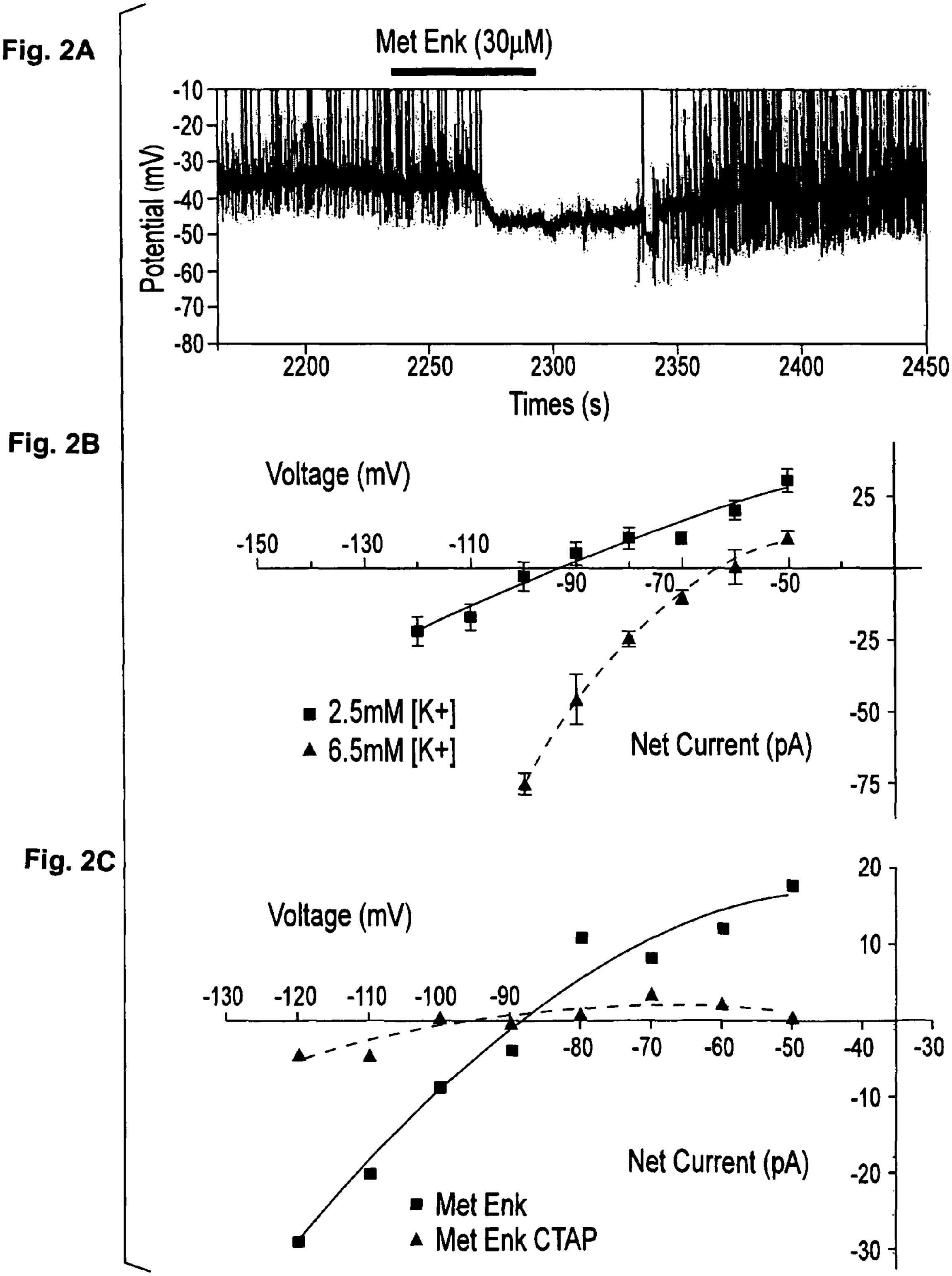
FIG. 2*a* is a tracing showing met-enkephalin hyperpolarizes POMC neurons and inhibits all action potentials. The horizontal bar indicates the time when 30 μM Met-Enk was bath-applied to the slice.
FIG. 2*b* is a graph showing met-enkephalin current and reversal potential is shifted by extracellular $K^+$ concentration.
FIG. 2*c* is a graph showing met-enkephalin activates MOP-Rs on POMC neurons. A Met-Enk (30 μM) current was observed and the MOP-R specific antagonist CTAP (1 μM) was applied for 1 minute. Following CTAP Met-Enk elicited no current. The figure is representative of three experiments.

POMC-EGFP neurons in hypothalamic slices had a resting membrane potential of −40 to −45 mV and exhibited frequent spontaneous action potentials. The non-selective opioid agonist met-enkephalin (Met-Enk: 30 μM; Sigma) caused a rapid (35-40 s), reversible hyperpolarization (10-20 mV) of the membrane potential of POMC cells (n=10) and prevented spontaneous action potential generation (FIG. 2*a*). In normal (2.5 mM $K^+$) Krebs buffer, the reversal-potential of the inwardly-rectifying opioid current was approximately −90 mV, while in 6.5 mM $K^+$ Krebs the reversal-potential was shifted to approximately −60 mV (n=3: FIG. 2*b*). The μ opioid receptor (MOP-R) antagonist CTAP (1 μM; Phoenix Pharmaceuticals) completely prevented the current induced by Met-Enk in POMC cells (n=3: FIG. 2*c*). These characteristics indicate the opioid current was due to activation of MOP-R and increased ion conductance through G protein coupled, inwardly-rectifying potassium channels (GIRK) (Kelly et al., *Neuroendocrinology* 52:268-75, 1990). The similar opioid responses in EGFP-labeled POMC neurons to that of guinea pig (Kelly et al., *Neuroendocrinology* 52:268-75, 1990) or mouse (Slugg et al., *Neuroendocrinology* 72:208-17, 2000). POMC cells, identified by post-recording immunohistochemistry, suggests that expression of the EGFP transgene does not compromise either expression of receptors nor their coupling to second messenger systems in POMC neurons.

Figures 3A, 3B, 3C, 3D, 3E, 3F:
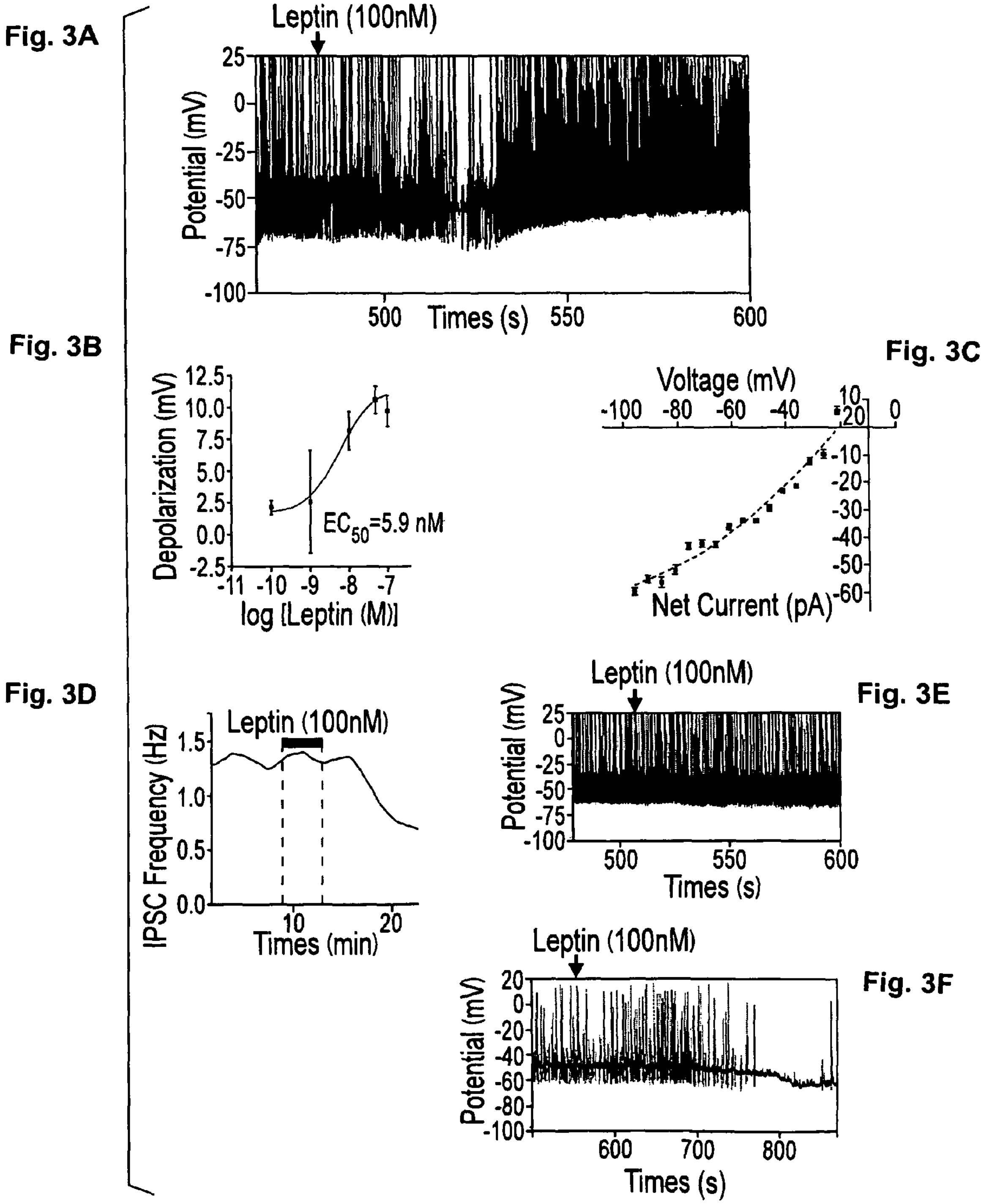
FIG. 3*a* is a tracing demonstrating that leptin depolarizes POMC neurons and increases the frequency of action potentials within 1 to 10 minutes of addition. The figure is a representative example of recordings made from 77 POMC neurons.
FIG. 3*b* is a graph showing that leptin causes a concentration dependent depolarization of POMC cells. The depolarization caused by leptin was determined at 0.1, 1, 10, 50, and 100 nM ($EC_{50}$=5.9 nM) in (8, 7, 9, 3, 45) cells respectively.
FIG. 3*c* is a graph showing that leptin depolarizes POMC cells by activating a nonspecific cation current. The figure is representative of the response in 10 cells.
FIG. 3*d* is a graph showing that leptin decreases the frequency of IPSCs in POMC cells. The figure is an example of 5 cells in which leptin (100 nM) decreased the frequency of IPSCs.
FIG. 3*e* is a tracing demonstrating that leptin had no effect on 5 adjacent non-fluorescent ARC neurons.
FIG. 3*f* is a tracing showing that leptin hyperpolarized 5 non-fluorescent ARC neurons.

Next, the direct effects of leptin on identified POMC cells in slice preparations were investigated. Leptin (0.1-100 nM) depolarized 72 of 77 POMC cells by 3-30 mV (FIG. 3*a*; mean±s.e.m. depolarization at 100 nM leptin=9.7±1.2 mV, n=45) within 2-10 minutes, in a concentration responsive manner (FIG. 3*b*). There were two components to the depolarization and neither were fully reversible within 40 minutes. Firstly, the depolarization was due to a small inward current which reversed at approximately −20 mV (FIG. 3*c*), suggesting the involvement of a non-specific cation channel (Powis et al., *Am J Physiol* 274, R1468-72, 1998). Secondly, leptin treatment decreased the GABAergic tone onto POMC cells. GABAergic inhibitory postsynaptic currents (IPSCs) were observed in POMC cells and leptin (100 nM) decreased their frequency by 25% (FIG. 3*d*) in 5 out of 15 cells suggesting that it acted presynaptically to reduce GABA release (leptin had no effect on IPSCs in 10 out of 15 POMC neurons). The effect on IPSC frequency occurred with a similar lag to the effect on membrane potential. Thus, leptin not only directly depolarizes POMC neurons but also acts at GABAergic nerve terminals to reduce the release of GABA onto POMC neurons, allowing them to adopt a more depolarized resting potential. The consistent depolarization of POMC cells by leptin was specific because leptin had no effect on 5 of 13 adjacent non-fluorescent cells tested (FIG. 3*e*), while it hyperpolarized 5 (FIG. 3*f*) and depolarized 3 other non-POMC neurons in the ARC. The electrophysiological effects of leptin reported here are consistent with leptin's biological actions; leptin rapidly causes release of α-MSH from rat hypothalami (Kim et al., *J Clin Invest* 105:1005-11, 2000), presumably by activating POMC neurons.

Figures 4A, 4B, 4C, 4D, 4E, 4F:
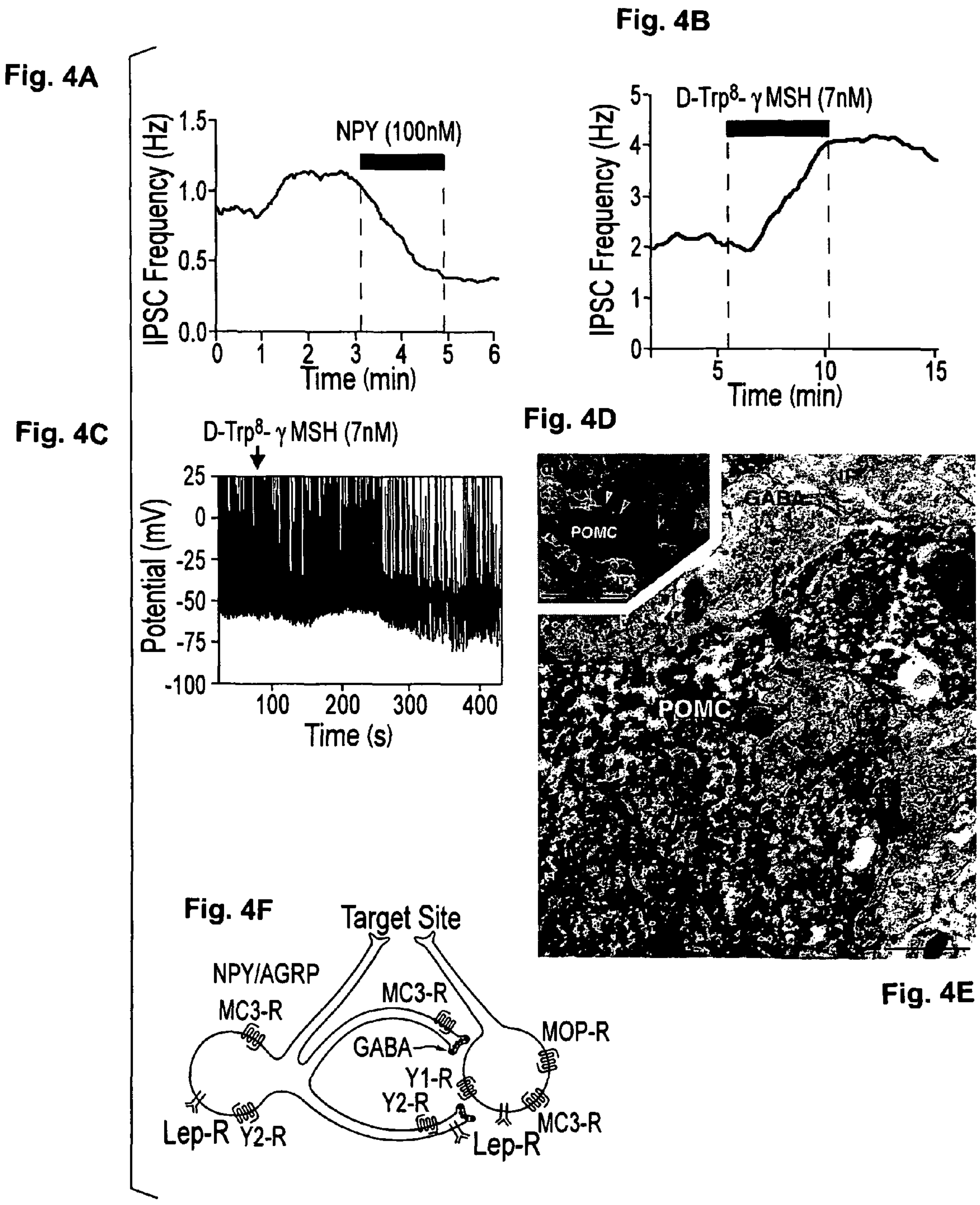
FIG. 4*a* is a graph showing that NPY decreases the frequency of mini IPSCs in POMC neurons.
FIG. 4*b* is a graph demonstrating that D-$Trp^8$-γMSH (7 nM), a dose that selectively activates MC3-R, increases the frequency of GABAergic IPSCs in POMC neurons.
FIG. 4*c* is a tracing showing that D-$Trp^8$-γMSH hyperpolarizes POMC neurons.
FIG. 4*d* is a set of digital images demonstrating that expression of NPY in nerve terminals adjacent to POMC neurons in the ARC. NPY nerve terminals (black, arrowheads); POMC neuronal soma (grey). Scale bar, 10 μm.
FIG. 4*e* is a digital image showing expression of GABA and NPY in nerve terminals synapsing onto POMC neurons in the ARC. GABA immunoreactivity (10 nm gold particles, arrowheads without tail) and NPY immunoreactivity (25 nm gold particles, arrows with tail) are in separate vesicle populations co-localized within synaptic boutons that make direct contact with the soma of POMC neurons (DAB contrasted with uranyl acetate and lead citrate, diffuse black in cytoplasm). Scale bar, 1 μm.
FIG. 4*f* is a diagram of the model of NPY/GABA and POMC neurons in the ARC.

Previous reports of neuronal hyperpolarization by leptin (Glaum et al., *Mol Pharmacol* 50:230-5, 1996; Spanswick et al., *Nature* 390:521-5, 1997), and the demonstrated co-localization of GABA and NPY (Horvath et al., *Brain Res* 756: 283-6, 1997) within subpopulations of ARC neurons, suggested that leptin hyperpolarizes NPY/GABA cells that directly innervate POMC neurons, and thus reduces GABAergic drive onto POMC cells. Both the leptin and NPY Y2 receptors are expressed on NPY neurons in the ARC (Hakansson et al., *J Neurosci* 18:559-72, 1998; Broberger et al., *Neuroendocrinology* 66:393-408, 1997). Furthermore, activation of Y2 receptors inhibits NPY release from NPY neurons (King et al., *J Neurochem* 73:641-6, 1999), and presumably would also diminish GABA release from NPY/GABA terminals. This provides an alternative pharmacological approach, independent of leptin, to test the hypothesized innervation of POMC neurons by GABAergic NPY neurons. Indeed, NPY (100 nM; Bachem) decreased the frequency of GABAergic IPSCs by 55% within 3 minutes, in all 12 POMC cells tested (FIG. 4*a*). Both NPY and leptin still inhibited IPSCs in the presence of tetrodotoxin (TTX) (6 of 6 and 3 of 5 cells respectively), indicating that some of the inhibition of IPSCs was occurring through direct effects at presynaptic nerve terminals. POMC neurons express the NPY Y1 receptor (Broberger et al., *Neuroendocrinology* 66:393-408, 1997) and NPY also hyperpolarized all POMC neurons tested, by an average of 9±6 mV (n=3).

Another pharmacological test to confirm the origin of GABAergic innervation on POMC neurons from NPY/GABA terminals was to test the effect of the recently characterized and highly selective MC3-R agonist D-$Trp^8$-γMSH (Grieco et al., *J Med Chem* 43:4998-5002, 2000) on local GABA release. D-$Trp^8$-γMSH (7 nM) increased the frequency of GABAergic IPSCs (280±90%) recorded from 3 of 4 POMC neurons (FIG. 4*b*). It had no effect on one cell. The positive effect of MC3-R activation, together with the negative effects of NPY and leptin, demonstrate the dynamic range of the NPY/GABA synapse onto POMC neurons and point to the important role of this synapse in modulating signal flow within the ARC. D-$Trp^8$-γMSH (7 nM) also hyperpolarized (−5.5±2.4 mV) 9 of 15 POMC neurons tested and decreased the frequency of action potentials (FIG. 4*c*); the remaining cells showed no significant response to D-Trp[8]-γMSH. These effects could be due entirely to increased GABA release onto the POMC cells, or could be due to an additional postsynaptic action of D-Trp[8]-γMSH on POMC neurons, approximately half of which also express the MC3-R (Bagnol et al., *J Neurosci* (*Online*) 19, RC26, 1999). Thus, MC3-R acts in a similar autoreceptor manner to MOP-Rs on POMC neurons, diminishing POMC neuronal activity in response to elevated POMC peptides.

To further determine that the IPSCs in POMC neurons were due to local innervation by NPY/GABA cells, multi-label immunohistochemistry was performed using light and electron microscopy. Although independent NPY (Csiffary et al., *Brain Res* 506:215-22, 1990) and GABA (Horvath et al., *Neuroscience* 51:391-9, 1992) innervation of POMC cells has been reported, co-localization of NPY and GABA in nerve terminals forming synapses onto POMC cells has not been shown. Similar to the rat (Csiffary et al., *Brain Res* 506:215-22, 1990), a dense innervation of POMC cells by NPY axon terminals was detected in the mouse (FIG. 4*d*). Electron microscopy confirmed the coexpression of NPY and GABA in axon terminals and revealed that these boutons established synapses on the perikarya of all 15 ARC POMC neurons analyzed (representative example, FIG. 4*e*).

A detailed model of regulation of this circuit shows dual mechanisms of leptin action in the ARC, interactions between NPY/GABA and POMC neurons, and autoregulatory feedback from opioid and melanocortin peptides as well as NPY (FIG. 4*f*). In this model, leptin directly depolarizes the POMC neurons and simultaneously hyperpolarizes the somata of NPY/GABA neurons, and diminishes release from NPY/GABA terminals. This diminished GABA release disinhibits the POMC neurons, and result in an activation of POMC neurons and an increased frequency of action potentials.

The ability to direct expression of a transgene to POMC neurons allows measurement of the effects of agents on the interaction of NPY and POMC neurons. The effect of PYY on feeding in rats, and mice has been established (Batterham et al., *Nature* 418:450, 2002). The effect of PYY on feeding in humans has been established (Batterham et al., *Nature* 418: 450, 2002. Thus, the ability to specifically detect POMC neurons, and to measure the effects of agents on the NPY/POMC circuit, allows identification of agents that affect caloric intake, food intake, and appetite.

Example 3

PYY Administration Affects c-fos Expression

Figures 5A, 5B, 5C, 5D:
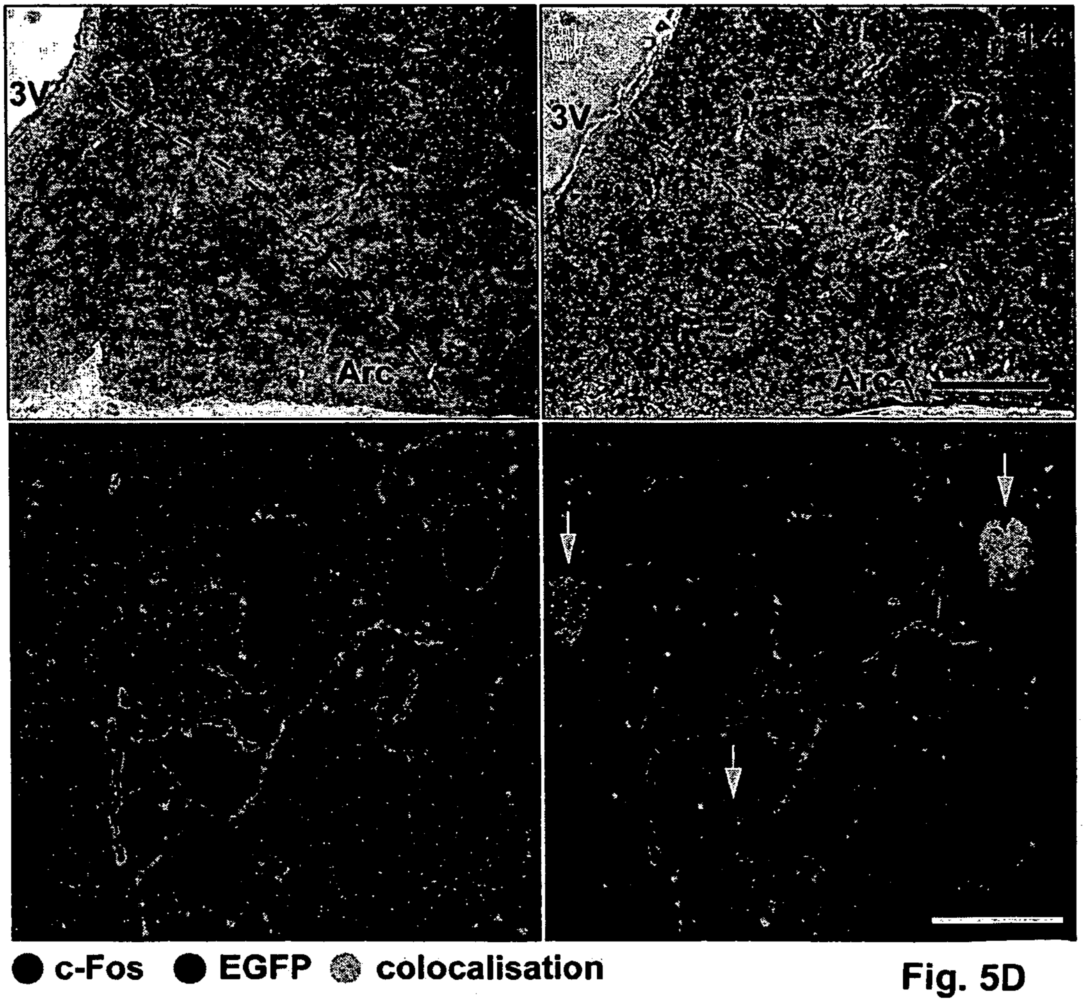
FIGS. 5*a* and 5*b* are digital images of representative sections (bregma −1.4 mm[22]) of c-fos expression in the arcuate nucleus of Pomc-EGFP mice response to intraperitoneal saline (FIG. 5*a*) or $PYY_{3-36}$ (5 μg/100 g) (FIG. 5*b*). Scale bar 100 μm. 3V, third ventricle; Arc, arcuate nucleus.
FIGS. 5*c* and 5*d* are digital images of representative sections showing POMC-EGFP neurons (FIG. 5*c*) and c-fos immunoreactivity (FIG. 5*d*) either co-localising (bright arrows) or alone (single darker arrow). Scale bar 25 μm.

To investigate whether this inhibition of food intake involved a hypothalamic pathway, c-fos expression was examined in the arcuate nucleus, an important center of feeding control (Schwartz et al., *Nature* 404:661-671, 2000; Cowley et al., *Nature* 411:480-484, 2001), following a single IP injection of $PYY_{3-36}$. There was a 2-fold increase in the number of cells positive for c-fos in the lateral arcuate of the rat ($PYY_{3-36}$=168±2, saline=82.7±5, n=3, P<0.0001). Likewise in Pomc-EGFP-transgenic mice (Cowley et al., *Nature* 411:480-484, 2001) IP administration of $PYY_{3-36}$ resulted in a 1.8-fold increase in the number of arcuate cells positive for c-fos (FIG. 5*b*), compared with saline control animals (FIG. 5*a*) ($PYY_{3-36}$=250±40, saline=137±15, n=5, P<0.05). IP $PYY_{3-36}$ caused a 2.6 fold increase in the proportion of POMC neurons that express c-fos ($PYY_{3-36}$=20.4±2.9%, saline=8±1.4%, n=5, P<0.006) (FIGS. 5*c* and *d*). These observations show that $PYY_{3-36}$ can act via the arcuate nucleus

Example 4

Y2 Receptors

The electrophysiological response of hypothalamic POMC neurons to administration of both $PYY_{3-36}$ and Y2A was examined. The effect of PYY on feeding in rats and mice has been established (Batterham et al., *Nature* 418:450, 2002). POMC neurons were identified using mice with targeted expression of green fluorescent protein in POMC neurons (Cowley et al., *Nature* 411:480-484, 2001). $PYY_{3-36}$ disinhibited the POMC neurons, resulting in a significant depolarization of 19 of the 22 POMC neurons tested (FIG. 5*a* inset) (10.3±2.1 mV depolarization, n=22, P<0.0003). A similar depolarization was seen with Y2A (8.7±1.8 mV depolarization, n=9, P<0.002). The depolarization caused by $PYY_{3-36}$ stimulated a significant increase in the frequency of action potentials in POMC neurons (FIG. 6*a*) (93% increase over control, P<0.05, n=22). In the whole cell mode the effect of $PYY_{3-36}$ was sometimes reversed upon washout, but only after a long latency (30 minutes). A similar washout of leptin effects upon these neurons was observed.

Figures 6A, 6B, 6C:
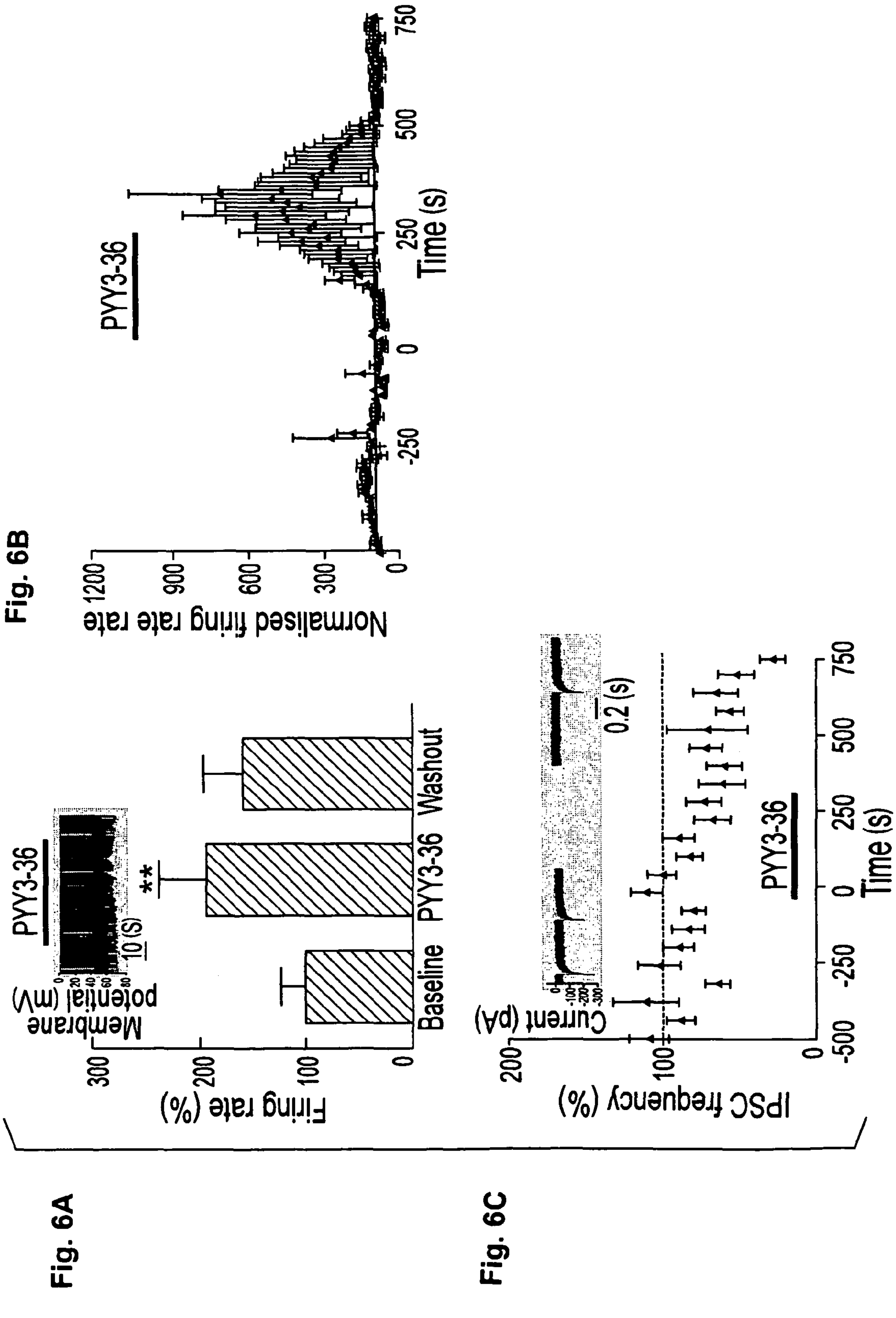
FIG. 6*a* is a tracing showing the effect of $PYY_{3-36}$ (10 nM) on the frequency of action potentials in POMC neurons (whole-cell configuration recordings; n=22)*$p<0.05$. $PYY_{3-38}$ was administered at time D for 3 minutes; baseline, −3 to 0 minute; $PYY_{3-36}$, 2-5 minutes; and wash-out, 8-11 minutes. Inset shows a representative recording of membrane potential and action potential frequency.
FIG. 6*b* is a graph of the effect if $PYY_{3-38}$ (10 nM) on the frequency of action potentials in loose cell-attached patch recordings (n=8). Data from individual cells were normalized to the firing rate for the 200 s before $PYY_{3-38}$ addition.
FIG. 6*c* is a tracing and a graph of the effect of $PYY_{3-38}$ (50 nM) on spontaneous IPSCs onto POMC neurons (n=13). Inset shows a representative recording of IPSCs before and after $PYY_{3-36}$ (50 nM), respectively. Results in FIGS. 6*a*-6*c* are expressed as mean±s.e.m.

To exclude effects of cellular rundown, or seal deterioration, the effects of $PYY_{3-36}$ in the "loose cell-attached" (or extracellular) configuration was examined. $PYY_{3-36}$ caused a reversible 5-fold increase in the frequency of action potentials in loose cell-attached recordings of POMC neurons (FIG. 6*b*). This increase in firing rate occurred with the same latency as $PYY_{3-36}$ reduced the frequency of inhibitory postsynaptic currents (IPSCs) onto all 13 POMC neurons tested (FIG. 6*c*) (51.9±9.2% reduction, n=13, P<0.0001), indicating a reduced frequency of GABA release onto POMC neurons. Interestingly, the firing rate of POMC neurons returned to basal, in spite of continued inhibition of IPSCs. A similar effect upon IPSC frequency was seen with Y2A (44.4±9.3% reduction, n=8, P<0.004) suggesting this effect to be via Y2R. $PYY_{3-36}$ (25 nM) caused a hyperpolarization (5.2±1.16 mV, P<0.004, n=5) of unidentified, but presumably NPY-containing, non-POMC, neurons in the arcuate nucleus. There is a tonic GABAergic inhibition of POMC neurons by NPY neurons (Cowley et al., *Nature* 411:480-484, 2001) and these results suggest that $PYY_{3-36}$ acts by inhibiting NPY neurons, thus decreasing this GABAergic tone and consequentially disinhibiting POMC neurons. The effect of Y2A on peptide secretion was also examined using hypothalamic explants (Kim et al., *J. Clin. Invest*. 105:1005-11, 2000). Y2A significantly decreased NPY release, with a concomitant increase in α-MSH release from hypothalamic explants (Batterham et al., *Nature* 418:450, 2002). Taken together these observations show that $PYY_{3-36}$ modulates both the NPY and melanocortin systems in the arcuate nucleus.

Example 5

Analysis of the POMC Enhancer in Transgenic Mice

A strain of transgenic mice has been generated that expresses green fluorescent protein under the transcriptional control of the mouse POMC genomic sequences, including a region located between −13 kilobases (kb) and −2 kb that is required for accurate neuronal expression (see above, e.g. Example 2, and Cowley et al., *Nature* 411:480, 2001, which is herein incorporated by reference). Additional lines of transgenic mice were then generated. The starting material for these experiments was either a 4 kb fragment of the rat POMC gene extending from a position approximately −4000 base pairs (bp) 5' to the transcriptional start site through to position +64 in the first exon or a 10 kb mouse genomic clone including approximately 2 kb of 5' flanking sequences. The complete POMC gene is composed of 3 exons and 2 introns, and approximately 2 kb of 3' flanking sequences (see Rubinstein et al., *Neuroendocrinol.* 58:373, 1993, herein incorporated by reference).

A cosmid genomic library was constructed from 129S6 strain mouse genomic DNA partially cut with the EcoRI restriction endonuclease. This library was screened with probes generated from the original 10 kb mouse POMC clone. This screen resulted in the isolation of several overlapping POMC genomic clones, which were used to construct a transgene vector for microinjection that included approximately 13 kb of 5' flanking sequences, the 6 kb POMC gene, and 8 kb of 3' flanking sequences for a total size of 27 kb. An artificial oligonucleotide sequence was introduced into exon 3 of the coding sequence to permit the unequivocal identification and quantification of mRNA transcribed from the transgene compared to the endogenous mouse POMC gene. Two additional transgenes were constructed, one that was truncated at the −2 kb side 5' to the POMC gene and the other that was truncated at the +2 kb side 3' to the POMC gene (see Young et al., *J. Neurosci.* 18:6631, 1998, herein incorporated by reference). Expression studies in this line of transgenic mice demonstrated that DNA sequences between −13 and −2 kb 5' to the POMC gene are necessary for eutopic, neuron-specific expression in the arcuate nucleus of the hypothalamus and the nucleus of the tractus solitarius. However, all the transgenes were appropriately expressed in the pituitary gland, consistent with the location of pituitary-specific DNA regulatory elements within the proximal −400 bp of the POMC promoter.

Figure 7:
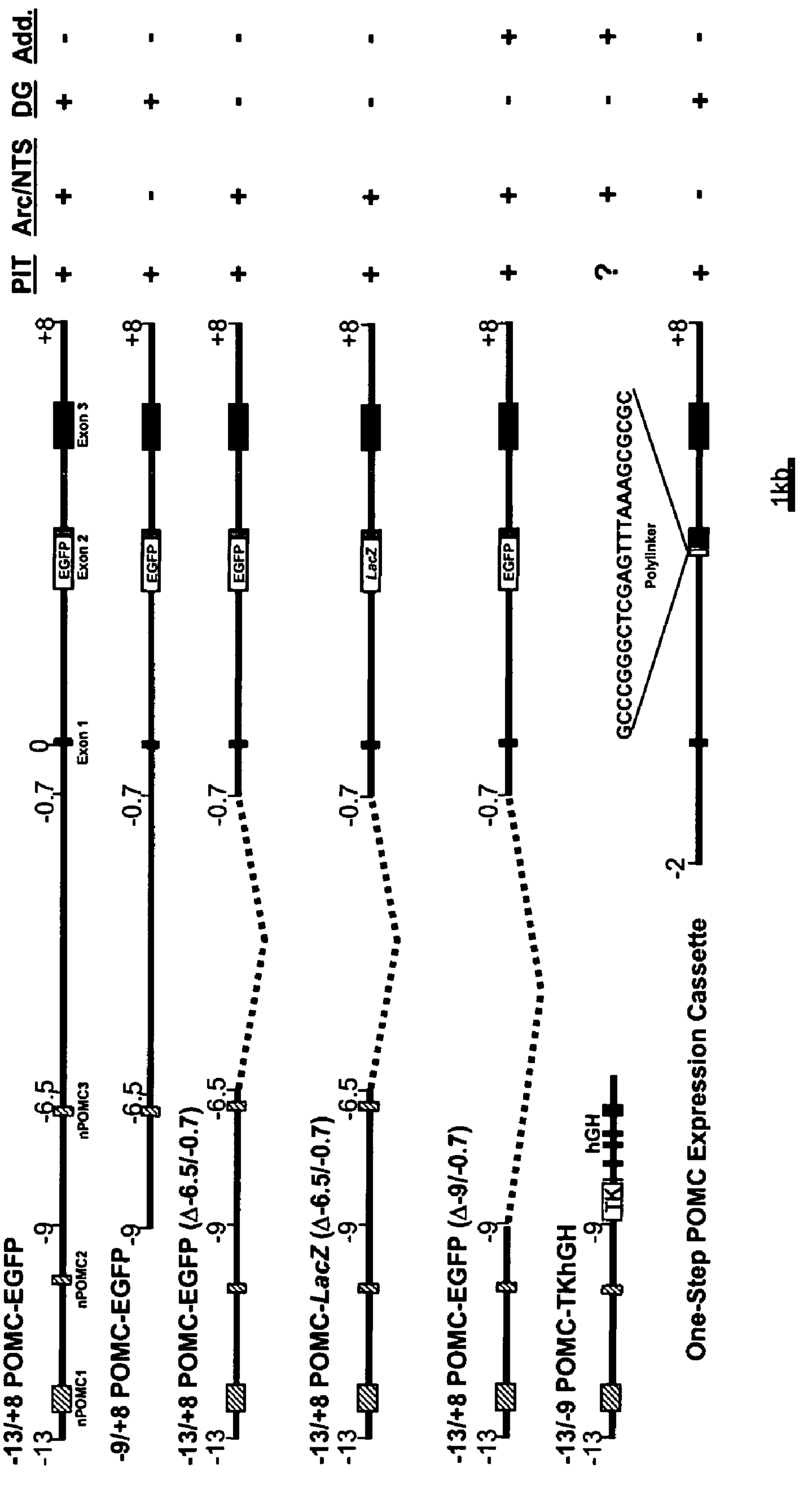
FIG. 7 is a schematic diagram of transgenes carrying variable lengths or deletions of 5' flanking sequences of the mouse POMC gene. The EGFP gene was inserted into the second exon immediately before the site of translational initiation. A polyadenylation signal from the large T antigen of the SV40 virus was included immediately adjacent and 3' to the EGFP gene. Black boxes are mouse POMC exons. Open boxes, EGFP or LacZ as indicated. Striped boxes are nPOMC1, nPOMC2, and nPOMC3 sites. The white box is the TK minimal promoter in front of the hGH structural gene. Restriction endonuclease sites used for subcloning include a BamHI site at position approximately −9 kb and two Sma1 sites at positions approximately −6.5 kb and −0.7 kb upstream of the transcriptional initiation start site. Right: Plus signs indicate that the transgene is expressed correctly in POMC pituitary corticotroph and melanotroph cells (PIT), POMC hypothalamic arcuate and nucleus tractus solitarius neurons (Arc/NTS), immature granular layer neurons of the dentate gyrus of the hippocampus (DG), or additional sites in the central nervous system (Add) and minus signs indicate the absence of expression. The one-step POMC expression cassette has a polylinker inserted into a StuI restriction site located immediately 5' to the translational start codon in exon 2.
Figure 8A:
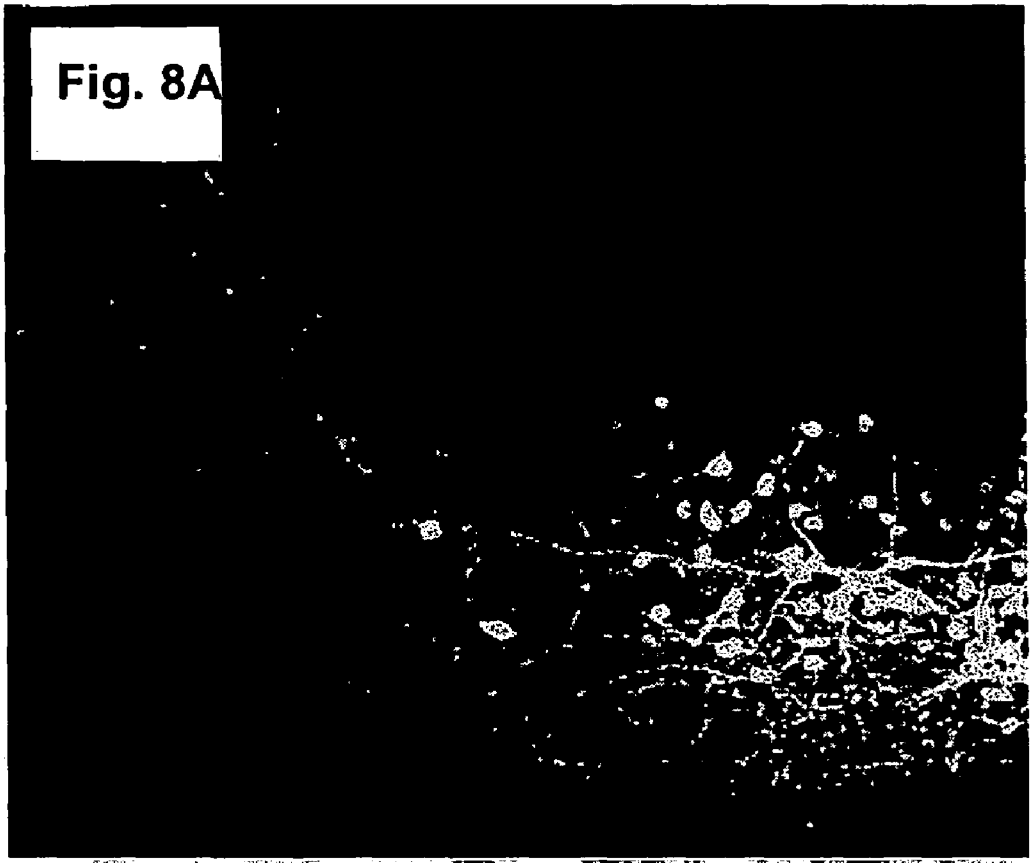
FIG. 8*a* is a digital image showing fluorescence in POMC neurons of the arcuate nucleus of the hypothalamus in a −13/+8 POMC-EGFP (delta −6.5/0.7) transgenic mouse.

An additional series of transgenes containing the EGFP reporter gene were constructed as illustrated in FIG. 7. Truncation of the 5' flanking sequences to a BamHI restriction site located at position −9 kb resulted in a loss of arcuate and NTS neuronal expression, but did not affect pituitary expression, suggesting that the essential arcuate and nucleus of the tractus solitarius (NTS) neuron-specific regulatory elements are contained in the 4 kb between nucleotide positions −13 and −9 kb. Furthermore, an internal deletion of genomic 5' flanking genomic sequences between positions approximately −6.5 to −0.7 or between −9 to 0.7 kb did not affect the positive transgene expression in either hypothalamic neurons (see FIG. 8*a* for a representative histologic section illustrating the robust expression of the fluorescent protein in arcuate neurons) or the pituitary cells. This indicates the position independence of the neural regulatory elements relative to the basal promoter. Virtually every transgenic strain produced with transgenes including the distal 4 kb of mouse POMC regulatory elements (approximately −13 to −9 kb from the transcriptional start site) displayed a high penetrance of reporter transgene expression in the neurons of the arcuate nucleus of the hypothalamus and the nucleus of the tractus solitrius, indicating that the transcriptional regulatory elements contained within the 4 kb of DNA sequence are insulated from the effects of random chromosomal integration position in common with known locus-control type enhancer elements.

Another transgene illustrated in FIG. 7 comprising the mouse POMC enhancer element from approximately −13 to −6.5 kb but with an internal deletion of the sequences from approximately −6.5 to −0.7 kb directed eutopic transgene expression of a LacZ cassette encoding beta-galactosidase to neurons of the arcuate nucleus, nucleus tractus solitarius, and corticotroph and melanotroph cells of the pituitary gland (not shown in a figure).

Figure 8B:
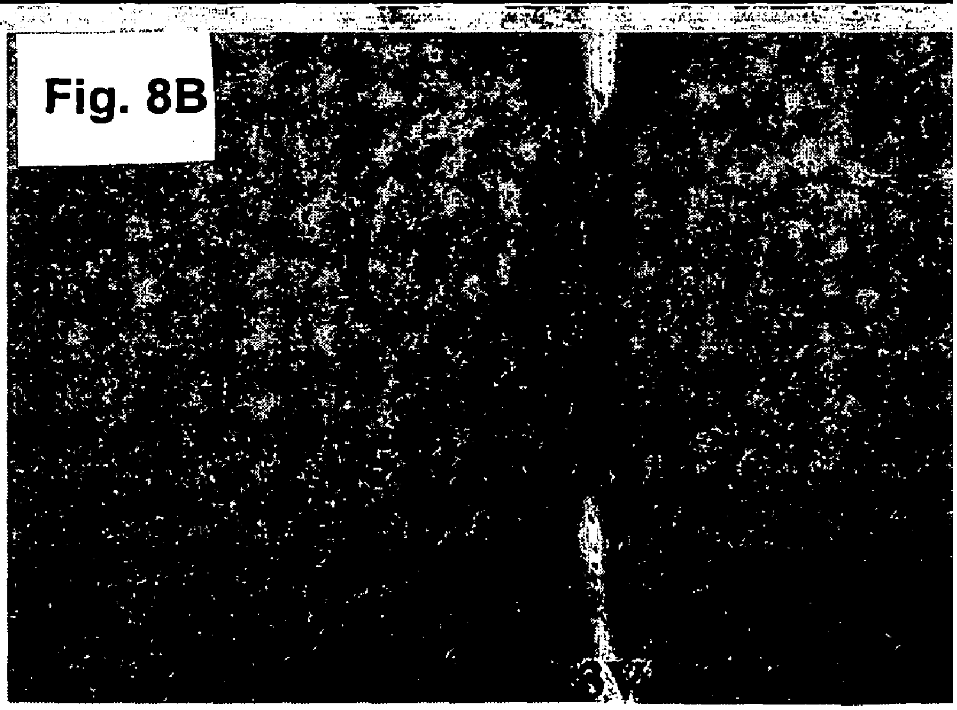
FIG. 8*b* is a digital image showing immunohistochemical localization of human growth hormone (hGH) using an antisera specific for hGH. POMC neurons in the arcuate nucleus of a −13/−9 POMC-TKhGH transgenic mouse express the hGH marker. 3V, third ventricle.

A transgene containing the distal 4 kb of mouse POMC 5' genomic sequences between approximately −13 and −9 kb ligated to a minimal herpes simplex viral thymidine kinase (TK) promoter and human growth hormone reporter transgene (FIG. 7) was produced, and transgenic mice carrying this construct were generated. This region of the mouse POMC genomic sequences conferred hypothalamic arcuate and NTS neuronal-specific expression of the human growth hormone marker (FIG. 8*b*).

The minimal TK promoter has been used previously in conjunction with proximal pituitary-specific POMC regulatory elements (see Liu, et al 1992). In these studies, no intrinsic capacity of the TK promoter to cause reporter gene expression in POMC cells of transgenic mice was observed. Thus, expression of the hGH marker in these transgenic mice indicate that the 4 kb of distal mouse POMC genomic sequences contain a classically defined position- and promoter-independent transcriptional enhancer with specific activity for targeting high-level gene expression to POMC neurons, in vivo.

To facilitate the generation of additional transgenic animals with expression of marker genes or polypeptides from POMC gene regulatory sequences, a one-step POMC expression cassette was made (FIG. 7). This expression cassette includes a polylinker with the nucleotide sequence GCCCGGGCTCGAGTTTAAAGCGCGC (SEQ ID NO: 37) inserted into a StuI restriction site present in the 5' untranslated region of exon 2 immediately upstream of the translational start codon for POMC. The polylinker comprises sequences for the uncommon SrfI, SmaI, XhoI, DraI, and BssHII restriction enzymes. Nucleotide sequences encoding a marker or polypeptide of interest can be ligated into one or more of these uncommon restriction sites in a single cloning step. This is not possible with the natural StuI site in this location, because numerous other StuI sites are present in the POMC gene. The position of the polylinker in exon 2 is advantageous because it assures that foreign DNA sequences, with an appropriate Kozak consensus translational start site, ligated into this position will be translated into their encoded protein but the downstream POMC sequences will not be translated. The polylinker sequence can also be used as an oligonucleotide hybridization probe to demonstrate cell-specific expression of the transgene mRNA by in situ hybridization histochemistry.

The POMC expression cassette comprising POMC enhancer elements located approximately between −2 kb and the transcriptional start site confers transgene expression specifically to the pituitary corticotrophs and melanotrophs and the immature neurons of the granular cell layer of the dentate gyrus of the hippocampus (data not show in a figure). The addition of other POMC enhancer elements located between approximately −13 and −6.5 kb to the one-step expression cassette further confers transgene expression to neurons of the arcuate nucleus and the nucleus of the solitary tract.

Example 6

Exemplary Screening Protocol

A number of lines of transgenic mice have been produced that carry a transgene including a POMC enhancer element operably linked to nucleic acid sequence encoding a marker. Histological sections can readily be prepared from these, or other lines of transgenic mice carrying a POMC regulatory region operably linked to a nucleic acid sequence encoding a marker. These sections can be used to screen agents, such as chemical compounds, proteins, small molecules or salts, in order to identify an agent that affects caloric intake, food intake, or appetite, as described herein.

Coronal slices, from about 140 to about 400 μm thick, containing neurons form the ARC of mice carrying a POMC gene or regulatory element operably linked to a maker, wherein the marker is expressed in the POMC neurons in the ARC. In one embodiment, suitable sections are produced from a male, four week old mouse expressing GFP from the POMC promoter, such as one of the lines of mice disclosed herein. It should be noted that the age and sex of the animal is not a limitation, as female mice as well as older and younger mice can be used. These sections are then incubated with an agent of interest, and an electrophysiological parameter of the POMC neurons is measured. A change in this electrophysiological parameter indicates that the agent affects caloric intake, food intake, appetite and/or energy expenditure.

In one example, 180 μm thick slices of the ARC are maintained in (in mM) [NaCl, 126; KCl, 2.5; $MgCl_2$, 1.2; $CaC2_2H_2O$, 2.4; $NaH_2PO_4.H_2O$, 1.2; $NaHCO_3$, 21.4; Glucose, 11.1] (Krebs) at 35° C. and saturated with 95% $O_2$ 5% $CO_2$ for 1 hour (hr) prior to recordings. Recordings are made in Krebs at 35° C. Slices are visualized on an Axioskop FS2 (Zeiss) through standard infra red optics and using epifluorescence through a FITC filter set (see FIG. 1*c*). Whole cell or loose cell attached recordings are made from fluorescent neurons using an Axopatch 1D amplifier (Axon Instruments) and Clampex 7 (Axon Instruments).

Resting membrane potentials and action potential frequencies are determined using an event detection protocol on a PowerLab system (AD Instruments, Mountain View, Calif.) to average expanded traces of the membrane potential. Alternatively, an event detection software package, such as Synaptosoft (Gaegin software), is used to plot instantaneous frequencies. Agents are applied to the bath over a specific time period, such as but not limited to, about one to about 15 minutes. The resting membrane potential is stable for up to an hour in cells treated with Krebs alone.

Current to voltage (I-V) relationships are established using a step protocol; (−60 mV holding potential, sequentially pulsed (40 ms) from −120 to −50 mV, cells were returned to −60 mV for 2 s between voltage steps). The protocol is repeated after addition of an agent of interest. The net current is the difference between the two I-V relationships are used to confirm that the agent is exerting a postsynaptic effect. Similarly slow voltage ramps (5 mV/s from −100 to −20 mV) before and 10 minutes after the addition of the agent (such as, but not limited to, a concentration of 1 nM-10 mM, e.g. at 100 nM) can be used to determine if a postsynaptic effect is occurring.

GABAergic IPSCs are recorded using a CsCl internal electrode solution (in mM) [CsCl, 140; Hepes, 10; $MgCl_2$, 5; Bapta, 1; (Mg)-ATP, 5; (Na)GTP, 0.3]. Addition of blockers of excitatory currents are used to allow the analysis of IPSC frequency in isolation. Both mini IPSCs and large amplitude (presumably multisynaptic) IPSCs are observed in the untreated slices. TTX (1 mM) abolishes large IPSCs. Data is acquired before and after addition of agent at, for example, a −50 mV holding potential in 2 seconds sweeps every 4 seconds. Mini postsynaptic currents are analyzed using Axograph 4 (Axon Instruments) or Synaptosoft. IPSCs and excitatory postsynaptic currents (EPSCs) are distinguished on the basis of their decay constants and sensitivity to specific blocking agents; picrotoxin (100 mM) blocks IPSCs.

Exemplary parameters that can be analyzed are:

1. Analyzing membrane potential in POMC neurons as compared to a control, such as a POMC neuron in an untreated section or a section incubated with a control agent. This allows assessment of whether an agent increases or decreases the activity of POMC neurons.

2. Analyzing action potential firing rate in POMC neurons as compared to a control, such as a POMC neuron in an untreated section or a section incubated with a control agent. This allows assessment of whether an agent increases or decreases the activity of POMC neurons.

3. Analyzing IPSC frequency onto POMC neurons as compared to a control, such as an untreated section or a section incubated with a control agent. This allows assessment of whether an agent increases or decreases the activity of NPY neurons.

Any change in one or more of these parameters identifies the agent as affecting caloric intake, appetite, food intake, and/or energy expenditure when a therapeutically effective amount of the agent is administered to a subject. Thus, in one embodiment, these data are interpreted by determining the effect of the agent on the activity of POMC neurons (as shown by membrane potential or action potential firing rate) and/or NPY/AGRP neurons (as shown by the IPSC frequency in POMC neurons). Agents that increase the activity of NPY neurons and/or decrease the activity of POMC neurons will increase caloric intake, food intake and/or appetite, and decrease energy expenditure. Agents which decrease the activity of NPY neurons and/or increase the activity of POMC neurons will decrease caloric intake, food intake and/or appetite and/or increase energy expenditure.

Example 7

In Vitro Assessment of Ghrelin, a Known Appetite Stimulant

Slices are of the ARC from POMC-EGFP mice (see Example 1 for a description of the animals) were maintained in (in mM) [NaCl, 126; KCl, 2.5; $MgCl_2$, 1.2; $CaCl_2.2H_2O$, 2.4; $NaH_2PO_4.H_2O$, 1.2; $NaHCO_3$, 21.4; Glucose, 11.1] (Krebs) at 35° C. and saturated with 95% $O_2$ 5% $CO_2$ for 1 hour (hr) prior to recordings. Recordings were made in Krebs at 35° C. Slices were visualized on an Axioskop FS2 (Zeiss) through standard infra red optics and using epifluorescence through a FITC filter set. Whole cell (FIG. 12*a* and FIG. 12*b*) or loose cell attached (FIG. 12*c*) recordings were made from fluorescent neurons using an Axopatch 1D amplifier (Axon Instruments) and Clampex 7 (Axon Instruments).

GABAergic IPSCs were recorded using a CsCl internal electrode solution (in mM) [CsCl, 140; Hepes, 10; $MgCl_2$, 5; Bapta, 1; (Mg)-ATP, 5; (Na)GTP, 0.3]. Addition of blockers of excitatory currents allowed the analysis of IPSC frequency in isolation. Both mini IPSCs and large amplitude (presumably multisynaptic) IPSCs were observed in the untreated slices. TTX (1 mM) abolished large IPSCs. Data was acquired before and after addition of agent at a −50 mV holding potential in 2 second sweeps every 4 seconds. Picrotoxin (100 mM) blocked all IPSCs.

Figures 12A, 12B, 12C:
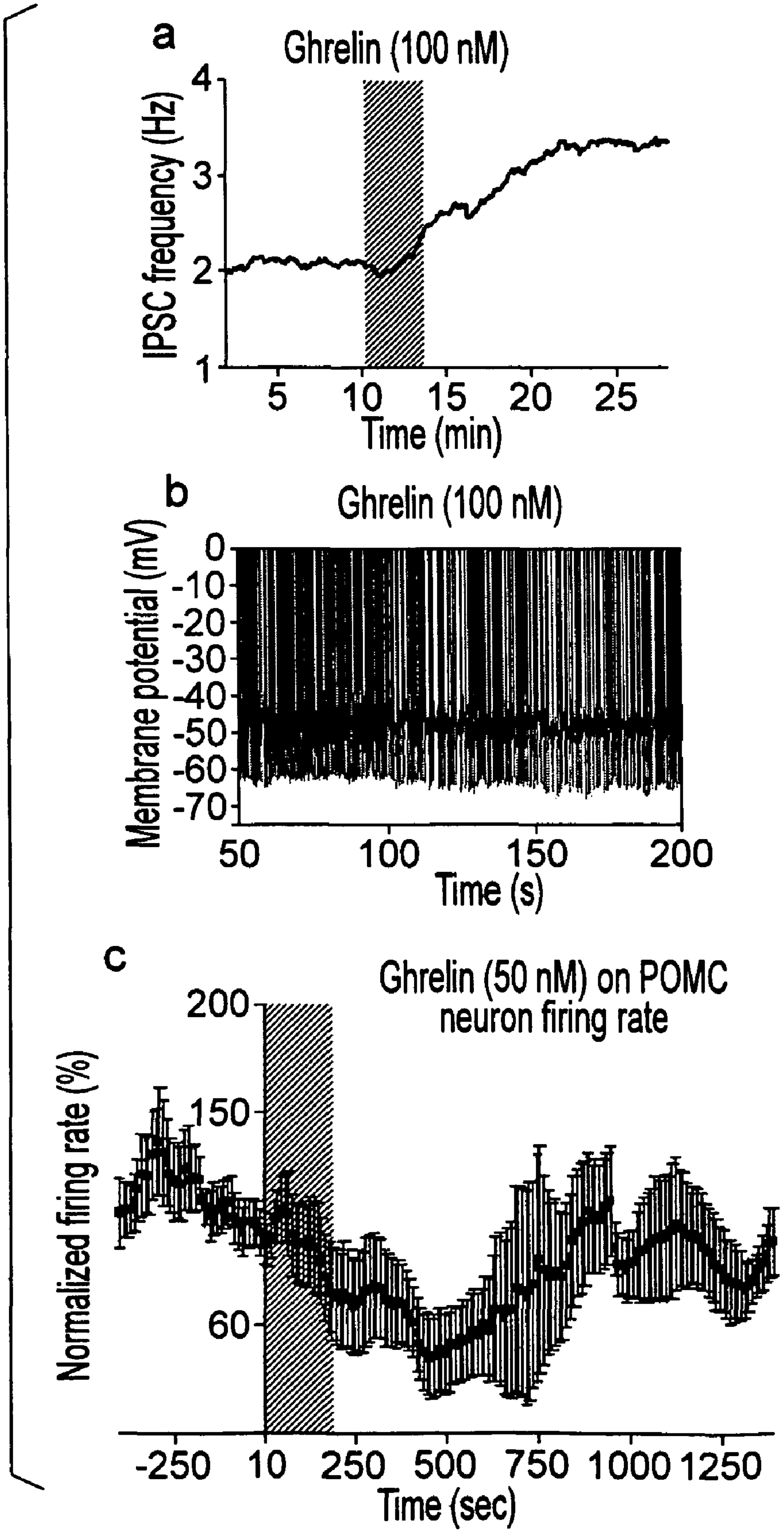
FIG. 12*a* is a graph demonstrating that Ghrelin increases the frequency of spontaneous synaptic GABA release onto POMC neurons. Results shown in the figure are representative of 18 experiments. Increased release of GABA from NPY neurons is shown, thus Ghrelin is increasing the activity of NPY neurons.
FIG. 12*b* is a graph demonstrating that Ghrelin mildly hyperpolarizes POMC neurons and decreases the spontaneous activity of POMC neurons. Results shown in the figure are representative of 34 experiments.
FIG. 12*c* is a graph demonstrating that Ghrelin decreases the frequency of action potentials in POMC neurons, an effect that reverses with washout of the drug. Ghrelin induced a 50% decrease of the normalized mean (+/−s.e.m.) POMC neuron firing rate. These recordings were made in loose-cell-attached mode.

IPSC frequencies were analyzed using Synaptosoft (Gaegin software), to determine instantaneous IPSC frequencies (FIG. 12*a*). Resting membrane potentials are determined using an event detection protocol on a PowerLab system (AD Instruments, Mountain View, Calif.) to average expanded traces of the membrane potential (FIG. 12*b*). Action potential firing rates were determined in loose cell attached mode and the recorded data was analyzed using Synaptosoft to determine instantaneous frequencies. Ghrelin (50 nM) was applied to the bath over three minutes. The resting membrane potential was stable for up to an hour in cells treated with Krebs alone.

The results of the addition of Ghrelin on IPSC frequency of POMC neurons are shown in FIG. 12*a*. An increase in the frequency of IPSCs in POMC neurons was detected. This is caused by NPY neurons. Thus an increase in the activity of NPY neurons is demonstrated. FIG. 12*b* shows the effect of Ghrelin on the resting membrane potential of POMC neurons. Ghrelin hyperpolarized POMC neurons, mean 1.47±0.7 mV; $p<0.03$. The activity of POMC neurons was decreased by the addition of Ghrelin. FIG. 12*c* shows the action potential firing rate in POMC neurons. The activity of POMC neurons was inhibited by Ghrelin. Thus, Ghrelin, an agent known to increase feeding, caloric intake, and appetite, and decrease energy expenditure, decreases the resting membrane potential (FIG. 12*b*) and action potential firing rate of POMC neurons (by 50%, see FIG. 12*c*), increases the frequency of IPSCs in POMC neurons (FIG. 12*a*), and increases the activity of NPY neurons.

Example 8

In-Vitro Assessment of Fenfluramine, a Known Appetite Suppressant and Weight Loss Agent Slices are of the ARC from POMC-EGFP [the line that the may 2000 nature paper describes] were maintained in (in mM) [NaCl, 126; KCl, 2.5; $MgCl_2$, 1.2; $CaCl_2.2H_2O$, 2.4; $NaH_2PO4.H_2O$, 1.2; $NaHCO_3$, 21.4; Glucose, 11.1] (Krebs) at 35° C. and saturated with 95% $O_2$ 5% $CO_2$ for 1 hour (hr) prior to recordings. Recordings were made in Krebs at 35° C. Slices were visualized on an Axioskop FS2 plus (Zeiss) through standard infra red optics and using epifluorescence through a endow-GFP filter set (Chroma Technology Corp). Whole cell or loose cell attached recordings (both were used, results from whole cell recordings are shown in FIG. 13*b*; results from loose cell attached are shown in FIG. 13*a*) were made from fluorescent neurons using an Axopatch 200B amplifier (Axon Instruments) and Clampex 8 (Axon Instruments).

Figure 13A:
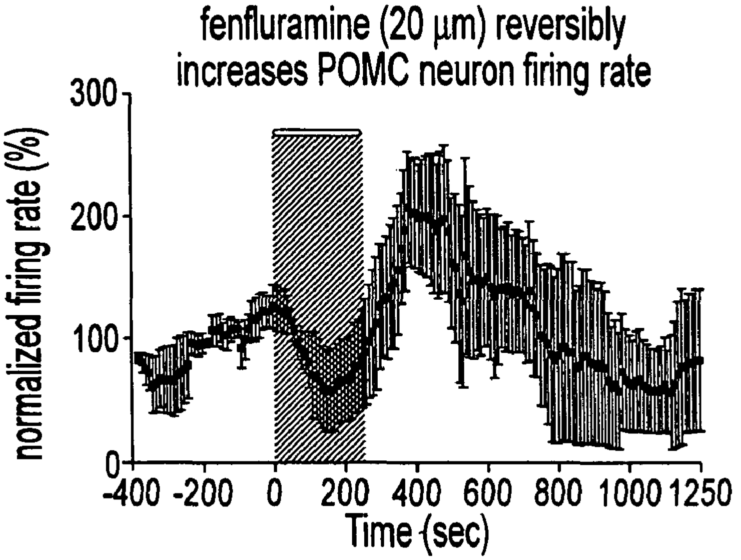
FIG. 13*a* shows the results obtained using a loose-cell-attached mode. d-FEN (20 microM) induced a doubling of the mean (+/−s.e.m.) POMC-neuron firing rate (n=3). This effect was reversed with drug washout.
Figure 13B:
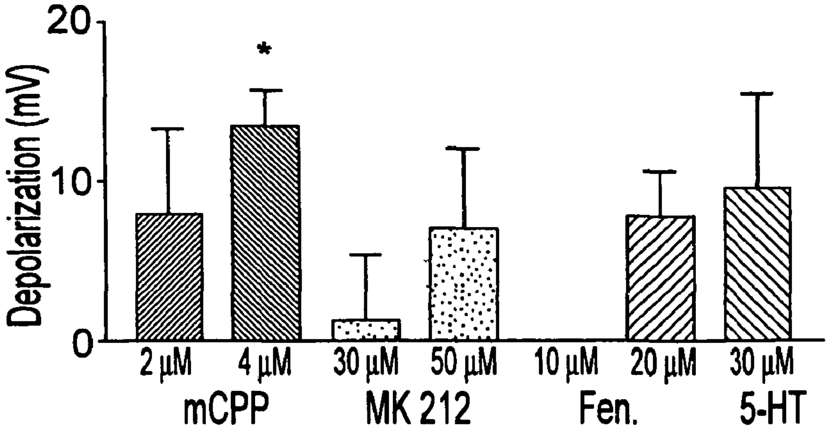
FIG. 13*b* is a graph of the mean (+/−s.e.m.) peak depolarization of POMC neurons (n=4-8 per dose) bathed with d-FEN, 5-HT mCPP or MK 212 using conventional whole cell recordings.

Action potential firing rates were determined in loose cell attached mode and the recorded data was analyzed using Synaptosoft to determine instantaneous frequencies (FIG. 13*a*). Resting membrane potentials and depolarizations were determined using an event detection protocol on a PowerLab system (AD Instruments, Mountain View, Calif.) to average expanded traces of the membrane potential (FIG. 13*b*). Serotonin receptor agonists were applied to the bath at the specified concentrations over four minutes. The resting membrane potential was stable for up to an hour in cells treated with Krebs alone.

Fenfluramine (20 μM) caused a two fold increase in the frequency of action potentials in POMC neurons (FIG. 13*a*; n=3). Thus fenfluramine increased the activity of POMC neurons. In separate experiments Fenfluramine also depolarized POMC neurons (FIG. 13*b*) in a dose dependent manner. Thus, by another test Fenfluramine increases the activity of POMC neurons. The non-selective serotonin receptor agonist serotonin (5-HT) also increased the resting membrane potential (depolarized) POMC neurons. The effect of serotonin and fenfluramine on POMC neurons is likely mediated by the 5-HT 2C R because 5-HT 2C R selective agonists mCPP and MK 212 also depolarized POMC neurons (FIG. 13*b*).

Example 9

Sequences and the Identification of the nPOMC1, nPOMC2, and nPOMC3 Elements

Figure 9B:
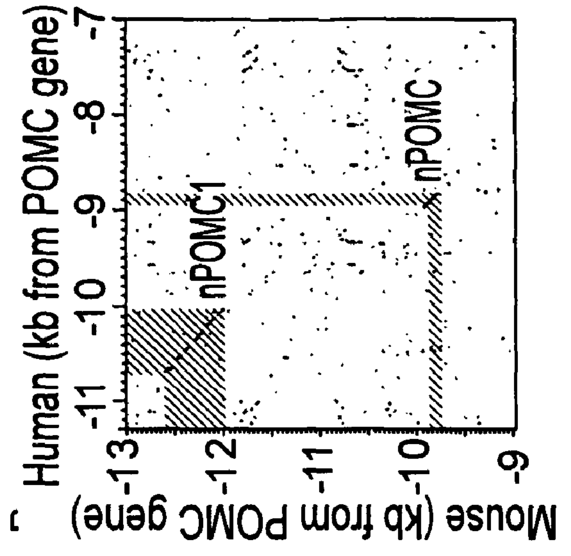
FIG. 9*b* is a similar analysis performed with the Dotter program using the 4 kb between −13 and −9 of the mouse POMC gene and 15 kb of the human 5' flanking region. Diagonal lines inside the gray-shaded areas indicate the conserved sites nPOMC1 and nPOMC2.
Figure 9A:
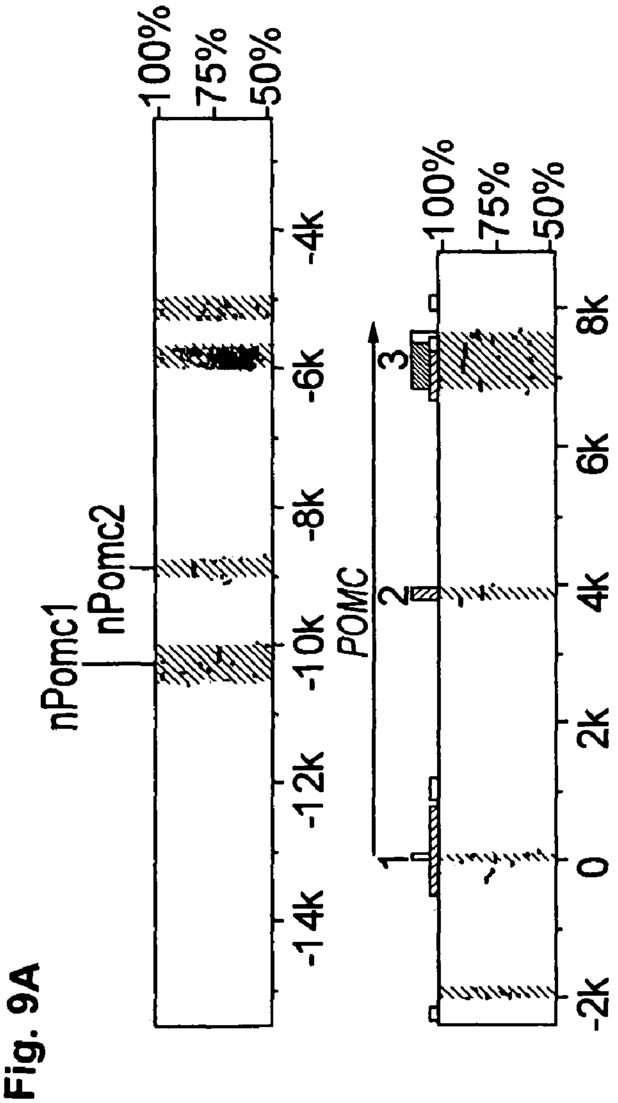
FIG. 9*a* is a PIP Maker multiple sequence alignment between 24 kb containing the human POMC gene, 4 kb of the mouse 5' flanking region located between 9 and 13 kb from the TATA box, and the three exons with short flanking sequences obtained from GenBank (J00610, J00611, and J00612). Conserved regions are indicated with horizontal black lines on gray shaded background. Exons 1, 2, and 3 are indicated; repetitive intergenic regions are present at −5 kb and −6 kb; two highly conserved intergenic regions longer than 100 bp are identified as nPOMC1 and nPOMC2. The gray and white horizontal boxes indicated GC-rich regions.

The complete nucleotide sequence of the 4 kb of 129S6 substrain mouse POMC genomic DNA from approximately −13 kb to −9 kb relative to the transcriptional start site was obtained from the cosmid clones. A multiple alignment sequence comparison was performed with a public human database BAC sequence containing the human POMC gene on chromosome 2 using the web-based program PIP Maker (Percentage Identity Plot) and the program named Dotter. The two programs, which use a completely different sequence comparison algorithm, found the same two highly conserved regions between mouse and human 5' flanking POMC gene sequences (FIG. 9). These two homology islands have been termed nPOMC1 and nPOMC2 for neural POMC regulatory elements 1 and 2.

FIGS. 10*a*-10*c* illustrate a sequence alignment of the nPOMC1 and nPOMC2 elements from a variety of mammalian species. In addition to the primary sequence, the distance between both sites to the TATA box is also conserved in the human and mouse POMC genes. The nPOMC1 site extends for approximately 450 bp with an overall mouse/human similarity of 65% having a 190 bp core with a maximal conservation of 80% (the human and bovine similarity is even higher, at 85%). This core is at −10.5 and −12.2 kb from the human and mouse TATA box, respectively. The core is located 1.7 or 2.3 kb upstream of human and mouse nPOMC2, respectively. The site nPOMC2 has a 153 bp region from which 138 are identical between mouse and human (90% of similarity). It is located at −8.9 and −9.9 kb from the human and mouse TATA box, respectively.

Without being bound by theory, these two small and highly conserved areas, embedded within several kb of heterogeneous genomic sequences, resemble the exon-intron differences within the transcriptional unit. Interestingly, the similarities between mouse and human exon 1, 2 and 3 of 64%, 87% and 82%, respectively, are not higher than the interspecies identity for nPOMC1 and nPOMC2 (FIGS. 11*a*-11*b*).

A Clustall comparison of 280 bp of the proximal human and mouse POMC promoters show 68% of similarity in a region that contains all cis-acting elements necessary for basal (e.g. TATA and GC boxes) and pituitary specific expression (e.g. T-Pit, Ptx1 and PP1). Using degenerate oligonucleotide primers to amplify corresponding genomic regions from other mammalian species and sequencing of the PCR fragments, it was confirmed that nPOMC1 and nPOMC2 are also highly conserved in bovine, hamster, and rabbit genomic DNA. In addition, a bovine genomic library was screened using the bovine nPOMC1 PCR fragment as a radiolabeled probe. One of the positive phage clones also contains nPOMC2 and POMC exon 1 indicating that these two regulatory regions are syntenic with the TATA box within 15 kb, similar to the human and mouse. An internal portion of bovine nPOMC2 that was amplified from this clone shows 90% similarity with the human.

The sequences of the rat nPOMC1 and nPOMC2 were obtained from a BLAST comparison of the rat genome data base and they are highly similar to the mouse sequence. The relative order of the two elements and the relative distances between themselves and between each element and the transcriptional start site are also highly similar to both the mouse and the human genes (FIGS. 14*a*-14*g*). Furthermore, the 129 mouse POMC genomic sequence is nearly identical to the C57BL/6J POMC genomic sequence now available in GenBank. The nucleotide sequences spanning the nPOMC1, and nPOMC2 elements together with the precise nucleotide positions on human chromosome 2, mouse chromosome 12, and rat chromosome 6 are shown in FIG. 14. BLAST analyses indicate that the complete nPOMC1 and nPOMC2 elements are previously unidentified and uncharacterized sequences and appear to be unique to the POMC gene locus. Thus, one of skill in the art can readily generate transgenic mice carrying a transgene including any of these regions of the POMC gene, operably linked to a marker (such as, but not limited to, growth hormone or GFP).

The adipostatic hormone leptin not only activates POMC neurons but also stimulates transcription of the POMC gene in the hypothalamus presumably through a JAK kinase/STAT3-dependent pathway. The web-based program Mat Inspector was used to localize STAT3 DNA binding sites within 11.5 kb of 5' flanking regions of the human POMC gene. Eight sites were detected that share high homology with the consensus core TTCCNGGAA (SEQ ID NO: 35). Interestingly, only one site entirely matches this consensus sequence and it is located within the highly conserved NPOMC1 site and 50 bp downstream of another STAT3-like site (FIG. 10*b*). This similarity suggests that nPOMC1(3' half) may be a leptin-responsive element within the POMC gene. The sites are slightly less well conserved in the other genomic sequences available. Another potentially interesting short DNA sequence present in the 5' half of nPOMC1 that is 100% identical among all five mammalian species is CTAATGGATGTGCATTA (SEQ ID NO: 36). Excluding the 5° C., the remaining 16 nucleotides contain an imperfect (12/16) palindrome that could be a symmetrical DNA-protein binding site.

A BLAST comparison of mouse POMC genomic sequences between −9 and −0.8 kb and human POMC genomic sequences between −7 and −0.8 kb revealed an additional homology island of approximately 140 base pairs that was termed nPOMC3. Further BLAST comparisons with the rat genome database also identified the same element in a corresponding region of the rat POMC gene. The sequence of mouse, human, and rat nPOMC3 elements are shown in FIGS. 11*a*-11*b* with their exact nucleotide positions on chromosomes 12, 2, and 6 respectively. The sequence alignments for nPOMC3 among the three mammalian species is shown in FIG. 10*c*. The nucleotide sequences spanning the nPOMC3 elements together with the precise nucleotide positions on human chromosome 2, mouse chromosome 12, and rat chromosome 6 are shown in FIGS. 14*a*-14*g*. BLAST analyses indicate that the complete nPOMC3 element is a previously unidentified and uncharacterized sequence and appears to be unique to the POMC gene locus. Thus, one of skill in the art can readily generate transgenic mice carrying a transgene including any of these regions of the POMC gene, operably linked to a marker (such as, but not limited to, growth hormone or GFP).

Additional percentage identities were calculated for nPOMC1, nPOMC2, and nPOMC3. The calculated percentage identities are as follows:

nPOMC1 (5' half) (208 base pairs) 57% across 5 species or 65% across 3 species (human, mouse, and rat)

nPOMC1 (3' half) (326 base pairs) 69% across 3 species (human, mouse, and rat)

nPOMC1 complete (534 base pairs) 67% across 3 species (human, mouse, and rat)

nPOMC2 (234 base pairs) 75% across 5 species or 78% across 3 species (human, mouse, and rat)

nPOMC3 (145 base pairs) 78% across 3 species (human, mouse, and rat)

It will be apparent that the precise details of the methods or compositions described may be varied or modified without departing from the spirit of the described invention. We claim all such modifications and variations that fall within the scope and spirit of the claims below.

The invention claimed is:

1. An isolated proopiomelanocortin enhancer element, comprising the nucleic acid sequence set forth as SEQ ID NO: 9, wherein the isolated proopiomelanocortin enhancer element elevates transcription of a heterologous coding sequence in a host cell, wherein the proopiomelanocortin element is isolated from the adjacent 5' or 3' nucleic acid sequences of an endogenous chromosome comprising the proopiomelancortin gene.

2. The isolated proopiomelanocortin enhancer element of claim 1, consisting of the nucleic acid sequence set forth as SEQ ID NO: 9.

3. The isolated proopiomelanocortin enhancer element of claim 1, comprising a 5' half and a 3' half, wherein the 5' half and the 3' half have the nucleic acid sequence set forth, respectively, as a) SEQ ID NO: 1 and SEQ ID NO: 6;

b) SEQ ID NO: 4 and SEQ ID NO: 7; or c) SEQ ID NO: 5 and SEQ ID NO: 8.

4. The isolated proopiomelanocortin enhancer element of claim 1, comprising nucleic acid sequence as set forth as SEQ ID NO: 1 and the nucleic acid sequence set forth as SEQ ID NO: 6.

5. The isolated proopiomelanocortin enhancer element of claim 1, further comprising a) an nPOMC2 element comprising the nucleic acid sequence as set forth as one of SEQ ID NO: 10, SEQ ID NO: 11, SEQ ID NO: 12, SEQ ID NO: 13, SEQ ID NO: 14, or SEQ ID NO: 15, or b) an nPOMC3 element comprising the nucleic acid sequence as set forth as one of SEQ ID NO: 16, SEQ ID NO: 17, SEQ ID NO: 18, or SEQ ID NO: 19; or c) a combination thereof wherein the enhancer element directs expression of a heterologous nucleic acid sequence in a proopiomelanocortin neuron.

6. The isolated enhancer element of claim 1, comprising a nucleic acid sequence as set forth as SEQ ID NO: 20, SEQ ID NO: 21 or SEQ ID NO: 22.

7. The isolated enhancer element of claim 1, operably linked to a promoter and a heterologous nucleic acid sequence encoding a polypeptide, wherein the enhancer element directs expression of the heterologous nucleic acid sequence encoding the polypeptide in a proopiomelanocortin neuron.

8. The isolated enhancer element of claim 7, wherein the polypeptide is an enzyme, a marker, a polypeptide that confers antibiotic resistance, or an antigen.

9. The isolated enhancer element of claim 7, wherein the polypeptide is green fluorescent protein.

10. The isolated enhancer element of claim 1, operably linked to a heterologous promoter.

11. An expression vector comprising the isolated enhancer element of claim 1 operably linked to a heterologous promoter.

12. The vector of claim 11, wherein the vector is a viral vector.

13. The vector of claim 11, wherein the vector is a plasmid vector.

14. An isolated host cell transformed with the vector of claim 11.

15. The isolated host cell of claim 14, wherein the host cell is a eukaryotic cell.

16. The isolated host cell of claim 14, wherein the host cell is a prokaryotic cell.

17. An expression cassette comprising the POMC enhancer of claim 1, and a nucleic acid sequence encoding proopiomelanocortin comprising at least one exon, wherein a polylinker comprising a unique site for a restriction enzyme is inserted into the exon.

18. An isolated proopiomelanocortin enhancer element, comprising the nucleic acid sequence set forth as SEQ ID NO: 1, wherein the isolated proopiomelanocortin enhancer element elevates transcription of a heterologous coding sequence in a host cell, wherein the propiomelanocortin element is isolated from the adjacent 5' or 3' nucleic acid sequences of an endogenous chromosome comprising the proopiomelanocortin gene.

19. The isolated enhancer element of claim 18, operably linked to a promoter and a heterologous nucleic acid sequence encoding a polypeptide, wherein the enhancer element directs expression of the heterologous nucleic acid sequence encoding the polypeptide in a proopiomelanocortin neuron.

20. The isolated enhancer element of claim 19, wherein polypeptide is an enzyme, a marker, a polypeptide that confers antibiotic resistance, or an antigen.

21. The isolated enhancer element of claim 19, wherein the polypeptide is green fluorescent protein.

22. The isolated enhancer element of claim 19, operably linked to a heterologous promoter.

23. An expression vector comprising the isolated enhancer element of claim 19 operably linked to a heterologous promoter.

24. The vector of claim 23, wherein the vector is a viral vector.

25. The vector of claim 23, wherein the vector is a plasmid vector.

26. An isolated host cell transformed with the vector of claim 23.

27. The isolated host cell of claim 26, wherein the host cell is a eukaryotic cell.

28. The isolated host cell of claim 27, wherein the host cell is a prokaryotic cell.

* * * * *

SEQUENCE LISTING

```
<160> NUMBER OF SEQ ID NOS: 37

<210> SEQ ID NO 1
<211> LENGTH: 204
<212> TYPE: DNA
<213> ORGANISM: Homo sapiens

<400> SEQUENCE: 1

ggagactgag ctgagtgcct gtaaaaaggc cacttcaagc cccctccacg cagccattgt     60

tgggtctgga ggaaggagga ccgctcggaa gcttctgaat gccgccctgt gatgcactca    120

ctaatggatg tgcattagtg gcgtccttcc tggccaccac gtcactctcc ctacctcaac    180

tgctggctgg agaactccgc attc                                           204


<210> SEQ ID NO 2
<211> LENGTH: 190
<212> TYPE: DNA
<213> ORGANISM: Bos taurus
<220> FEATURE:
<221> NAME/KEY: misc_feature
<222> LOCATION: (146)..(146)
<223> OTHER INFORMATION: "n" equals any nucleotide or no nucleotide.
```

-continued

<400> SEQUENCE: 2
ggggactgag ctgagtgcct gttaaaaagg ccacttcagc cccttccatg cagcctttgt 60
tggctcgaga ggaaggagga tggttccggg ggcctctgaa tgcacctaat ggatgtgcat 120
tatcagcgtc cttcctggcc actgcnggca ctctccccac ctccacccct ggctggagaa 180
ctcagcattc 190

<210> SEQ ID NO 3
<211> LENGTH: 189
<212> TYPE: DNA
<213> ORGANISM: Cricetus cricetus

<400> SEQUENCE: 3
gggactgagc tgagtgcctg taaaaaggcc acttcaagcc ccattgtggg gatagcagca 60
ggtgggcatg tctgcgcttt gaatgcctct tccctgatgc actgcgctaa tggatgtgca 120
ttaacggcgt ccttcctggc cactgtgtct acctcccttc cccaggcccc gatggagaac 180
tccgcattc 189

<210> SEQ ID NO 4
<211> LENGTH: 191
<212> TYPE: DNA
<213> ORGANISM: Mus musculus

<400> SEQUENCE: 4
agggactgag ctgagtgcct gtaaaaaggc cacttcaagc cccattgtgg ggacagcagc 60
aggtgggcaa gtttgagctt tgaatgcctc ttcccgtgat gcactacgct aatggatgtg 120
cattaacagt gtccttcctg gccaccgcat cgctcgcctt tcctcaggcc ctgctggaga 180
actctgcatt c 191

<210> SEQ ID NO 5
<211> LENGTH: 184
<212> TYPE: DNA
<213> ORGANISM: Rattus norvegicus

<400> SEQUENCE: 5
agggactgag ctgagtgcct gtaaaaaggc cacttcaagc cccattgtgg ggccagcagc 60
aggtgggcaa gtctgagctt tgaatgcctc ttcccatgat gcattgcgct aatggatgtg 120
cattaacagt gtccttcctc cattgctctc ttttccttag accctgctgg agaactctgc 180
attc 184

<210> SEQ ID NO 6
<211> LENGTH: 408
<212> TYPE: DNA
<213> ORGANISM: Homo sapiens

<400> SEQUENCE: 6
ttctggaaaa gtagcagtca tgctcgagcc cctaacaaag gcctgtcccc cacaaaagga 60
ccattatgac caccgctgag tcagaatggt ggccgctggc acctgagctc tgtctggaaa 120
gagcggcagc agggacgtca tctagcagag cctggtgtgt ctgttatgtc cacaacatct 180
tcagcaaaga cactacttcc aggaagtcta cttggattgc agaggcgcaa gccttcattg 240
tgaaaaaagg gcttgggata aggagtggtt ctaaaagaat acatgtggct ccacatggca 300
atatacccag gtgtaataag ctcagggtaa gagagaacct gccattgctg atgcaggact 360
gtgcacacaa acttacaggc tctctactgg ggtgtcccat ggaactgg 408

-continued

<210> SEQ ID NO 7
<211> LENGTH: 387
<212> TYPE: DNA
<213> ORGANISM: Mus musculus

<400> SEQUENCE: 7
cctgaggaag ggcagcagtc agtgcctaaa ggccccagaa tggggccatt gtggtcatca 60
ctgagtcaca ctagtgacta ctggcacctg agctcagtct ggagtaagtg gtttcaggga 120
cgtcatctgg gagagtctgg tgcgagtcta acgtccagga cattttcagc aaagactgca 180
cctccaggaa gtccattctg actgcccaga aacaaaccct cattttgaaa agagagtttg 240
ggctaaggca agcttgggaa agggcacaaa aggctctgcg gaggaacacg cctacgcctt 300
gatccaggga acaagagtgg gatgttctaa cagccttgca ccacgccacg ccacgccatt 360
gcgatggcat tagtgctgcg tgtagga 387

<210> SEQ ID NO 8
<211> LENGTH: 385
<212> TYPE: DNA
<213> ORGANISM: Rattus norvegicus

<400> SEQUENCE: 8
cctgaggaag agcagcagtc agtgcctgag ggcctcacaa agggcccatt gtggtcctca 60
ctgagtcaga ctggtgactg ctggcacccg agctcagtct ggagtaagtg gttgcaggga 120
cgtcatccgc gagagtctgg tgtgactcta atatccagga catcttcagc aaagactgca 180
cctccaggaa gtccattctg actgcccaga aacaaaccct cattttgaaa agagcgtttg 240
agctaaggca agcttgggaa agggcacaag aggctctgca gaagaacacg cctacgcctt 300
gagccaggga acaagagcgt gatgttctaa cgcagggccc tgcgtcacac ggccttgcac 360
cacaccattc catcatgatg caatg 385

<210> SEQ ID NO 9
<211> LENGTH: 621
<212> TYPE: DNA
<213> ORGANISM: Artificial Sequence
<220> FEATURE:
<223> OTHER INFORMATION: The nPOMC1 complete template based on multiple species.
<220> FEATURE:
<221> NAME/KEY: misc_feature
<222> LOCATION: (23)..(619)
<223> OTHER INFORMATION: "n" equals any nucleotide or no nucleotide.

<400> SEQUENCE: 9
rgrgactgag ctgagtgcct gtnaaaaagg ccacttcaag ccccntynry gsrgmywkyr 60
kyrgstskrs angwnkgmgn nnnnytyngr rngcytctkm nnnnnnnnnn nngatgcayt 120
ncnctaatgg atgtgcatta nyrgygtcct tcctggccay yrynknnncy nnccyywccy 180
ymrnyscygn mtggagaact cngcattcyy ykngggaarrg yagcagtcan tgnnnnnnnn 240
cctrannnrg gnnnnnnccy casaawrggn ccattrtgry cmycrctgag tcasamtrgt 300
grcyrctggc accygagctc wgtctggarw ragyggywkc agggacgtca tcyrssagag 360
yctggtgygw ststwayrtc casracatyt tcagcaaaga cwsyacytcc aggaagtcya 420
ytykgaytgc msagrmrcaa rccytcattk tgaaaaragn gyttgrgmta aggmrwgstt 480
skraaagrry acawrwggct cyrcrkrrsa ayayrccyas gystnntrak cncagggwam 540
ragagnnnnn gnsatntkct rayrsmskns ynynnmsnca mrcnnnsnsn ytsynnnmyr 600

-continued ssrtnnswnc nnnrkrnmnk r 621

<210> SEQ ID NO 10
<211> LENGTH: 231
<212> TYPE: DNA
<213> ORGANISM: Homo sapiens

<400> SEQUENCE: 10
ggctgctgca ctaatgcgcg cattagtgga taaaagcagt ctcaagggtc tcttcacgag 60
gtccctttgg ctggaataaa gcaaattaaa accccattca aaggtcaatt gaaatctctt 120
tcattccagt tctctgcaca aattgattcc tctttgccct tgaggtcaaa ccgaaggctg 180
gtgaagtagc ccagctgcag tgctgcatga gagaagctca atgaaaaggc t 231

<210> SEQ ID NO 11
<211> LENGTH: 136
<212> TYPE: DNA
<213> ORGANISM: Bos taurus

<400> SEQUENCE: 11
ggataaaagc ggtctcaagg gtctcttcat gaggctcctt tggctgtaat aaagcaaatt 60
aaaaccccat tcaaaggtca attgaaatcg cttccattcc cattctttgc acaaattgat 120
tcctctttgc ccttga 136

<210> SEQ ID NO 12
<211> LENGTH: 136
<212> TYPE: DNA
<213> ORGANISM: Lepus europaeus

<400> SEQUENCE: 12
ggataaaagc tgtctcaagg ggctcttcac cgtggccctt tggctgtaat aaagcaaatt 60
aaaaccccat tcgaaggtca attgaaatct ctttcattcc acttctccac acaaattgat 120
tcctctttgc ccttga 136

<210> SEQ ID NO 13
<211> LENGTH: 227
<212> TYPE: DNA
<213> ORGANISM: Mus musculus

<400> SEQUENCE: 13
ggctactgtg ctaatacatg cattagtgga tgaaagccgt ctcaaggggc tcttcaccag 60
ggccctttgg ctgtaataaa gcaaattaaa accccatcca aaggtcaatt gaaatctctt 120
tcattcttct tctccacaca aattgattcc tctttgccct tgaggttgca ctgaatgcca 180
taaaggggcc caactgtagc tggatgggaa caagcctgaa aatggct 227

<210> SEQ ID NO 14
<211> LENGTH: 226
<212> TYPE: DNA
<213> ORGANISM: Rattus norvegicus

<400> SEQUENCE: 14
ggctgctgtg ctaatacatg cattagtgga tgaaagctgt ctcaaggggc tcttcaccgt 60
ggccctttgg ctgtaataaa gcaaattaaa accccattcg aaggtcaatt gaaatctctt 120
tcattccact tctccacaca aattgattcc tctgtgccct tgaggtcaca ctgaatgcca 180
taaaggggcc cagctgtagc tggatgggac agcctgaaaa attgct 226

-continued

<210> SEQ ID NO 15
<211> LENGTH: 234
<212> TYPE: DNA
<213> ORGANISM: Artificial Sequence
<220> FEATURE:
<223> OTHER INFORMATION: The nPOMC2 complete template based on multiple species.
<220> FEATURE:
<221> NAME/KEY: misc_feature
<222> LOCATION: (38)..(230)
<223> OTHER INFORMATION: "n" equals any nucleotide or no nucleotide.

<400> SEQUENCE: 15
ggctrctgyr ctaatrcryg cattagtgga traaagcngt ctcaagggkc tcttcaysrk 60
gnycctttgg ctgkaataaa gcaaattaaa accccatycr aaggtcaatt gaaatckctt 120
ycattcynnt tctyyrcaca aattgattcc tctktgccct tgaggtyrma cygaakgcyr 180
kwrargkrsc cnarctgyan ngctgsatgr gansangcyn nntgaaaann kgct 234

<210> SEQ ID NO 16
<211> LENGTH: 140
<212> TYPE: DNA
<213> ORGANISM: Homo sapiens

<400> SEQUENCE: 16
ctgcacctgc ccttgtaacg cactcacacc ctggtgacat ctcttttcca attaaaacct 60
caaaggtgaa aagctgagat gatgagagca gccccagccc tacgtctaca gccacctggc 120
acgcccgcag ccaggtgcag 140

<210> SEQ ID NO 17
<211> LENGTH: 145
<212> TYPE: DNA
<213> ORGANISM: Mus musculus

<400> SEQUENCE: 17
ctgcacctgc ctttgtagcg tactcacacc ctggtgacat ctcttttcca attaaaccct 60
cccatgtgaa aagctgagat gacctcagca gagtggcctc agccctgtgc ccacagccat 120
ctggcatgac tgcagccagg tgcag 145

<210> SEQ ID NO 18
<211> LENGTH: 140
<212> TYPE: DNA
<213> ORGANISM: Rattus norvegicus

<400> SEQUENCE: 18
ctccacctgc ctttgtaacg tactcacacc ttggtgacat ctcttttcca attaaaccct 60
cccaggtgaa aagccggact gacgggagca gccccagccc tgtgcccgca gccacctggc 120
atgactgcag ccaggtgcag 140

<210> SEQ ID NO 19
<211> LENGTH: 144
<212> TYPE: DNA
<213> ORGANISM: Artificial Sequence
<220> FEATURE:
<223> OTHER INFORMATION: The nPOMC3 complete template based on multiple species.
<220> FEATURE:
<221> NAME/KEY: misc_feature
<222> LOCATION: (84)..(95)
<223> OTHER INFORMATION: "n" equals any nucleotide or no nucleotide.

<400> SEQUENCE: 19

-continued

```
tscacctgcc yttgtarcgy actcacaccy tggtgacatc tcttttccaa ttaaamcctc     60

mmakgtgaaa agcygrrmtg aysnsagcag nnnnnccyca gccctrygyc yrcagccayc    120

tggcaygmcy gcagccaggt gcag                                           144


<210> SEQ ID NO 20
<211> LENGTH: 577
<212> TYPE: DNA
<213> ORGANISM: Mus musculus

<400> SEQUENCE: 20

agggactgag ctgagtgcct gtaaaaaggc cacttcaagc cccattgtgg ggacagcagc     60

aggtgggcaa gtctgagctt tgaatgcctc ttcccgtgat gcactacgct aatggatgtg    120

cattaacagt gtccttcctg gccaccgcat cgctcgcctt tcctcaggcc ctgctggaga    180

actctgcatt cctgaggaag ggcagcagtc agtgcctaaa ggccccagaa tggggccatt    240

gtggtcatca ctgagtcaca ctagtgacta ctggcacctg agctcagtct ggagtaagtg    300

gtttcaggga cgtcatctgg gagagtctgg tgcgagtcta acgtccagga cattttcagc    360

aaagactgca cctccaggaa gtccattctg actgcccaga aacaaaccct catttgaaa     420

agagagtttg ggctaaggca agcttgggag agggcacaaa aggctctgcg gaggaacacg    480

cctacgcctt gatccaggga acaagagtgg gatgttctaa cagccttgca ccacgccacg    540

ccacgccatt gcgatggcat tagtgctgcg tgtagga                             577


<210> SEQ ID NO 21
<211> LENGTH: 613
<212> TYPE: DNA
<213> ORGANISM: Homo sapiens

<400> SEQUENCE: 21

ggagactgag ctgagtgcct gtaaaaaggc cacttcaagc cccctccacg cagccattgt     60

tgggtctgga ggaaggagga ccgctcggaa gcttctgaat gccgccctgt gatgcactca    120

ctaatggatg tgcattagtg gcgtccttcc tggccaccac gtcactctcc ctacctcaac    180

tgctggctgg agaactccgc attcttctgg aaaagtagca gtcatgctcg agcccctaac    240

aaaggcctgt cccccacaaa aggaccatta tgaccaccgc tgagtcagaa tggtggccgc    300

tggcacctga gctctgtctg gaaagagcgg cagcagggac gtcatctagc agagcctggt    360

gtgtctgtta tgtccacaac atcttcagca aagacactac ttccaggaag tctacttgga    420

ttgcagaggc gcaagccttc attgtgaaaa aagggcttgg gataagggag tggttctaaa    480

agaatacatg tggctccaca tggcaatata cccaggtgta ataagctcag ggtaagagag    540

aacctgccat tgctgatgca ggactgtgca cacaaactta caggctctct actggggtgt    600

cccatggaac tgg                                                       613


<210> SEQ ID NO 22
<211> LENGTH: 568
<212> TYPE: DNA
<213> ORGANISM: Rattus norvegicus

<400> SEQUENCE: 22

agggactgag ctgagtgcct gtaaaaaggc cacttcaagc cccattgtgg ggccagcagc     60

aggtgggcaa gtctgagctt tgaatgcctc ttcccatgat gcattgcgct aatggatgtg    120

cattaacagt gtccttcctc cattgctctc ttttccttag accctgctgg agaactctgc    180
```

-continued attcctgagg aagagcagca gtcagtgcct gagggcctca caaagggccc attgtggtcc 240
tcactgagtc agactggtga ctgctggcac ccgagctcag tctggagtaa gtggttgcag 300
ggacgtcatc cgcgagagtc tggtgtgact ctaatatcca ggacatcttc agcaaagact 360
gcacctccag gaagtccatt ctgactgccc agaaacaaac cctcattttg aaaagagcgt 420
ttgagctaag gcaagcttgg gaaagggcac aagaggctct gcagaagaac acgcctacgc 480
cttgagccag ggaacaagag cgtgatgttc taacgcaggg ccctgcgtca cacggccttg 540
caccacacca ttccatcatg atgcaatg 568

<210> SEQ ID NO 23
<211> LENGTH: 227
<212> TYPE: DNA
<213> ORGANISM: Mus musculus

<400> SEQUENCE: 23
ggctactgtg ctaatacatg cattagtgga tgaaagccgt ctcaaggggc tcttcaccag 60
ggccctttgg ctgtaataaa gcaaattaaa accccatcca aaggtcaatt gaaatctctt 120
tcattcttct tctccacaca aattgattcc tctttgccct tgaggttgca ctgaatgcca 180
taaaggggcc caactgtagc tggatgggaa caagcctgaa aatggct 227

<210> SEQ ID NO 24
<211> LENGTH: 231
<212> TYPE: DNA
<213> ORGANISM: Homo sapiens

<400> SEQUENCE: 24
ggctgctgca ctaatgcgcg cattagtgga taaaagcagt ctcaagggtc tcttcacgag 60
gtccctttgg ctggaataaa gcaaattaaa accccattca aaggtcaatt gaaatctctt 120
tcattccagt tctctgcaca aattgattcc tctttgccct tgaggtcaaa ccgaaggctg 180
gtgaagtagc ccagctgcag tgctgcatga gagaagctca atgaaaaggc t 231

<210> SEQ ID NO 25
<211> LENGTH: 226
<212> TYPE: DNA
<213> ORGANISM: Rattus norvegicus

<400> SEQUENCE: 25
ggctgctgtg ctaatacatg cattagtgga tgaaagctgt ctcaaggggc tcttcaccgt 60
ggccctttgg ctgtaataaa gcaaattaaa accccattcg aaggtcaatt gaaatctctt 120
tcattccact tctccacaca aattgattcc tctgtgccct tgaggtcaca ctgaatgcca 180
taaaggggcc cagctgtagc tggatgggac agcctgaaaa attgct 226

<210> SEQ ID NO 26
<211> LENGTH: 145
<212> TYPE: DNA
<213> ORGANISM: Mus musculus

<400> SEQUENCE: 26
ctgcacctgc ctttgtagcg tactcacacc ctggtgacat ctcttttcca attaaaccct 60
cccatgtgaa aagctgagat gacctcagca gagtggcctc agccctgtgc ccacagccat 120
ctggcatgac tgcagccagg tgcag 145

<210> SEQ ID NO 27
<211> LENGTH: 140

-continued

<212> TYPE: DNA
<213> ORGANISM: Homo sapiens

<400> SEQUENCE: 27
ctgcacctgc ccttgtaacg cactcacacc ctggtgacat ctcttttcca attaaaacct 60
caaaggtgaa aagctgagat gatgagagca gccccagccc tacgtctaca gccacctggc 120
acgcccgcag ccaggtgcag 140

<210> SEQ ID NO 28
<211> LENGTH: 140
<212> TYPE: DNA
<213> ORGANISM: Rattus norvegicus

<400> SEQUENCE: 28
ctccacctgc ctttgtaacg tactcacacc ttggtgacat ctcttttcca attaaaccct 60
cccaggtgaa aagccggact gacgggagca gccccagccc tgtgcccgca gccacctggc 120
atgactgcag ccaggtgcag 140

<210> SEQ ID NO 29
<211> LENGTH: 4018
<212> TYPE: DNA
<213> ORGANISM: Mus musculus
<220> FEATURE:
<221> NAME/KEY: misc_feature
<222> LOCATION: (1243)..(3368)
<223> OTHER INFORMATION: "n" equals any nucleotide.

<400> SEQUENCE: 29
ggatcacatc acacagtcca ggctgatctg gaactcacga tgtagcagag ggtggcttcc 60
aagtagtagc aatcagctac ctcagttttc caacctggga caacagtcac ttgccatcct 120
tattgactat cttggaacga aatgcatcat acctataacg ataggagcaa ttctgcaggg 180
ctgatttata aaatgaagga atatagctga tactttgcaa aacaaataaa taaacaaaat 240
aaaacataac caaaacgaaa agaaaaaaaa aaaaaacctt tggagtcaac cggcctttcc 300
aagtaaaggg gtctgctaaa ggaccaagaa cagcctgctc tagttctggc ttcgagactt 360
gctttcaatt cacaacaaga ttttggtata cagagagagc aatgggctct tagttctgtt 420
gtggagcagg tcacgatgag ctgctctgcc ggggcccagt gtcattcacc tgggacagca 480
ggacagaagc ggtctgaacc tcaattcccg ctgcttgatt tgaagtccgg gttgctccgt 540
tcctttgtgc agcaggcatg aaaacaacag aggacaccag gcggcaggga cagggactga 600
gctgagtgcc tgtaaaaagg ccacttcaag ccccattgtg gggacagcag caggtgggca 660
agtctgagct ttgaatgcct cttcccgtga tgcactacgc taatggatgt gcattaacag 720
tgtccttcct ggccaccgca tcgctcgcct ttcctcaggc cctgctggag aactctgcat 780
tcctgaggaa gggcagcagt cagtgcctaa aggccccaga atggggccat tgtggtcatc 840
actgagtcac actagtgact actggcacct gagctcagtc tggagtaagt ggtttcaggg 900
acgtcatctg ggagagtctg gtgcgagtct aacgtccagg acattttcag caaagactgc 960
acctccagga agtccattct gactgcccag aaacaaaccc tcattttgaa aagagagttt 1020
gggctaaggc aagcttggga gagggcacaa aaggctctgc ggaggaacac gcctacgcct 1080
tgatccaggg aacaagagtg ggatgttcta acagccttgc accacgccac gccacgccat 1140
tgcgatggca ttagtgctgc gtgtaggagt gatgcagagg ctgtgaccca ggctgcccgg 1200
ccgtccacaa gatgcttttt tttttttttt tttttttttt ggntttctga gacagggttt 1260

-continued

```
ctctgtgtag ctctggctgt cctggaactc actctgtana ccaggctggc ctcgaactca   1320
aatctgcctg cctctgcctc ctgagtgctg ggatcaaagg cgtgctccac cacgcccggc   1380
tcacaaaatg cttttgccag aagtttccgt tacttagcaa gagttgccct tgcctcctgc   1440
ttctagtttt ctctgggatt aggcagaaag atcaatcgtt tgcccgtatt aggggacttt   1500
aacatataca aaggaaaaca gagagacaga tggacaaatg tctgactcct tggctcagcg   1560
ctcagagggc tttattggtc acattttgcc tgccttcctc cctccctccc ccttctttcc   1620
ttcctctcct ctcctctcct ctcctctcct ctccctctca tctcctctcc tctcctctcc   1680
tntcctctcc tntcctctcc tctcctctcc tccctccctt cttcatgtac atcaagatga   1740
tcttgaaatc actatatagt tgaagagcct gtagctggtc tttgctactt tgtgggttct   1800
ctttcccacc ttttattccc cctgccaggt ttcaccccca tcacaggtag gagagaaaga   1860
aggatagagg ggaagagaga tatgagatac cccacctaat ttctttcctt ttgtttcttc   1920
tttgaccatg gctactaata aaccacaacc atcccccta aacaaccacc aagcaccaag   1980
gctcacccct ttctcggggc cctagcactt acatgcctct gaaaagttcc tgtaactttt   2040
atatgtcaca cagtggcaga acctatctgt agttggcttt gctagaggag agggcaaatc   2100
ncagtcaact gtggtgaata gtccgaagcg tcctcaggtc tccatatctg ggattaaaat   2160
aaaaaacatt ttcttgccgg acagtggtga tgcacacctt taatccagca cttgggaggc   2220
agaggcaggt ggatttttga gttcgaggcc agcctggtct acaaagtgag ttccaggaca   2280
gccaggacta cacagagaaa ccctgtctcg aaaaaccaaa aaaccaaaaa cagaagaaag   2340
aaagaaagaa agaaagaaag aaagaaagaa agaaagaaag aaagaaagaa agaaagaaag   2400
gaaggaagga aggaaggaag aaagaaagga aaagaaaaga aagagaaaga gaaagagaaa   2460
gaaagaagaa aaggaaagaa aaaaccttct tgtaatattc tgttttattt aaagaaatcc   2520
aaattccaga atgtcactcc aagagtccta gagtaggagc cacctcactt ggttttatgc   2580
agcgctgagg attgaaccca gaattctgtg tgctaggcaa gagatgccag ctagacctta   2640
ctcccagtct cctctcacct cttcccccag cttcctcttt ccctcccccct cttcccccc   2700
ccctcccttt ttctgtaagg tcttgctatg tagttcagat tagtctataa ctcacagtgt   2760
tgggattaca ggcacgagtc accacattca actcctacca tttctttaga gttatattaa   2820
agatgatttt aatccataga acatcatgcc tggaatggac caaagaccat ggaaccctgt   2880
tttttacgat agggagatag gacaaggtag agcaagaacc caggttatct tgccctcccc   2940
ctccccaaat ccctccccct gccttctccc ttctctctcc cacactctga ttttacttgg   3000
gcctcagggt actgaaagct aattccaggg agaggccgtg ccctggcttt gggcctctgg   3060
cctggaccct tctgttctgt ggggcatgca gtccttgcag gctggggtgg gctactgtgc   3120
taatacatgc attagtggat gaaagccgtc tcaaggggct cttcaccagg gccctttggc   3180
tgtaataaag caaattaaaa ccccatccaa aggtcaattg aaatctcttt cattcttctt   3240
ctccacacaa attgattcct ctttgccctt gaggttgcac tgaatgccat aaaggggccc   3300
aactgtagct ggatgggaac aagcctgaaa atggcttccc tggggctttg gcggggatga   3360
gaggcagngg ctcctacctc ccccctgct ccctccaccc ccacaccatc gggtcaccag   3420
ggacactctc cttcagtgtg ctcttggctt ctgatcccat ctttggattc ttcccccat   3480
ccaccaggct gtcctcagag gagacccaat tccctttac tgagttgccc agcctaacct   3540
cagccttgag aggcctctgc ctcagcatcc tgggtgctgg gatggcagac atgaactgtg   3600
catcgcaaat ggacccagtg tttacactga taatattttt gtgtagtcct gggtgttcta   3660
```

-continued

```
gaatttgcac tatagaattc agagatcctc tgcctctgcc tctggagtgc tggattaaag   3720

gtgtgcagtg acaatcttaa cagcgactgg aatttctaca atctgcttga actctcacca   3780

gtcaggtgac gtaggccttt gagaggctca gagaggttaa gtaacttacc catggtcaca   3840

gagctcatga ttttctccct caaaccattt atccctcagc ctctctgtga cagcccagtg   3900

tggtacagcc agctgccagg cgtcctgaga gaacctttag tcctccgagt ggctgtgcag   3960

aaatggccag aggcactatg caaggatgcc ttctggattt tgtctttggc ttggatcc     4018
```

```
<210> SEQ ID NO 30
<211> LENGTH: 4500
<212> TYPE: DNA
<213> ORGANISM: Homo sapiens

<400> SEQUENCE: 30

ggcattattt tacattccca tcagcagcaa aatacccttt caagagtaaa taaataagta     60

gtgagacctt atttattatc ttgaaatgaa attcattgat aatataacct tctcatgttc    120

ataatacata gaaaaataac ttcaacctaa aggttgaacg ataatataaa ggataaatta    180

aaagaacata atttatacat gtttttgttt tttgagacag agtctcactc actgtgtcac    240

ccaggctgga gtgcagaggc acaatcttgg ctcactgcaa cttccgcctc ccgggttcaa    300

gagattctcc tgcctcagcc tcctgagcag ctgggactac aggcacacac caccacactc    360

tgctaatttt ttgtattttt agtagagatg aggttttgcc atgttggaca ggctggtctc    420

aaactcctga cctcaagcga tccacccacc ttggcatccc aaagttttgg gattataggt    480

gtgagccacc atgcccagcg aatacatgtt ttttgaaatg agatgttgaa gtcagagact    540

ggccttctca ggcggattag acctggtctg gaagcatttc ccctaagggg tctgccaaag    600

gctccagccc cagcccctca atggcaccaa gaacagctgc ctagggggat gctgggaaag    660

gaatcacttt caactggaca taaaggcttt ggacagcgtg ttaaaaacaa accaaactac    720

ctttcaaacc catttcagga gtcgttgcac ccttcccatc acacacacac acacatgcac    780

acacacatac acgtgcatgc acatgcacag acacacacag agtcatgggc tctttgagct    840

gctgcatagc aggtcactgt gcaccagctc tgcccagcct ggtgtccctc tcctggggca    900

atgggactga gggcacagtg gggctctcc gggccgcagg tgggctgcct ggattcgctg     960

tcctggctgc tccattcctt tgagcagcag gcatggaaat ggaagatggg tacctaacgg   1020

gggcgggggc tggagaggga gactgagctg agtgcctgta aaaaggccac ttcaagcccc   1080

ctccacgcag ccattgttgg gtctggagga aggaggaccg ctcggaagct tctgaatgcc   1140

gccctgtgat gcactcacta atggatgtgc attagtggcg tccttcctgg ccaccacgtc   1200

actctcccta cctcaactgc tggctggaga actccgcatt cttctggaaa agtagcagtc   1260

atgctcgagc ccctaacaaa ggcctgtccc ccacaaaagg accattatga ccaccgctga   1320

gtcagaatgg tggccgctgg cacctgagct ctgtctggaa agagcggcag cagggacgtc   1380

atctagcaga gcctggtgtg tctgttatgt ccacaacatc ttcagcaaag acactacttc   1440

caggaagtct acttggattg cagaggcgca agccttcatt gtgaaaaaag ggcttgggat   1500

aagggagtgg ttctaaaaga atacatgtgg ctccacatgg caatataccc aggtgtaata   1560

agctcagggt aagagagaac ctgccattgc tgatgcagga ctgtgcacac aaacttacag   1620

gctctctact ggggtgtccc atggaactgg ctctgtgtga ggagcggctg cagagggctc   1680

tttgatcagg gctggctttc cacaggccac ttggacccca tgggtggctg cctgcagcag   1740
```

-continued

```
gagtgctggt aattagtggc cccattagtt tcctctggga ttcagagtga acagagcaga   1800
gaactggcct gcccatgtgt gcagactgga gcagattctc agagagaaac aggacacgag   1860
aaaggcccaa gagacagaag gacagagctt acctcctcag cccagaggac tcagctgtgc   1920
ccattagggg ccacgttctg taagactatt gtttgtttgt tttttaatca cagagcttga   1980
ctctagatct gagcctagaa tcatagaatg acaggcctga aacggaccac atcctccccg   2040
cccccattgt tcaaatgagg gggctgaggc ctggaggtgg ggtgggggtg gggggagtga   2100
ctgacccagg tccctgtgtc tgctggccac agagctgggg ctagaaccca ggtcacctca   2160
ccccctccca ctgcttcttc ctccactcta tttttttttt tttctgaggc agggtttggc   2220
tctgttgccc aggctgaagt gcagtggcat gatcatggct cactgcagcc tccacctccc   2280
aggttcaagt gatcctccca cctcagcctc ctaaggagct gggactacag gcgtgtgcca   2340
ccatgcccgg ctaatttttg tatgtgtgtg tatatacgtg tatatatata tatatatttg   2400
tagaaatggg gttccaccat attacctagg cccttcctcc actcttgact ctgctttgga   2460
ccctgagggt gctgacaacc tgctctaggg aggggcatgg actctggccc tccccactgt   2520
gctctgcggc acccagacca tgcagacctt ggcccaggct gctgcactaa tgcgcgcatt   2580
agtggataaa agcagtctca agggtctctt cacgaggtcc ctttggctgg aataaagcaa   2640
attaaaaccc cattcaaagg tcaattgaaa tctctttcat tccagttctc tgcacaaatt   2700
gattcctctt tgcccttgag gtcaaaccga aggctggtga agtagcccag ctgcagtgct   2760
gcatgagaga agctcaatga aaaggctgag actggggagg gcgtgttgca ggggtgaagc   2820
ggggcagtgg gatccgcctg aattgtaggg ccatctgggg caccagtaac cctctcctct   2880
gcagtgcttc aggcttcagg cccttttctg gaggcagctc cctgtctgcc ctgcaaacca   2940
catcaggctc ccctcagagg gatgcttaat tagggtttct attgacaatt gtgggtgcca   3000
agagaaaatt tccttccttc actctgccct ctgaagtttt gttgaaaatg aactgctaat   3060
agacagatta ataggggaac aagacataca aattaatttc atgtgtatag catagcagaa   3120
tggtgggaga atgattaccc agtaactcaa tgaggtccag atgcctgcag atatttcttg   3180
ataggggaag ggaaaatgag ggcatagga gtaaatgatt ttctgggaaa gtgaatgcgc   3240
ccgaggaaca atggcctggg acaaagttct tctctgttct ttgggtaggt ggtgtgaagg   3300
tgagaagcag aaagtcattg tgaacgcagc ctgtcttatt atgcaggtaa ccccccctagg  3360
ctatctcttg gagttgccct cagaaaaatg caagaaaagt ctgtctggag gcggtgatga   3420
tccgtctctt ctcaggtggt taatctttct ttcctggtta tttgatgaga ttcctatgaa   3480
gggaggcttc aggcaattgt atttctttta gaaagaagtt tccttagtca gatatggaaa   3540
tgccaaagac agtaccttct ggtgttttgg aaaaaatcag agagacaggg agtgagggga   3600
aggtcagggc gagattttga aggttcttca aaggaactga agctgcttct ttagttccat   3660
attttggggt ataatttctc gagccccagt gcaattttag cggtagttag gatttcttga   3720
aagtgctcac gattcttgaa tgcccacata aaggggaaga tactgggcta tttctcattc   3780
agacacaatg aagaggaggc acttccctgt ttcaggttca tgtgtcctac agagggagta   3840
cggagatgtt actggaaagg aatcccaatc cggaccccaa aagagggtcc ttggatttca   3900
cgcaaaaaag aattctgggc aagtccatag attaaagtga aagcaagttt atttattagg   3960
aaagtaaagg aatgaaagaa tggctactcc ataggcagag cgacctggag ggctgctggt   4020
taactttttt tttttttttc tgagacagag tcttactctg ttgcccaggc tggagtgcag   4080
tggcgtgatc tcagctcact gcaacctccg tctcccaggc tcaagcaatt ctctacctca   4140
```

-continued gcctcccaag tagctgggat tacaggcgtc tgccaccacg cccggctaat ttttgtattt 4200
ttagtagaga cagagtttca ccatcttgga caggctggtc ttgaactcct gacctcgtga 4260
tccacctgcc acgacctccc aaagtgctgg gattacaggc ttgagccacc acgcctggcc 4320
tggttaacta tttttatggt tatttcttga tggtatgcta aacaaggggt ggattattta 4380
tgtttcccct tttagaccat atagggtgac ttcctgacat tgccatggca tctgtaaact 4440
gtcatggcgc tggtgggagt gtagcagtga ggaccagagg tcactctctc agtggccatc 4500

<210> SEQ ID NO 31
<211> LENGTH: 4039
<212> TYPE: DNA
<213> ORGANISM: Rattus norvegicus

<400> SEQUENCE: 31
atttgtgtgt tgattgaatg tatgctctgt gtggataggt tcctgtggag gccagaagag 60
agcatcaggc cctttgcaac tggagttcca gtctggctac ttcagttgtc caacctggga 120
caagagttat ttgcccccat gcccatcctt gactattttt tttttttttt ggttcttttt 180
ttcagagctg gggaccgaac ccagggcctt gcgcttccta ggtaagcgct ctaccactga 240
gctaaatccc cagcccccat ccttgactat tgatctattg gctatgttgg aatgaaatgc 300
atcgtgtcta tactgataga agcaatcctg cagggctgat ttataaaata aaagaataac 360
tgatactttg ccaaacaaac aaacaaaacc tttggagtca actggctttt tcaaataagg 420
ggctaaagga ccaagaacag ctgcccccgg gagctggctt acagactaga tgctatcaat 480
tctcaagatt ttggtacatg cagagagcat tgggctcttg gttctgttgt ggagcaggtc 540
acactgagct gcctcagctg gggcccagtg tcattcaccc cggacagcag gagggaggca 600
gctctgaacc tcagtttggg ctgcttgatt tgaagtccag gctgcaccgt acctttgagc 660
agcaggcatg agaatagcag aggaccctag gcagctggga cagagacagg gactgagctg 720
agtgcctgta aaaaggccac ttcaagcccc attgtggggc cagcagcagg tgggcaagtc 780
tgagctttga atgcctcttc ccatgatgca ttgcgctaat ggatgtgcat taacagtgtc 840
cttcctccat tgctctcttt tccttagacc ctgctggaga actctgcatt cctgaggaag 900
agcagcagtc agtgcctgag ggcctcacaa agggcccatt gtggtcctca ctgagtcaga 960
ctggtgactg ctggcacccg agctcagtct ggagtaagtg gttgcaggga cgtcatccgc 1020
gagagtctgg tgtgactcta atatccagga catcttcagc aaagactgca cctccaggaa 1080
gtccattctg actgcccaga aacaaaccct cattttgaaa agagcgtttg agctaaggca 1140
agcttgggaa agggcacaag aggctctgca gaagaacacg cctacgcctt gagccaggga 1200
acaagagcgt gatgttctaa cgcagggccc tgcgtcacac ggccttgcac cacaccattc 1260
catcatgatg caatgggcgc tgcgtgtagg agtgatgcag acagaggttg tgacccaggc 1320
tggccggcca tccaccaaat tcttttgcca gaagttttgg tacttaacaa gaggtctgtc 1380
ttggttctag ttttctctgg gattaagcag aaagatcgtt ggccagccca tttgaggaga 1440
ctttagcaga tacaaaggaa aacagagaca gatggacaaa tgtctaactc cttggctcag 1500
agctcagaca gctttgttgt gtccattgac catattttgt cttccctcct atctcatgta 1560
ggccaaggcc aagatgacct tgaagtcact atatagttga agacatttgt gaactcttca 1620
ctcttccggt acccatttca agagcctgaa gctggtcttt gctactttgt gggttctttt 1680 tttttttct aaaaaagatt tattcatttg ttatatataa gtgcactgta gctgtcttcg 1740

-continued

```
gacacaccag aagaggtcat ctgatcttat tacagatggt tgtgagccac catgtggttg   1800
ctgggatttt tttttgttt gtttgtttgt ttctttttct tttttctttt tttcggagct   1860
ggggaccgaa cccagggcct tgcgcttgct aggcaaaccc tctaccactg aactaaatcc   1920
ccaacccccg gttgctggga tttgaactca ggaactctgg aagaacagtc agtgctctta   1980
acccctgagc tatctctcca gcccaacttt gtagattctt tttcccacct ttaattccct   2040
ccctgccagg tttcaccccc tatcactaga tagaagagaa agaaggatgg ggggggggatg   2100
agatccccca cctaatttct ttccttttgt ttcttcttct tttttttttcc ggagctgagg   2160
atcaaactta gggccttgcg cttgctaggc aaacgctcta ccactgagct aaatccccaa   2220
cccctttgt ttcttctttg agcacggcta ctaacaaacc acaaccaatt ccataaacaa   2280
ccaccaacct cacctctctc ttggggccct agcacttaca taccctctga aaagttccca   2340
taattctcaa tgtcacacaa tggcagaaac tatcgtagct ggcaaaacca cacctctgct   2400
ggagcaagag gcaaatctta gtgagttgtt tcaaacaatc cgaaacgtcc ttgtatctcc   2460
atatgtggga ttaaaatgaa aacatttttc tataatgttt ctgtgctttt ttaaaaagaa   2520
actaaaattc cagaattatc actacaagag tcctagagtt tcagaggtgg accacctcac   2580
ctggctccat gcagtgctga ggactgaacc tagagttctg tgtactaggt aaaaaacgcc   2640
aactggacca tgctcccagt ttcttctcat ctctttcccc ctctcctttt cccccacccc   2700
ctccctcccc tccacccctt ttctgtaagg tcttgctatg tagctcagat tagccttgaa   2760
ctcacagcag tcctcctacc caagcctctc tcaagggttg gcgttacggg cagaagccac   2820
cacattcagc caccatcatt tcttcagagt cacattttag agctgatttt aatccataga   2880
atgtaatgcc tggaaggatc aaagccacgc atggaaccct gcttgcgcgc acttctccct   2940
cccacactct gactttactt gggcctcagg gtactgaaag cctgtcccag ggagaggcca   3000
tgccctagct ttgggcctct agcctggacc cttctgttct gtagggcatg cagtccttgt   3060
aggctgtggt gggctgctgt gctaatacat gcattagtgg atgaaagctg tctcaagggg   3120
ctcttcaccg tggccctttg gctgtaataa agcaaattaa aaccccattc gaaggtcaat   3180
tgaaatctct ttcattccac ttctccacac aaattgattc ctctgtgccc ttgaggtcac   3240
actgaatgcc ataaaggggc ccagctgtag ctggatggga cagcctgaaa aattgcttcc   3300
cctggggttt cggcagggac gagggtcagt ggatcctccc ctttccctag agcatctggg   3360
gcaccaggga cactctcctt cagcatgctc atggcttcag aacccatctg tggattctcc   3420
cctttcccta gagcatctgg ggcaccaggg acactctcct tcagcatgct catggcttca   3480
gaacccatct gtggattctt ccctcagtcc accaggctgt cctcaaagga ggcccaatgc   3540
ccttttacta agttgcccag cctaacctca accttgagag gtccttgcct cagcatcctg   3600
ggtgctggga tggcagacgt gaactgtgca tagcaagtgg acccagtgtt tgcactggta   3660
atctttttgt gtagccctgg ctgttctaga atttgcacta cagaattcag agactcaccc   3720
gcctctgcct caggagtgct gggatcaaag gtgtgcgtgc gtgcgaagtc ttaacagcga   3780
ttggaacttc tgcaatctgc ttgacccctc accagtgagg tgatgtgggc ctttgagaag   3840
ctcagagagg ttaagtaact gctcatgctc actgggttca tgctttcacc cctcagcctt   3900
tcccacatcc cagtgtggtg cagccagctg ctgggcatcc tgagaaattt cagaaccttt   3960
agtcttcgag tggctctgca aaaatggcca gaggcgccac gcatggatgc cttctggatc   4020
ttgtctttgg cttggaccc                                                4039
```

-continued

<210> SEQ ID NO 32
<211> LENGTH: 8705
<212> TYPE: DNA
<213> ORGANISM: Mus musculus

<400> SEQUENCE: 32
agcatggctc cgttttgtac ttgacattgt aagggaagag aactcattat gatcaactga 60
tatgttcatt tgagacagat ccttgtaagt gacagagaga aaagtaaggc ctggggtgtg 120
gttcagtggc agattacctg gttagtgtgt gagaccctgg gtttgatccc tgtactggct 180
ggttttgtgt caacttgaca cagctggagt tatcacagag aaaggagctt cagttgagga 240
aatgcctcca cgagatccag ctgtaaggca gtttctcaat tagtgatcaa gggggaaagg 300
cctcttgtgg gtggtgccat ccctgggctg gtagtcttgg gttctataag agagcaggct 360
gagcaagcca ggggaggcaa gccagtaaag aacatccctc catagcctct gcatcagctc 420
ctgcttcctg acctgcttgc gttccagtcc tgacttcctt tggtgatgaa cagcaatgtg 480
gaagtgtaag ctgaataaac cctttcctcc ccaacctgct tcttggtcat gatgtttgtg 540
cagaaataaa aaccctgact aagacaatcc ccaatgagag agagagagag agagagatag 600
attgattttt ttgtgagaac cccccaagag aacaagataa gattcttgta gtttcagttt 660
tcttcaaaac acacacttgt tcttggactg gactacgttc ctgggtgtgt actggacagg 720
agtgagttta cttcagagta ttcattacaa gtggccacaa ttggtttata cgactccttg 780
ggaaaaggtt tgccattgca gcttggcctc catgtgcagc gtgcccacca tgtgcagtct 840
tcccttgtga ctgcacactt tactcatgta actcctccta accctcagat cataaactag 900
ctgaggctct gactaaagtt ggctattacg tgagacttta gtgctctgtt ctcccaggtc 960
ccacctcctc tagggtagag gagtatgtat attctgtatc taggaaataa gaagttctca 1020
gaataatagc ttcaattcca gtttatatac aaaaccttca acttttattt atttatttat 1080
ttatttattt atttaaatat aaaaacagga tcttgtgctg gtctagaacg tgagacacag 1140
accaggctgg tctccaactc acagatctgt ctctgcctct taagtacttg gagtaaggtg 1200
tgtgccacca catctggtgt cttaactcca ctcttaaaag ctgaccagct tcttttctcc 1260
acacacagaa tccatcttat tgtaagatct cattcaggcc cttttctgac ccttcctatc 1320
cagggcccca gagtgtatct ctggccctgg agctgctggg tggcacacag cctgctttct 1380
catggtgcat gcgccctata tcccacatcg tgtgcccacc cgtgggcttc tcccttcttt 1440
cccaacatca acacaatcag caccgggaga agcaggtgct gggttagttt ccagatggac 1500
ctgagggaga tgggaaagcc accttctgct ctagcctctt tggtcaccaa gggcagcata 1560
gaaaggaact tatgctaagg cgaaggcagg ctccttgtct cttagtatcc tctttctcct 1620
ctcacaaata gccagaaatt tgctctgtgc tgtgcccttg gcaccaatcc agcctttggg 1680
ggcctttact caaacagcaa tggaagctgt atttctgtca gggggccctg ggaggccaca 1740
gtgtgctcct actttagggc agctacttca gtgtttccat ggagatcagg ggtcagggct 1800
gagctgagct tgcttgctcc ccccctcaga aatcagggaa cccagcctcc caaacatagc 1860
tgggtagtag tctcatcccc atgacctttc tcctggtgag gtgaccccta gtgctcagcc 1920
ccagtgggga ggctgagagt caggccatct tcatgtgtcc ggtgttgggt tctctgccat 1980
ctggtcctcc tccgagtccc cctccgtacc ccttctagcc cttacctccc ataaggaggc 2040
catctctgca cctgcctttg tagcgtactc acaccctggt gacatctctt ttccaattaa 2100
accctcccat gtgaaaagct gagatgacct cagcagagtg gcctcagccc tgtgcccaca 2160

-continued gccatctggc atgactgcag ccaggtgcag aactcccagg agcctttccc atgcaggtca 2220
caagactcag aagcccttcc cggcagtctc tccctctccc cttccctccc tccatctctc 2280
ctttcttcct tccaccctct gccttcctgc cagcattttg atggcatcga ggacaaagct 2340
tcccacttgg ctccaggccc tgctctgaga acttattgag ttctaacaca tggaggtagc 2400
agttgatcca aacaaactgg taaagaactt tgtgaacctt cgaaacacat atgcagcaag 2460
caaggacagt gctcgaatct cctccgagtt gttttaggga aatgaaagct aaaggcccgg 2520
gggatcatgc caggcagcaa agttgcatcc tgaaggttct ggaacacagg ccaggcttta 2580
ccccaacatt tcctctgact ggaactcctg catagttcct gaacccctt tttgagtagg 2640 ctggtctctg tttatccctc acctgtgcag tgagtgtgtg cagggtgttg ggtgaaggga 2700
aactctcttc aatgttaaac ttctttaggt tcagaagcac atacagagaa ttccatagag 2760
atggaaagag gggatcccag gagcccttac acccaccatc tctcacactt gagcgttttc 2820
agcccaggat ccataactgt ggataactag cttcaggagc catcatcctc ctcaggctcc 2880
aagctgccca tggtggagca gggacctgat gcctgaaccc tactctcagt gcagatacct 2940
gagcagatta aatgctgttc ctgcagacct ctctctctct ctctctctct ctctccctct 3000
ctctctctct ctcctagatt tattttttat gtgtaaggta ctggttagtt catattgttg 3060
tctagattat ttattattat atgtaaatac actgtagcgg ccttcagacc cgcatcagat 3120
ctcattacag atgattgtga gccaccatgt ggtttctggg atttgaactc aggacctttg 3180
gaagaagagt cagtgttctt aaccacaaag ccatctctcc agccctgcag acctcttaac 3240
actggggtgg gctgtgactc acctagataa ccagagcagc catcatttaa tgcttgggta 3300
catttttatc tttgtttctg cttctatcca caccttcacc catatttata cctacatctt 3360
ttatgtcccc catttaacag tacaccgtag ctatttctgt tgaagaataa atagccatat 3420
tcttttttaa agaagattta ttcttataat ttttaatcat gtgtgtacct gtgtgtgagt 3480
ttgtgcacac gagtgcaggg gtctacggaa gttggatgct ttggatacct tggagctgga 3540
gctacaggca gctgtgaact gcctggtgtg gtgctgccta acgtgggtcc cagcaagaac 3600
agtgcgtgct cttatctgca gagcggtctt tccagctcct gttgttattt tggagagtca 3660
cagaatattc cactgtatga cgtcactata attctcataa ctgtatctta ggattgactt 3720
tattttattg ttgctataac tgacatatga agtcttgaag aaaatttagt gctaaatagt 3780
tttcttggga taaatattag gacatgctag gtcagaagtt taaagacttg acataaagaa 3840
aacccatcca tcctcctctg gtttatccta ccagcctatt taaatcttag agctcctcct 3900
cttcccattt cacccttatc ctgttagatc agaagcccca cccaccccac cccactgcag 3960
ctgtgttcaa ggatcagctt cagttttgga tcccatctct ggtctgctta aggcgtagag 4020
tacttggctg ggcttggtgg tgcacacctt taatcccagc acttgggcag cagaggcagc 4080
agtagatctc tgagtttgta ggccagcctg atctacaaag caagtttcag aacagctagg 4140
aatgttacac agagaaaccc tgtaaaaaac aaacaaacaa acaaacaaac aaaaacagag 4200
tatttatttt tctcattagc aacagtaagt tttgccttgc tcctgggttt cccgagtcag 4260
taaatatgtt ctaacctctg ttatcttttg ttttgagaca gggtcttata tattttctag 4320
gctggcctgg aactcttgat tcccctgcct catcttccta gatgctgggg ttacaggtat 4380
gcacccgctg tgcctgtcaa cgaatgtcat catccctgat cctgcatgac ttttgttgtg 4440
acaggaagta tttgtgaacc ccaaaagacc accaaggaat ggtttcttta gggcctcttt 4500
attacaagct ctcctccaac ccaacccagc aggacaggaa gaaaagaagg agcagccttg 4560

-continued

```
aaccctcagc aggacaaggt tttataggaa atggaagtga gcgggagtct gtcctgacaa   4620
gtatctaacc aaatgtctat tgtaagaaga taggtgggtg ctctgaatgg gtgtacattt   4680
gaaagtacct ctgaaacaat cagactaatt tgtgattaat cattgctagg gaagtagcta   4740
gatagtaatt ctgtccaagg ataagctgtg gggtctttcc tagtacctgt gtgcagcttg   4800
ggttctgccc taggtcaagt ttatttctct ttgtagctct gtctgtcctg gaactcactt   4860
gtaggccaga ctggccttaa actctctttt tttttaatta atttatttat ttattatatg   4920
taagtacact gtagctgtct tcagacgctc cagaagaggg catcagatct tgttacagat   4980
ggttgtgagc caccatgtgg ttgctgggat ttgaactcca gacctttgga agagcagtca   5040
ggtgctctta cccactgagc catctcacca gcccggcctt aaactcttag agagccatct   5100
gcctctgctt ccaagtgctg ggattaaagg cgcatatcac caatgcccag ccaaaaataa   5160
gatattttga actaaatggt aattttaaaa attacatact aagaattgct agaaagacat   5220
ttacggtcat atctacacat gaaaaaaaat agaggttgaa tgtcagtgat ataagtaaaa   5280
ataatagttt attatccaat ttgagtacag aaaggatagc taactaagca tgtggaaagt   5340
agaaggtaat aatcactaga aatttcaaga atacttctga ataacacaca tgcaatagag   5400
agaattaaca ataccaaaga tgactattgt taaaaaaaac ttataaaatt gataaacatc   5460
taagaaaaag agaatataaa ttactaatac aagacagcta gagtctacag atgctgagga   5520
catgatatag ctcagtggtt acctcaaatg tgtgaagctc tgggtttagc ccccagttcc   5580
acaaaaacta aaaggccccc aaacaaacaa acagaagaga aaaggaagct ataatatgcc   5640
attttaagca aaaacttaaa gaatttttat gaagtggata aattcctgaa aaatcacatt   5700
gtactcaagt tgacacaaga agaaatagac aatgggaata gtattaatta ggcaattgaa   5760
tctgtaaata aaaactgttc agcaagtcag ggggtggtgg aggcaaacac ctttaatcct   5820
agcacttggg aggcagaggt aggcagatct ctgtgagttc aaggtcagcc tgctctacag   5880
aatgagattc aggactacca gggctacaca gagaaaccct gtcttgggac actccttctg   5940
cccaaagaaa tctgttcaaa aaacaaagca gacatcttaa aagcctctaa ggtatcaggt   6000
atgtatcact tctaaccttc aatgaagaca taatagcact atcctgagtt aaaacaggaa   6060
ggagagagat ttcaacctgt ctgtgaaaac agtgcatttt tgataccaaa cttgacaaga   6120
acaataacaa caaagaaaga aagttagagg tcactctcat gaaagtagat gtggctacgc   6180
cagtgcctgg caaatacaga ggtggatgct cacagtcatc tataagatgg aacacagggc   6240
ccccaatgga gaagctagag aaagtaccca aggagctgaa ggggtctgca accctatagg   6300
tggaacaaca atatgaacta accactactc ccagacctcc tgtctctagc tgcatatgta   6360
gcagaagatg gcctagtcgg ccatcattgg gaagagaggt cccttggtct agcaaacttt   6420
atatgaccca gtacagggga acgccagggc caagaagcag gagtgggtgg gtaggggagc   6480
aggacagggg gagggtatag ggaactttcg gggtagcatt tgaaatgtat gtaaagaaaa   6540
tatctaataa aaaagaaaaa aaatgctagc catgccaggc ggtggtagtg cactccttta   6600
atcccagcac ttgggaggca gagacaggtg gatttctgag tttgagacca gcctggtcta   6660
caaagtgagt gccaggatag ccagagctat acagagaaac cctgtctgga aaaaaccaat   6720
caaccaacca aacaaacaaa aacccaacaa caaaaaacaa acaaacaaaa gtcaaccaaa   6780
caaacaaaaa aacccgctag ccacggggct gggatatgac tcagtggtta agagcattga   6840
ctgttcttct agaggtcctg agttcaattc ctggcaacca catggtggct cacaacaacc   6900
```

-continued

```
tgatgtcctt tcctagtgta tctgaagaca gctacagtgt actcatataa ataaataagt   6960

cttaaaaaaa agaagaagaa gaagaagaag aagagtgctc agcggttaag agcactgact   7020

gctcttctga aggtcctgag ttcaaatccc agcaaccaca tggtgactca caaccattcg   7080

taatgagatc tggtgccttc ttctggtgca tctgaagaca actacagtgt ccttagatgt   7140

aataataaat aaatcttaaa aaccaaaagg ccccagaagc tagttatatt agatgcactc   7200

atcagtatta atttggcttc tttggaagca cagtgtgtta agcattggaa agcaatcaag   7260

aattcactac agtgttacac taagtgaggc cttcagaggc acctgctcca ggctatcaaa   7320

gaagaactat taatgttaag atgcaaagaa aatggagact ttttcctggt gacatccatg   7380

ttcaatgcct gtgtggtaac aggatatcct gtggcctttg accctgattc tgatctggtt   7440

ttcttttctt ctttttaaa atattttta atctttaatt tttattttat gtcctctgat   7500

gagtgtatgg gattgtggaa tccctcagag ctggagttta tagacaggca tgaactgcca   7560

tgtacgtgtt gagaattgaa cccaggacct ctggaagaac agccagtgca cttaaccact   7620

gagccatctc tctaggccct ggttttcttt tctctttact gattttggcc gtgggtccag   7680

ccaccctgtc tcctgccctc cccctttaca tcctatagcc caaccagtgt ttcctaatgt   7740

tgtttaataa cttttcaagc ttttcagttc atattggcca aagcaagttc ttctatatat   7800

aattaggagc ccagatgatg ggccaaccca aacttacctt gatttgactt tgaggctgcc   7860

agtagcaagc agccccctaa agacagaaca ataaagcaaa ggaaaacaaa gacaaaatca   7920

ccacaattag agagctggtg agcctgatgt cggtgagggc agaggtggat gggaggttga   7980

agacagaagt gtattagttc aagtataata agctacatat acagatgaga caagaatggg   8040

gttccctgcc gaacacagat catttctcag gctcctggca gaaataatag ccaaaggggg   8100

cttaatatga actgggagat gatggggagt aacctcactg gagggacaga gggtgctaag   8160

cttccgggaa acactcaggg aagtagaggc agaaagtagt gctcatggag tatgagtgtt   8220

gggagtatgt gacacccagg atacaagatg gacagcagga agtcactccg gaaagaggcc   8280

acagccaggt gacacactcc ttgctcttgt ttgggagctt ggtgtgttct ctcatggcac   8340

aaaaggaaaa gatttttgga tgccaatcag aaaagctgaa ctctcaaagg agccctggaa   8400

tcccccaaac aaaacaaagc aaatagacaa gcaaacagcg tctaactggg gagtgaagtt   8460

ccttcagctg gtagattagg caggcacccc gactggtctg gtacaggcct ggtcctgctg   8520

ccagccacag ctctcttcac aagttttgct ctttgtgctg gctcaggtag atgccactgc   8580

aggtctgttc ttccttctgt tttggcctgt gagttcacag ctaagccaga atgcctgggc   8640

ctggccacat ggtgagggct gtcagacaat ccccacccag accattctgc cagctcagcc   8700

ccggg                                                               8705
```

<210> SEQ ID NO 33
<211> LENGTH: 6323
<212> TYPE: DNA
<213> ORGANISM: Homo sapiens

<400> SEQUENCE: 33

```
tttgttttgg tgggttttgg ccggcttctt tactgcaaac tgttttatca gcaaggtctt     60

tataacctgt atcttgtgcc gacctcctat ctcatccaat gacttagaat gcctaaccat    120

ctgggaatgc agcccagtag gtctcagcct cattttaccc agtccctatt caagatggag    180

ttgctctggt tcaaacgcct ctgacaaaga gggttttgga gaatcatgag tttctgcaaa    240

ctgagggtta agagggagag ggtctccctt cctcattcat cccctcctac ccttgctgta    300
```

-continued

```
caaatatttt tcaagcacca actctctacc aggcactgat tatgggagct gtgcccttag    360
aggcaaccgg caccagctga gcagcccaag ggcccctcta gaccaaacaa cagcaggaat    420
gaagaggccc tggctgagcc taaggagttc cgagaaggga caattgttat tccatgagac    480
agggatggca gctgccccca gcttgtccat ggagactatg gagagagaat gaagaagggc    540
gtgccaaggt ggagctgggg ctcctcgttc agacccttaa ggcatgaatt ggtgcttatt    600
ccagcaaagt cccccacaga catgaggcag cttcatccct aagtcttctc ttctcccagg    660
gtaatgtccc ccattgccag tcccaatgcc tggaggctga caacgaggcc accctccttg    720
tacctcctta tcccctgccc catgttgggc tctgccaccc tgtccttgtt tctgtcctct    780
cagtcatcag cctcccctgc acctgccctt gtaacgcact cacaccctgg tgacatctct    840
tttccaatta aaacctcaaa ggtgaaaagc tgagatgatg agagcagccc cagccctacg    900
tctacagcca cctggcacgc ccgcagccag gtgcaggtgc atcgccccgg ccccaggagt    960
cctcacaagc agggtctccc aacaaaccca tcagctaccc tgtccaaaag accctgtgtc   1020
tgctcctgtc ttacctcctt ccctcctttc ttccctcctt ccttctttca tttattcctt   1080
ccctcctttc ttccttccct ccctccttcc ttcttgtctt ccttccttct ttccttccct   1140
cctcccttct tttatgtctt ccttccctcc cttccttgct tcttcctccc tctctttctc   1200
cctccttcca accttgcctt ctttccttcc ctccctcctt ctacttcctt cctccctcta   1260
tccctctctc cctctctccc ttccttcctt ccttccttcc ttccttcctt ccttccttcc   1320
ttcctcttcc ctcctccctt ctcaccaaca ctcccataat attaaagtta agggctagca   1380
gttgtacagg actaactagg gaccaggccc tgctctaaga tctttacatg aattgcctcc   1440
tttaatccat atgacagata gtggtcgagc tggagtatac aaacaaaaag aagcttttga   1500
gcccctgaaa taccataggc aggaagcaag caagaaaatt attcaggtgc aaatcttggc   1560
tattatggaa aaggaaagct aacacagaga atagaccaag agcccagagg atggaaccaa   1620
gagcccagag gatggaacca agagctaagg agattcattc cgggcagtgg aactgccttc   1680
tgaaggaact ggtcacgtgg tcacacgtgc caggccagat ttcagaattt cctttttttct  1740
cttttctcta tttctttctt tctttccttt tttttttttt tttgacagag gcttgctctg   1800
ttgcccaagc tggagtgcaa tggcctcact gcaacctccg cctcccaggc ttaagcgatt   1860
ctcctgcctc agcctcccaa attgctggga ttacaggtgc aagccaccat gtctggctaa   1920
tttttgtatt tttagtagag atggggtttc accatgttga tcaggctggt ctcgaactcc   1980
tgaccttgcg atctgcccgc cttggcctcc caaagtgctg ggattacagg catgagccac   2040
cacgcctggc cctttctgcc atctttatcc ttgatccaac attaccctcc acccacaatc   2100
accattcagt tcatagagtt ttgttttgtt ttgttttgtt ttgaaacaga gtctcgctct   2160
tgttgcccag gctggagtgc agtggcatga tcttggctca ctgtaacctc tgacttccgg   2220
attcaagcaa ttctcctgcc tcagcttcct gagtagctag gactacagac atgcgccacc   2280
atgcctggct aatctttgta cttttagtag agacgggatt tcaccatgtt ggccacagtg   2340
gtctggaact cctgacctca ggtgatccgc ctgcctcggc ctcccaaagt gctgggatta   2400
caggcgtgag ccactgtgcc cggctgagtt gtgctgtttt tatgccagga tcaaatggag   2460
aaatgcacaa aaatagtgag gagatttaaa aagcatactt ttctcagtaa ctaatagaat   2520
aagacgacaa atagcaagga tataggtaga gaaaggatat agaatatttg agaatataca   2580
gtcacagaat acagtgcagt gagacacttc ttttggagtg cacaggaagc cctaatcaaa   2640
```

-continued

```
atgagcccta tgtttatctg ttaagcaagc ctcaaaaaat ttcgaaggtc tgaaatcaaa   2700
cagagcatat tctctgacta caagggaatt aagcaaaaaa ttagtttaaa aacatgactg   2760
gaaaatcccc aaggtttaga agtttttctt tttttctaa gttggtaata tgaattggaa   2820
gggttagagg ttaagcagaa tatatttgaa taacctatag gtcaaagaag acatctcaat   2880
gaaaataaaa agatattttg aacaaatggt aattgaaata tgacatatca aaagttgtgg   2940
gatgcatata aagctgtact tagaaagaaa atatagccat aaatacatat gtaaaaaaag   3000
aataaaggag ctgggcacag tggcatgcat ctatagtccc agctactaga gagactgaag   3060
tgggaggatc actggagccc aagagttgaa gatgagtcaa ggcaatatta aaaaaaaaaa   3120
aaaaaaaaag gaaaaaaatg gttcaatatc aattatctaa gtaaaagtat ttatttaatg   3180
tccaactcat gagtatagga aaagaatagc taattaaacc caaagatgta gaaggcacga   3240
tataataaga gtaaaaattt cagaaatata aaaaagtata catatagtac agaaaattaa   3300
cagaaccaaa atggattatt aaaaagacta ataaaatgga taacacccta agaaaactaa   3360
tcaagaggcc aggcacagtg gctcacgcct gtaatcccag cactttggga ggctgaggcc   3420
ggcagatcac ctgaggtcag gagtttgaga ccagcctggc caatatggag aaacctcatc   3480
tctactaaaa atacaaaaaa taagccagat gtggtggcac atccctgtaa tcccagctac   3540
ttgggaggct gaggcaggag aattgcttga acccgggagg cggaggttgc agtaagccga   3600
gatcatgcca ttgcactcca gcctgggcaa taagagtgaa agtctgtctc aaaaagaaaa   3660
aagaaaatga atcaagaaaa aagagaacac aaataaccaa tatcagagat gaaaagggcc   3720
aaaaccacag atcccagatg cttaaaatat ataataaaca attttaagcc aataaattaa   3780
agaatttaga tgaaatagac aaattcctag aaatacatat ctgactcaaa ctgacacatg   3840
aagaagtaga caattgaaat agtgccactt aagtaattga atttgtaatg gtttaaaaca   3900
tttttccttc ttttttccag ctccagctga aaggattgat tctgtaatta aaaacttcaa   3960
tgaacaaaca atcttaaaga tttagatggc atcactggtg aatcatccca aacatttaag   4020
gacgagataa caccattata cgcaaattat tctacttaat tataaaaagg gggagggaag   4080
atggatttcc aacttgtttt atgagaacag cataattttt tgatactcaa attagacaag   4140
aattccacaa gaaaggaaaa ttacaggccc atctcatgaa catcaatgca aatgtcttaa   4200
ataaaatatt agcaaattga gtccagtgct ttctgtataa ggataataca tcataatcaa   4260
attgggttta atctaagaag ccatggtagg tttaacacca aaaaatcaac aatgcaataa   4320
ttcaccacat tactagaata aaggtgaaaa attatgtcat gtcagacaat caaaggcacc   4380
tgttctaggc tttcaaagag gagctagtgg tacaaggatg caagggcagt ggtgactcct   4440
ttctagtggc attagctgaa gtgagaatgg cagcgtccca tcctggggac agaagtgacg   4500
tctatgtcag acgcctgtgg tcttgacatg ccccttgtgg ccccttgtgg tctgtttttt   4560
ttttctccac tggatgtgat tttggccatg gttccagcca cactgtgtcc ctgcccattt   4620
ttagatcctg gtcccccaac ctgcccagtg attttttttt tttttagat ggagtcttgc   4680
tgtgtcgcca ggctggagtg cagtggcgcg atctcggctc accgcaacct ccgcctccca   4740
ggttcaagcg attctcctgc ctcagccacc cgagtagctg ggactacagg tgtgcgccac   4800
cacgcccggc taatttttgt atttttagta gagacggggt ttcgccatct tggccaggaa   4860
tgtctccatc tcttgacctc gtgatctgcc caactcagcc tcccagagtg ctgggattac   4920
aggcgtgagc cactgtgccc cgcctaccca gtgattctaa atgcagttca atggcctttc   4980
agttcatgga ggccaaagca ggttctgctg cattaaatta agaaactggg ctgggtgtgg   5040
```

-continued

```
tggctaacac ctgtaatccc agcacttcag gatactgatg tggattactt gagcccagga   5100
gcttgagacc agcctaggca acatagtgaa accctgtctc taccaaaaac aaaaacaaaa   5160
acaaaacaaa aaaccaaaac ccaaaattag ctgggcatgg tggcatgcat ctgtggttcc   5220
aggtactcag gaggctgaag catgaggatc acttgagccc aggaggtgga ggctgcagtg   5280
agcagtgttc acactgctgc attccagcct gggcaacaga gtgagaccct aattcaaaaa   5340
caaacaaaca gaatgagaga gagagagaag aaaagaaaga aggaacccag ttaaagaagt   5400
tgggtccatt tggatttttc ctggtttgtt ttatctgctg ccaccagcag cctcctgaag   5460
ttacaaaaat aacacaaagt aaaataaggc aaaaccacca tctgcttgaa agagtttaca   5520
aacctgatgg tggtcgtggg gtggatggaa gattaaaaaa atggggacag aagtgaatta   5580
gtgcaagcca cttgcactga caagatgggg atggacttct gtggaaggca gaggaggtca   5640
tgcctcatgc ccctggtagg aaaagtggcc aaagagggct tcagagaaca ggggctgatg   5700
gatgggctac atcttgatgt gagtcaagct cctggatggc tggagagagg aaggatgttc   5760
tagttggggg aacagcttgg acaatggaga cccaagaaag ccatgttcta gcagtgtgaa   5820
tgttgtggat gctgaagtgc caggatgcaa ggtggagaac tgggaaatgg ccctggaaag   5880
gggccaaagc cgggtgatga agcaccttgt ctactgtgac ggagcttgga tctctcttgt   5940
ggtccaaagg gaaaggattg ctgaatgtaa agccaatgtc accagaaaag ctgaatccac   6000
aagagagtcc tggagtccaa aagagcatct catggggaat caggaaagtt ctggcatttg   6060
gcagattaag caagtgtctt gatttgaagt ccagtttagt cccaatactc cctcccacac   6120
ccaccacatc gcacaatttg gttttgttta tttactccag gttaaggtag agtctcttag   6180
cttggtttga gtgctgtact cttctctctg gtctgatatt tggaactaaa gccaagccag   6240
aactccaggg ccaaggggga tgttgaaaat tgtctgagtc cccagaccac cctgccagct   6300
catggcaaag ggagggatca gag                                           6323
```

<210> SEQ ID NO 34
<211> LENGTH: 9144
<212> TYPE: DNA
<213> ORGANISM: Rattus norvegicus
<220> FEATURE:
<221> NAME/KEY: misc_feature
<222> LOCATION: (2279)..(3087)
<223> OTHER INFORMATION: “n” equals any nucleotide.

<400> SEQUENCE: 34

```
agcatgtctg gggtgtggtt cagtggcaga ctacctggtt agtgtgtgag accctgggtt     60
tgattcccaa cattagtgag aaagagagag agagagagag agagagagag agagagagag    120
agagagagaa tttttgtgag agaaccccaa gagaaaaaga taagattctt gtggtttcag    180
ttttcttcaa aacacaaaat tgttcttaga atgtgtttgt gggcccctct caggggtatt    240
ggataagagt gagtttactt cagattattc actctaactg attattatcg gtgcgatatg    300
tctccttgga aaaatggttt gccatgcgca gcttggcctc caagtgcagt ttgcccaccg    360
cctggtgcct gccctctgca tgcagcgtgc ctgccatgtg ccgttcgccc cgttcgcctt    420
tgtgattggg cacgttcctc atgtgactct tcttagccct cagagtatga accggctgct    480
tctctgacta aagctggcca ttactcgaga ctttcgtgct ccttgtttta ttggctccat    540
tctcccaggc cccatcacct ctagataagt atatttcata tccagggact aagaagttct    600
cagaataatg gctttgactc cagctcatgt gtaacatctt caactttaaa aaaaaaaaac    660
```

-continued

```
aaacaggatc tcgggtaact caggttggcc tggaactcga cacatagacc aggctagcct    720
ccaacccaca gatctgcctc tgccttccag gtactgggat taaggtgtgt gccaccacac    780
ctgctgtcct aattctgccc ttagaagctg accagatcct cccccccaca cccagaatcc    840
agcttattct aacgtctagt ttaggccctt tcctgacctt tcttatccag agccccagag    900
tgtaccccctg gccctgggac tgcttggcag tacacatcct gctttcccat gatacacact    960
ctatacctca catccatgct tactcgtggg ctttcctctt ctcctctcca acaccagtgc   1020
atcacaactc aacacacgaa ggcacaggtg ctgggttaac tcccagatgg acctgaagga   1080
ggtgggaaaa gtcatcttct gctccaggct ctttggtcct caagagcagc ctagaaagga   1140
tcttaccagg ggaaggcaaa aggggactcc tggtccctta gtctcctctt tcttctctca   1200
caaaaaaatt gccccttgct gtgtccttgc caacagtggc accagtccaa cctttggagg   1260
gcctttcctc aaacagcaat ggaaagctgt tattctgtca aggggccctg ggagggcaca   1320
atgtgcttct tctacctcag ggcagctatt cctacatttc cgtggagacc aggggtcagg   1380
gccaagctga acttgcttgc tctcaccctc agggctcaga gagcccggtc tcccaaacgg   1440
agttgggcta cagtctcatc ccaatgactt ttctcccggt gaggtgaccc ctagtactgg   1500
ggtgttgggt gtccggtgtt gggctctctg ccatctggtc ttccttccat tccccctccc   1560
cacccccgct agccctttc tctcataagg aggtcatctc tccacctgcc tttgtaacgt   1620
actcacacct tggtgacatc tcttttccaa ttaaaccctc ccaggtgaaa agccggactg   1680
acgggagcag ccccagccct gtgcccgcag ccacctggca tgactgcagc caggtgcaga   1740
actctggctt taccatgcag gcgtcacaag agtcagtcag aagcccctct gggccatctc   1800
tccctctccc cctccccttc ctccctccat ctctcctttc ttccttccac cctctgccct   1860
cctgtctgca tttcggtgac ctcgggaaca gagcttccca cttggttcca ggccctgctc   1920
tgagaacttt ttgagttctc acgtggcagg cagcggtgga accaaactgg taaagaactt   1980
tgtgaacctc caaaacacca catggaggag caagcaagga aaggggtcga ctgtcctcca   2040
ggttgtttag ggaaatgaaa gctaatacag aaaaggctgg gagtccccag aatgcaccaa   2100
tggttctgga acccaggcca agccgtaccc cagcatttcc tctgactgga actcccgtgt   2160
agttcctgaa ccccctttct ttttttttatt tttatttatt tatttatttt ttttattaac   2220
ttgagtattt cttatataca tttcgagtgt tattcccttt cccggtttcc gcaaacttnc   2280
cccctacctt attgcctgcc attgaggaaa aacaaaaagt ctttgtttgg ttgttttttt   2340
ttaaaaggtt tctctgtgtg acagccctaa ctgttctgga acttgctttg tagaccagcc   2400
cggcttacaa actcacagag atccacctgc ctctgcctcc caccccaagc gctgggatta   2460
aaggcatgcg ccaccatgtc cagccaaatg ctctaagtct taagcagacc agagatggga   2520
tccaaaactg aagctgatcc ttgaactcag ctgcagtggg gtggagaact tctgctataa   2580
caggatgtgg gccaagcggg aagaagagga gaagatatga gatttaaata ggctaaacca   2640
gaggaggctg aatgggtttt ctctatatca agtctcccaa gaaagctatc tagcaataaa   2700
ttttcttcaa gacttcatat atctgttata gcgacagtaa gataaagtca acgccaagat   2760
acagttatga gaattatagt gaagtcatac agtgaaatat tctgtgactg tttataacaa   2820
cagtaggaac tggaaagatg gtcctgtaga caagagcacg tgctgttctt gctgggaccg   2880
gagttagaca gcaccatgtc aggcagttcc ctttagctcc acctccaagg tatccaaagc   2940
ttctggtctc catagacacc tgcactcatg cgcacacact catacacaca cacacacaca   3000
cacacacaca cacacacact cagatacaca tacaatcnnn nnnnnnnnnn nnnnnnnnnn   3060
```

-continued

```
nnnnnnnnnn nnnnnnnnnn nnnnnnnccc tcccaaccct ccccccattg ccgtcctccc   3120
ccccacagtc tagttcactg gggggttcagt cttagcagga cccagggctt ccccttccac   3180
tggtgctctt actaggatat tcattgctac ctatggggtc agagtccagg gtcagtccat   3240
gtatagtctt taggtagtgg cttagtccct ggaagctctg ctgaaccccc tttctgagga   3300
ggctggtctc tgtttatccc tcatgtgtgc ggggtgttgg gtgaagggaa actgtctctt   3360
cagtgttata gttctttagt ttcagaagta catactaaga atccccgcca atgttccaca   3420
gagatggaaa gaggggatcc caagtaccct cacagccacg gtctctcaca attcgagcat   3480
tctcagccca gaatccacaa ctgtgaagaa atagcttcag gagctacaga cctcaggctg   3540
ccggtggtag agcagggacc cgatgcctga cccttcttca cagtgcagat acattgttgc   3600
tacaaaccac ttaacaacgg gctgtgactc acctagatga ccagagcaac caccatttaa   3660
cacttgggta cactttcatc tttgttcctg tttctatccc cacctttatt tattatgagt   3720
ccactgtagc tgtcttcaga cacaccagaa gagggcatca gatctcatta cagatggttg   3780
tgagccacca tgtggttgct gggattttaa ctcaggacct ctggaagagc agtcagtgct   3840
cttaaccgct gagtcatctc tccagccccc tacttacatc ttttatgttc cctgcttaac   3900
aatacacaat ggctgcttat gttggagaat aaatggccac attatctttt taagattttt   3960
tttctttttt cttttttttt tttctggagc tgaggaccga acccagggcc ttgcgcttgc   4020
taggcaagtg ctctaccact gagctaaatc cccagcttaa gatttattct tataatgttg   4080
attgtatgtg tatctgagtg tgtgtgtgtg tgtgtgtgtg tgtgtgtgtg tgtgtgtatg   4140
agtgtgtgcg catgagtgca ggtgtctatg gagaccagaa gctttggata ccttggaggt   4200
ggagctaaag ggaactgcct gacatggtgc tgtctaactc cggtcccagc aagaacagca   4260
cgtgctcttg tctacaggac catctttcca gttcctactg ttgttataaa cagtcacaga   4320
atatttcact gtatgacttc actataattc tcataactgt atcttggcgt tgactttatc   4380
ttactgtcgc tataacagat atatgaagtc ttgaagaaaa tttattgcta gatagctttc   4440
ttgggagact tgatatagag aaaacccatt cagcctcctc tggtttagcc tatttaaatc   4500
tcatatcttc tcctcttctt cccgcttggc ccacatcctg ttatagcaga agttctccac   4560
cccactgcag ctgagttcaa ggatcagctt cagttttgga tcccatctct ggtctgctta   4620
agacttagag catttggctg gacatggtgg cgcatgcctt taatcccagc gcttggggtg   4680
ggaggcagag gcaggtggat ctctgtgagt ttgtaagccg ggctggtcta caaagcaagt   4740
tccagaacag ttagggctgt cacacagaga aacctttttaa aaaaaaacaa ccaaacaaag   4800
actttttgtt tttctcattg gcagcaataa gttttgactc actcccgggt ctcccgcaac   4860
agtatgttct gacctctgtt atctttcgtt ttgagaaggg gttttatata ttttccaggc   4920
tggcctggga ctcttgattc ccctgcctca gcttcctagg cgctgggatt acaggtatgc   4980
accactgtca atgaatgtca ttatcctcaa ttctgcgtta cctttattga gctggaaggg   5040
tttgtgaatc ccaatagacc accaaggagt cctttctgat gtaatgacct tagggtctct   5100
ttattacaac cttgggttgg actctcttcc aacccaacct tgacacagca ggactggaag   5160
gggaagtgga gtagcccaga accctcagca ggacaaggtt ttataggaag cagaagtaaa   5220
tgaagggggt ggggggtcta gcctagcaag aatctaaagg aatatctatt gtgagccgat   5280
aggtgggtgc tctgaagcaa gaccatatgc aatcacgact ggtctgaaaa ttcctttgaa   5340
acagactaat cttcgataac tgttgctagg aagtagcgag gagtaactct ggccgaggac   5400
```

-continued

```
aagccgtgcg tggttccttc ctggtacgtg ggtgcagctt ggtttggctg caagtcagat   5460
tctcaggctt cttttctttt ctttacaaag gaggctcatc ccaagatgga ggaggtttag   5520
tctctcagct tcaatccctt aatgaattcc attcgccatt agatttctag aattgctttg   5580
tttttatgct aggatcaaag gggaggaact gataagtcta caaaaggaga catttaacgg   5640
acacacttct ctcgataatc taacaggata ccaaataacc ggaacagatc cagataatag   5700
agtattgagt gtctgagcaa ccacagggtg tgttcttttg gaacaaacat gaaatgctgt   5760
tcaaaatggg gtacatgttc acccattaag tcttaaacat ttccttagga ctgaaatcaa   5820
acagagcaca ctctctgaca acaaggaaat taagctaaaa aacggtttct aaaacagaat   5880
cagaaaatcc ccaaggctgg gaagataaca gaacagttct cagttcacag gtcaaagatg   5940
aaaataagat atatatttg agatggggtt tccccgtgta gccctatctg tcctggaatg   6000
cactctgtag gccaggttgg ccttgaactc ttagagatct gcctgcctct gcttctgagt   6060
gctgggatta aaggcacaca tcaccactgc ctagctgaaa ataaggtatt tcgaactaaa   6120
tggtaatttt aaaacttaaa tactaagaat tgcaagatgc aattaagaag aaccttctta   6180
gaaagacatt tatggccata tctacatatg caaaaaaata gaggttcaat gtcaatgata   6240
taagtaaaaa caattgcttc ctgtccgact tgagtagaga aagattagct aaccaagcat   6300
gtagaaagta gaaggaagta acaattagta gaaatttcaa aatacttctt gaacaacaca   6360
catgcagtag acagaattaa caataccaaa gatgactatt gtaaaaataa acttataaaa   6420
ttgatataca tctgtcttag ttagggtctt attgctgtga ccagacacca tgaccaatgt   6480
aagttttata aaggacaaca tttaattggg ggtggcttac aggttcagag gttcagtcca   6540
ttatcatcaa ggcgggaaca tggcagcatc tagataagca tggtgcagga ggagctgagt   6600
tctacatctt ctcccaaagg aagccaggaa cagactgagc atcctcaggc agctaggagg   6660
agagtctcca agcccacccc cacagtgaca cacttcctcc aacaaggcca caccttctaa   6720
tagcgccact ccctgggcca agcatatgca aaccatcaca acatccaaga aaaggagaat   6780
ataaattact aataccagac aagaaagagg cgcacaacca gagtcttcag atgctaagga   6840
cctgataaga agctataatt agactaggga tatatctcaa atgtgtgaag ccctgggttc   6900
aacccctagt tccacaaaaa acaaaagact cccccaaaca aacacaacag aaatggaagc   6960
tataacatgc caattttttt ttttccggag ctggggaccg aaacatgcca tttttaagc   7020
caaaaactta aagaattttt gtgaagtgaa taaattcctg gaaaaaaaaa acaccttatt   7080
caaattggaa caagaagaaa tagacaacgg gaataatatt aaggaagcaa ttgaatcttc   7140
aattgctaaa taaaaactgt tcagcaagcc aggtggtgga ggcaaatacc tttaatctca   7200
gtactttgga gtcagaggca ggtggatctc tgtgagttca aggacagcct actcaacaga   7260
atgagtttca gaacaaccag ggctacacag agaaaccctg tctcagaaca ccccttcctc   7320
ccaaaaacat ctttccaata aacaaagcag acatcttaga agcctggaag ccttcatgtg   7380
cgaagcactt ttaacattca aggaagacat tatagcactg tccttggctg agttaaaaca   7440
aggagagaga tttcagtttg tcttgtgaga acagtgcaaa tttgatacca gatttgacaa   7500
gagcttaaaa ataaaaagga aaattagagg ccacactcat gaaagtagag gcaaaagtct   7560
taattaaaat gctagttata taagagacac tcatcatcgt taaattgtgc ttctttgaaa   7620
gcacagtatg ttaaacgttg ggaaagcaat cagcagtgtc ctaagaactc gctacagtat   7680
tacactaaat gaggaaaact gtattgtttg aggctttcag aggcacctac tccaggttat   7740
caaagatgtt gatacaaagg caatggagac cttttcctgg tgacacccat gttcaatgcc   7800
```

-continued

```
tgtgtggtga cagtatctcc tgtgtctttt tgaccctggt tctgctctgg ttttcttttc   7860
tttttaaaat cttttattta tttttttaaa aaatatttat ttttatttta tgcccattgg   7920
tgttttgcct acatgtgtga atgtatggga atgtcgaatc cttggatctg gagtttagac   7980
aggtatgagt tgccatgtag gtgttgagaa ttgaacccag gacctttgga agaacagcca   8040
gtgctcttaa ccactgaacc ctctctctct aagccttggt tttcttttct cctttactga   8100
gtttggccat gggtccagcc acccttgtct cctgccctcc cccaccttta tgtcctatag   8160
cccaaccagt gtttcctaat gtggtttaac agcttttcaa acttttcagt tcatattggg   8220
caaagcaagt tctcctatgt ataattagga gtccagatga tagttaggcc aacccaaacc   8280
taccttggtt tgactccaat gcaagcagcc tcctaaagtc acatccataa agcaatggac   8340
aagacaaaga gcactgccaa gcctggtgct ggttagggca gaggtggatg ggaggtcaga   8400
gacagaagtg aatcagttca cgtataataa gctactgtac agatgagaca ggaaaggggt   8460
tctctgaaga aaggagatcg tttctaaggc tcctggtaga aataacccaa agtggcttag   8520
taagagccag gtgatactgg agagctagac cgtcataggg atctgagtta cctcatcgga   8580
gggacacagg gtgctcagct tccagggaac actcagggag gtagaggcag aaagaagcac   8640
tcacggaata tgagcattgg ggttagctga cgtccaggat atgagttgga cagcaggtaa   8700
tcatcccaga aagaggtcag agccatgtga cacaatcctt attcaccatt agggagcttg   8760
gtgcattctc tggtgccaca aaaggaaaag atttttggaa gcaaagtcga tactgccaat   8820
cagaaaagct gaactctcaa gggacccccct ggagtccccc aaacaaaaca aagcaaatag   8880
acaaacagac agtgtctaac tggggagtga agttccttca actggtagat taaacaggca   8940
ccgggactgg tctgatccaa tcctagtccc cctgccagtc acagctctct tcacaggctt   9000
tgctctttgg cacacaggcc tgttctttct tctgttttgc cctgtgagtt cccagccaag   9060
ccagaacgcc tgggcctggc cacacggtga aggctgtcag acaatcccca ggccattctg   9120
ccaactcagc cccagaatgg cttc                                          9144
```

```
<210> SEQ ID NO 35
<211> LENGTH: 9
<212> TYPE: DNA
<213> ORGANISM: Artificial Sequence
<220> FEATURE:
<223> OTHER INFORMATION: The consensus core binding site for STAT3.
<220> FEATURE:
<221> NAME/KEY: misc_feature
<222> LOCATION: (5)..(5)
<223> OTHER INFORMATION: "n" equals any nucleotide.

<400> SEQUENCE: 35

ttccnggaa                                                              9


<210> SEQ ID NO 36
<211> LENGTH: 17
<212> TYPE: DNA
<213> ORGANISM: Artificial Sequence
<220> FEATURE:
<223> OTHER INFORMATION: A highly conserved palindromic oligonucleotide
      sequence within the nPOMC1 template.

<400> SEQUENCE: 36

ctaatggatg tgcatta                                                    17


<210> SEQ ID NO 37
<211> LENGTH: 25
```

-continued

```
<212> TYPE: DNA
<213> ORGANISM: Artificial Sequence
<220> FEATURE:
<223> OTHER INFORMATION: An exemplary polylinker.

<400> SEQUENCE: 37

gcccgggctc gagtttaaag cgcgc                                          25
```